United States Patent
Khetani et al.

(10) Patent No.: US 10,266,806 B2
(45) Date of Patent: Apr. 23, 2019

(54) STEM CELL-DERIVED HEPATOCYTES IN CO-CULTURE AND USES THEREOF

(71) Applicant: Colorado State University Research Foundation, Fort Collins, CO (US)

(72) Inventors: Salman R. Khetani, Fort Collins, CO (US); Dustin R. Berger, Fort Collins, CO (US); Brenton R. Ware, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/596,787

(22) Filed: Jan. 14, 2015

(65) Prior Publication Data

US 2015/0240203 A1 Aug. 27, 2015

Related U.S. Application Data

(60) Provisional application No. 61/927,285, filed on Jan. 14, 2014.

(51) Int. Cl.
*C12N 5/07* (2010.01)
*C12N 5/071* (2010.01)

(52) U.S. Cl.
CPC ........ *C12N 5/067* (2013.01); *C12N 2501/237* (2013.01); *C12N 2501/39* (2013.01); *C12N 2502/13* (2013.01); *C12N 2503/02* (2013.01); *C12N 2533/90* (2013.01)

(58) Field of Classification Search
CPC .............. C12N 5/067; C12N 2501/237; C12N 2501/39; C12N 2502/13; C12N 2503/02; C12N 2506/45; C12N 2533/90; G01N 33/5067
See application file for complete search history.

(56) References Cited

U.S. PATENT DOCUMENTS

| 6,458,589 | B1 | 10/2002 | Rambhatla et al. |
|---|---|---|---|
| 8,062,632 | B2 | 11/2011 | Lee et al. |
| 2003/0003573 | A1 | 1/2003 | Rambhatle et al. |
| 2005/0079673 | A1 | 4/2005 | Seo et al. |
| 2006/0270032 | A1 | 11/2006 | Bhatia et al. |
| 2011/0262956 | A1 | 10/2011 | Elias et al. |
| 2011/0318730 | A1 | 12/2011 | Rice et al. |
| 2012/0111795 | A1 | 5/2012 | Chamuleau et al. |
| 2013/0266939 | A1 | 10/2013 | McVay et al. |

FOREIGN PATENT DOCUMENTS

| EP | 2495310 A2 | 9/2012 | |
|---|---|---|---|
| WO | WO -9851785 A1 * | 11/1998 | ........... C12N 5/0671 |
| WO | WO 2015/003160 A2 | 1/2015 | |

OTHER PUBLICATIONS

Bhatia et al. "Effect of cell-cell interactions in preservation of cellular phenotype: cocultivation of hepatocytes and nonparenchymal cells." FASEB J. Nov. 1999;13(14):1883-900.*

Bi et al. "Use of Cryopreserved Human Hepatocytes in Sandwich Culture to Measure Hepatobiliary Transport." Drug Metab Dispos. Sep. 2006;34(9):1658-65.*
Choi et al. "A comparison of genetically matched cell lines reveals the equivalence of human iPSCs and ESCs." Nat Biotechnol. Nov. 2015;33(11):1173-81. doi: 10.1038/nbt.3388. Epub Oct. 26, 2015.*
Nagamoto et al. "The promotion of hepatic maturation of human pluripotent stem cells in 3D co-culture using type I collagen and Swiss 3T3 cell sheets." Biomaterials. Jun. 2012;33(18):4526-34.*
Sazonova et al. "Stimulation of fibroblast proliferation by neokyotorphin requires Ca influx and activation of PKA, CaMK II and MAPK/ERK." FEBS J. Jan. 2007;274(2):474-84.*
Khetani et al. "Microscale culture of human liver cells for drug development." Nat Biotechnol. Jan. 2008;26(1):120-6. (Year: 2008).*
Zinchenko et al. "Contribution of Non-parenchymal Cells to the Performance of Micropatterned Hepatocytes." Tissue Eng. Aug. 2006; 12(8):2241-1251. (Year: 2006).*
Zinchenko et al. "Hepatocyte and kupffer cells co-cultured on micropatterned surfaces to optimize hepatocyte function." Tissue Eng. Apr. 2006;12(4):751-61. (Year: 2006).*
Morin et al. "Long-term maintenance of hepatocyte functional activity in co-culture: requirements for sinusoidal endothelial cells and dexamethasone." J Cell Physiol. Oct. 1986;129(1):103-10. (Year: 1986).*
Gregory et al. "The Effect of Coculture With Nonparenchymal Cells on Porcine Hepatocyte Function." Cell Transplantation, vol. 10, pp. 731-738, 2001 (Year: 2001).*
Khetani et al. "Exploring interactions between rat hepatocytes and nonparenchymal cells using gene expression profiling." Hepatology. Sep. 2004;40(3):545-54. (Year: 2004).*
Bhatia et al. "Effect of cell-cell interactions in preservation of cellular phenotype: cocultivation of hepatocytes and nonparenchymal cells." FASEB J. Nov. 1999;13(14):1883-900. (Year: 1999).*
International Search Report and Written Opinion, PCT/US2015/011363, dated May 11, 2015.
Yu, B. Effects of Metformin on Glucose and Glucagon Regulated Gluconeogenesis in Cultured Normal and Diabetic Hepatocytes, Biochem.Pharm., vol. 48, No. 5, pp. 949-954, 1994.
Berger DR, Ware BR, Davidson MD, Allsup SR, Khetani SR Enhancing the Functional Maturity of Induced Pluripotent Stem Cell-Derived Human Hepatocytes by Controlled Presentation of Cell-Cell Interactions In Vitro. Hepatology, vol. 61, No. 4, 2015, pp. 1370-1381.

(Continued)

*Primary Examiner* — Titilayo Moloye
(74) *Attorney, Agent, or Firm* — Polsinelli PC

(57) ABSTRACT

The present disclosure provides co-cultures of human pluripotent stem cell derived hepatocytes and at least one non-parenchymal cell population in vitro, methods of preparing the co-cultures and methods of using the co-cultures for high throughput screening and evaluation of drug candidates. The stem cell derived hepatocyte co-culture system provides an in vitro model in which cell viability and relatively mature hepatocyte phenotype of stem cell derived hepatocytes are maintained for extended periods relative to conventional monoculture.

30 Claims, 45 Drawing Sheets
(11 of 45 Drawing Sheet(s) Filed in Color)

(56) References Cited

OTHER PUBLICATIONS

Gerbal-Chaloin S, Funakoshi N, Caillaud A, Gondeau C, Champon B, Si-Tayeb K. Human Induced Pluripotent Stem Cells in Hepatology Beyond the Proof of Concept. American Journal of Pathology, vol. 184, No. 2, Feb. 2014, pp. 332-347.

Schwartz RE, Fleming HE, Khetani SR, Bhatia SN. Pluripotent stem cell-derived hepatocyte-like cells. Biotechnology Advances 32 (2014) 504-513.

Sjogren AK, Liljevald M, Glinghammar B, Sagemark J, Li XQ, Jonebring A, Gotgreave I, Brolen G, Andersson TB. Critical differences in toxicity mechanisms in induced pluripotent stem cell-derived hepatocytes, hepatic cell lines and primary hepatocytes. Arch Toxicol (2014) 88:1427-1437.

Bilic J, Belmonte JCI. Concise Review: Induced Pluripotent Stem Cells Versus Embryonic Stem Cells: Close Enough or Yet Too Far Apart? Stem Cells (www.StemCells.com). 2012;30:33-41.

Chin MH, Mason MJ et al. Induced Pluripotent Stem Cells and Embryonic Stem Cells are Distinguished by Gene Expression Signatures. Cell Stem Cell 5. Jul. 2, 2009: 111-123.

Khetani SR et al. Toxicological Sciences, Scholarone—Manuscripts: The Use of Micropatterned Co-cultures to Detect Compounds that Cause Drug Induced Liver Injury in Human. ToxSci Advance Access. Nov. 14, 2012.

Khetani SR, Bhatia SN. Microscale culture of human liver cells for drug development. Nature Biotechnology. 2008; vol. 26, No. 1: pp. 120-126.

Narsinh KH, Plews J, Wu JC. Comparison of Human Induced Pluripotent and Embryonic Stem Cells: Fraternal or Identical Twins? Molecular Therapy (www.moleculartherapy.org). Apr. 2011; vol. 19, No. 4: 635-638.

Erion et al. MB06322 (CS-917): A potent and selective inhibitor of fructose 1,6-bisphosphatase for controlling gluconeogenesis in Type 2 diabetes. PNAS, 2005, vol. 102, No. 22, pp. 7970-7975.

Khetani S et al. Exploring Interactions Between Rat Hepatocytes and Nonparenchymal Cells Using Gene Expression Profiling. *Hepatology* 2004;40:545-554.

Liu et al. Inhibition of Gluconeogenesis in Primary Hepatocytes by Stromal Cell-derived Factor-1 (SDF-1) through a c-Src/Akt-dependent Signaling Pathway. Journal of Biological Chemistry, 2008, vol. 283, No. 45, pp. 30642-30649.

March S et al. Micropatterned coculture of primary human hepatocytes and supportive cells for the study of hepatotropic pathogens. *Nature Protocols* 2015; vol. 10, No. 12: 2027-2053.

Sajan MP, Farese RV. Insulin Signalling in Hepatocytes of Type 2 Diabetic Humans. Excessive Expression and Activity of PKC-1 and Dependent Processes and Reversal by PKC-1 Inhibitors. Diabetologia, 2012, vol. 55, No. 5, pp. 1446-1457.

Westlind-Johnson, et al.,*Comparative analysis of CYP3A expression in human liver suggests only a minor role for CYP3A5 in drug metabolism*, Drug Metab Dispos. Jun. 2003;31(6):755-61.

\* cited by examiner

2C

2D

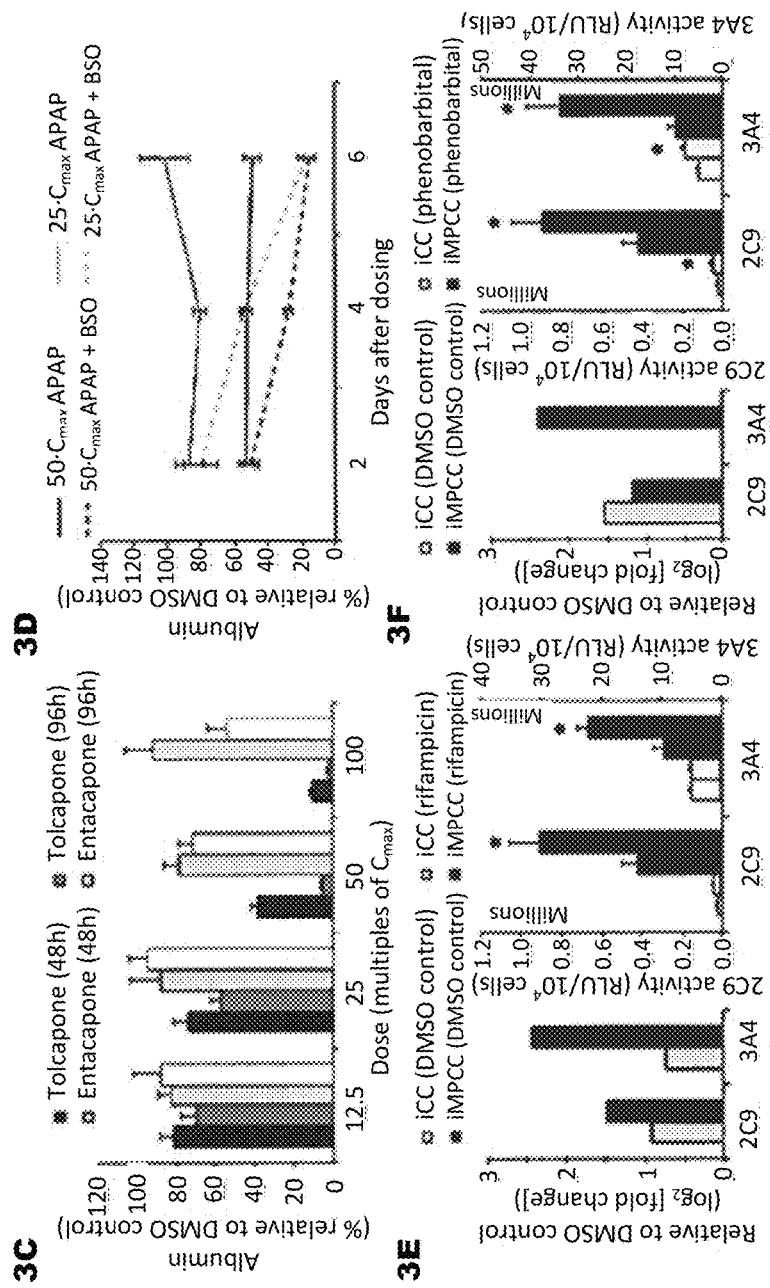
FIGURE 3C, 3D, 3E, and 3F Continued

15A

Uniformly coat TCPS with Type I Collagen → Apply PDMS Mask to Protect Collagen from Oxygen Plasma → Remove Mask and Sterilize Surface for Cell Seeding Apply a Matrigel Overlay to Create iMPCC Model ← Seed 3T3-J2 Fibroblasts and Allow Growth to Reach Contact Inhibition ← Seed iHeps and Periodically Agitate to Disperse Cells

15B

239x190mm (300 x 300 DPI)

16A
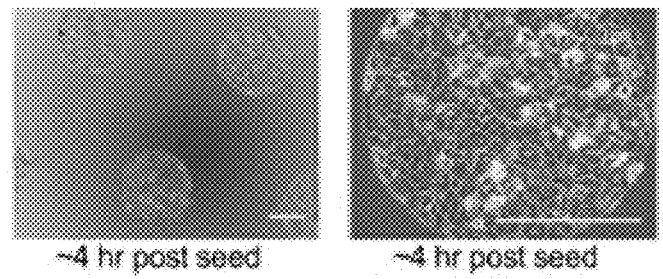
~4 hr post seed   ~4 hr post seed
16B
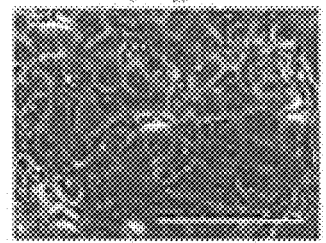
Glycogen
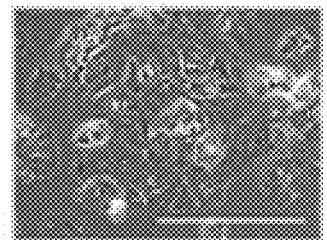
Albumin
iMPH week 1
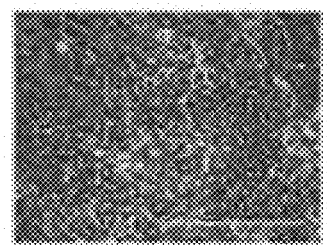
iMPH week 4
16C
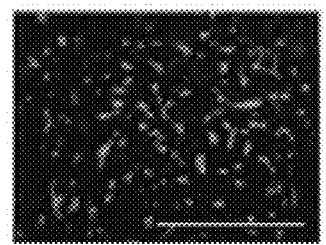
iMPCC week 1
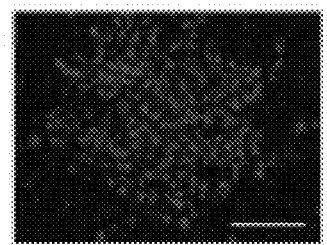
iMPCC week 4
Bile canaliculi   LDL uptake
FIGURE 16A, 16B, 16C

FIGURE 28A, 28B, and 28C

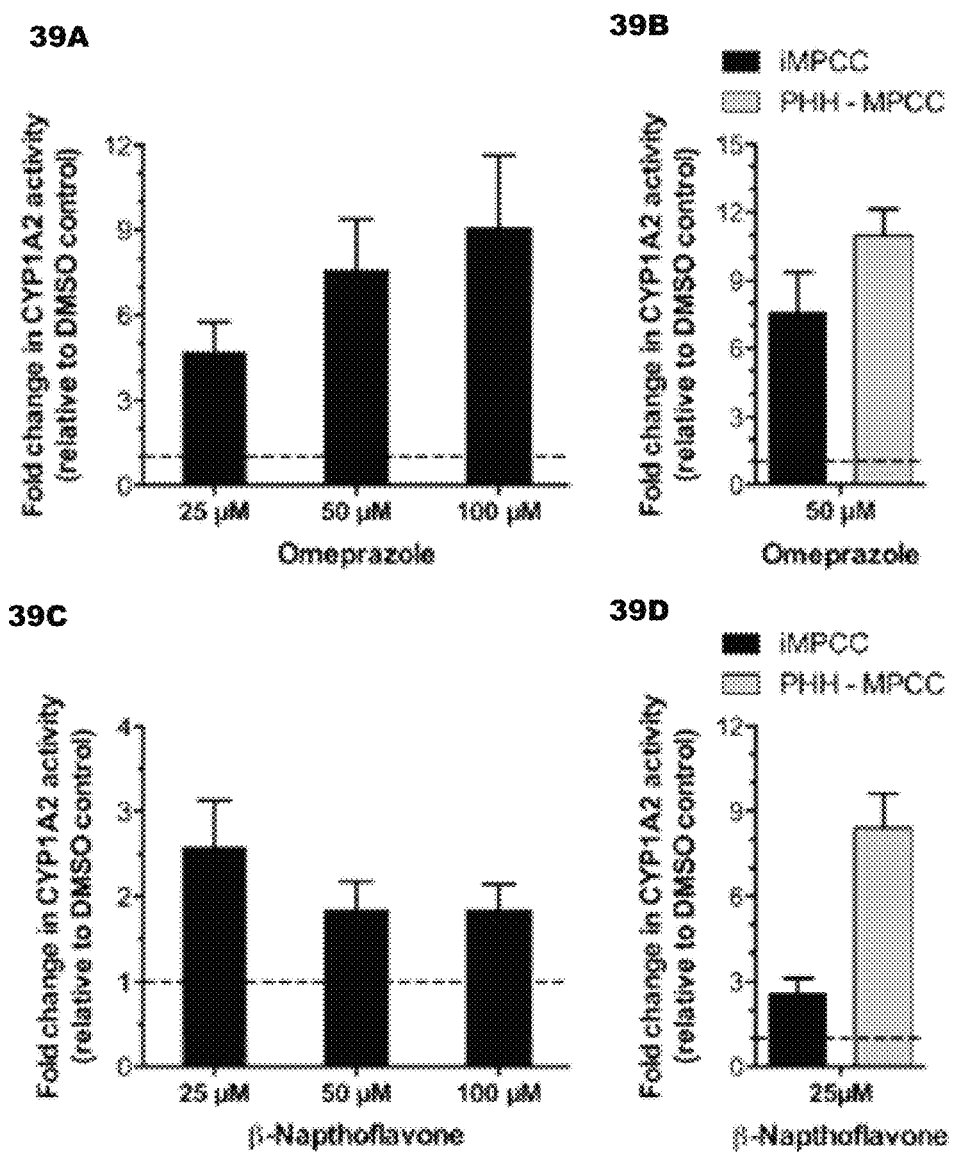
FIGURE 39A, 39B, 39C, and 39D

STEM CELL-DERIVED HEPATOCYTES IN CO-CULTURE AND USES THEREOF

CROSS-REFERENCE TO RELATED APPLICATIONS

This application claims the benefit of U.S. Provisional Patent Application No. 61/927,285 filed Jan. 14, 2014, the entire disclosure of which is incorporated herein by reference.

GOVERNMENT LICENSE RIGHTS

This invention was made with government support under CBET-1351909 awarded by the National Science Foundation. The government has certain rights in the invention.

FIELD OF THE INVENTION

The disclosure relates to in vitro cultures of human hepatic cells (hepatocytes), is and in particular to co-cultures of stem cell derived human hepatocytes with stromal cells, and use of the co-cultures in drug screening.

BACKGROUND OF THE INVENTION

Due to significant species-specific differences in liver pathways, in vitro models of the human liver play an important role in drug development and mechanistic investigations. Isolated primary human hepatocytes (PHHs) are ideal for constructing such models because they can maintain high levels of key liver functions for several weeks in vitro under specific culture conditions. However, PHHs are a severely limited resource given shortages in donor livers, and their quality for in vitro use can vary considerably across different cell lots.

Human stem cell-derived liver models, capable of assessing the hepatotoxicity of novel drugs prior to clinical implementation, have the potential to significantly reduce development costs, prevent undue morbidity, and advance personalized medicine. Hepatocyte-like cells have been produced from human induced pluripotent stem cells (iHeps) through the sequential delivery of growth factors, mirroring hepatic development. Current research indicates however that iHeps remain more fetal-like in phenotype, which substantially limits their use in toxicology screening.

Robust culture systems that can aid in discovering and screening novel drugs are needed. Such systems should exhibit: reproducible compatibility with banked cryopreserved human cells; in vivo-like and long-term (weeks) maintenance of mature hepatocyte phenotype and function; and require minimal (<10 mg) drug quantities to demonstrate a response, given limitations on manufacturing scale-up of new drug candidates.

SUMMARY OF THE INVENTION

In one aspect, the present disclosure provides a composition comprising a population of hepatocytes derived from pluripotent stem cells and at least one non-parenchymal cell population in co-culture in vitro. The composition further comprises a culture substrate, wherein the population of hepatocytes is disposed in a micropattern is on the culture substrate. The culture substrate can comprise for example a glass surface, a polystyrene surface such as a multiwell plate, or a silicon surface. The micropattern comprises a predetermined two-dimensional pattern of multiple microdots, the micropattern defined by a microdot diameter and a center-to-center spacing between each of any two neighboring microdots. Each microdot can have a diameter of about 500 µm to about 700 µm, preferably has a diameter of about 500 µm. The center-to-center spacing between each microdot can range from about 1000 µm to about 1200 µm, and is preferably about 1200 µm. In the compositions, the hepatocytes can be derived from any mammalian, including human pluripotent stem cells. The stem cells can be for example, human induced pluripotent stem cells (iPSCs), embryonic stem cells, hepatic resident stem cells, or any combination thereof. The composition, following co-culture in vitro for a period and under culture conditions sufficient to allow the hepatocytes, can maintain a higher level of differentiation toward an adult human hepatocyte phenotype when compared to hepatocytes derived from induced pluripotent stem cells and not co-cultured with at least one non-parenchymal cell population. A higher level of differentiation can be determined by measuring at least one of liver-specific gene expression, albumin secretion, urea synthesis, Phase I-II enzyme activity, LDL uptake, and number of active bile canaliculi in the co-cultured hepatocytes and comparing the measurement to that obtained in hepatocytes derived from induced pluripotent stem cells and not co-cultured with at least one non-parenchymal cell population. The compositions can further comprise a layer of material comprising at least one extracellular matrix protein, which can be disposed for example on the co-culture. The layer of material may comprises for example collagen, or any gelatinous protein mixture such as Matrigel™. In the compositions, the at least one non-parenchymal cell population can comprises stromal cells, such as for example fibroblasts, fibroblast-derived cells, macrophages, endothelial cells, stellate cells, pericytes, inflammatory cells, cholangiocytes and other types of stromal cells, and combinations thereof. The at least one non-parenchymal cell population can comprise for example embryonic fibroblasts, including murine embryonic fibroblasts, including for example 3T3-J2 murine embryonic fibroblasts. The compositions encompass a composition having been maintained in vitro for at least about 8 days, or at least about 28 to at least about 35 days. The population of hepatocytes can be derived from a population of previously cryopreserved induced pluripotent stem cell derived hepatocytes.

In another aspect, the present disclosure provides a method of culturing a population of hepatocytes derived from induced pluripotent human stem cells in vitro comprising: co-culturing the population of stem cell derived hepatocytes with at least one non-parenchymal cell population and a layer of material comprising at least one extracellular matrix protein disposed on the co-culture, and maintaining the co-culture for at least about 8 days. Co-culturing the population of stem cell derived hepatocytes with at least one non-parenchymal cell population comprises co-culturing on a culture substrate, wherein the population of stem cell derived hepatocytes are disposed in a micropattern on the culture substrate, which can be for example a glass surface, a polystyrene surface such for example a multiwell plate, or a silicon surface.

In another aspect, the present disclosure provides a method of determining the hepatotoxicity of a test compound, the method comprising: obtaining a co-culture of a population of stem cell derived hepatocytes and at least one non-parenchymal cell population in vitro and a layer of material comprising at least one extracellular matrix protein disposed on the co-culture; contacting the co-culture with the test compound; maintaining the co-culture for a time and under conditions sufficient to allow an effect of the test compound on the stem cell derived hepatocytes; and measuring at least one indicator of hepatic function in the hepatocytes to obtain a test measurement, or applying hepatocyte imaging technology (HIAT) to the hepatocytes to obtain a test image; and comparing the test measurement to a control measurement from the hepatocytes before contact with the test compound, or the test image to a control image of the hepatocytes before contact with the test compound, wherein a difference between the test and control is indicative of hepatotoxicity of the test compound. The at least one indicator of hepatic function can be, for example, albumin production, urea production, ATP production, glutathione production, liver gene expression or liver protein expression in the hepatocytes.

In another aspect, the present disclosure provides a method of determining the potential for a negative interaction of a test compound with second compound, the method comprising: obtaining a co-culture of a population of stem cell derived hepatocytes and at least one non-parenchymal cell population in vitro and a layer of material comprising at least one extracellular matrix protein disposed on the co-culture; contacting the co-culture with the test compound; maintaining the co-culture for a time and under conditions sufficient to allow induction of an inducible liver enzyme in the stem cell-derived hepatocytes; measuring at least one inducible liver enzyme level in the hepatocytes to obtain a test measurement; and comparing the test measurement to a control inducible liver enzyme measurement from the hepatocytes before contact with the test compound, wherein an increase in the test measurement relative to the control inducible liver enzyme measurement is indicative of the potential for a negative interaction of the test compound with the second compound. The at least one inducible liver enzyme can be selected for example from any inducible liver enzyme, including but not limited to a CYP enzyme such as CYP2C9 (luciferin-H), CYP3A4 (luciferin-IPA), a combination of CYP1A1, CYP1A2, CYP2B6 and CYP2D6 (luciferin ME-EGE), and any combination thereof.

In another aspect, the present disclosure provides a method of determining the hepatotoxicity of an interaction between a first test compound and a second test compound, the method comprising: obtaining a co-culture of a population of stem cell derived hepatocytes and at least one non-parenchymal cell population in vitro and a layer of material comprising at least one extracellular matrix protein disposed on the co-culture; contacting the co-culture with the first and second test compounds; maintaining the co-culture for a time and under conditions sufficient to allow an effect of an interaction the first and second test compounds on the stem cell-derived hepatocytes; and measuring at least one of albumin, urea and ATP production in the hepatocytes to obtain a test measurement, or applying hepatocyte imaging technology (HIAT) to the hepatocytes to obtain a test image; and comparing the test measurement to a control measurement from the hepatocytes before contact with the first and second test compounds, or the test image to a control image before contact with the first and second test compounds, wherein a difference between the test and control is indicative of wherein a difference between the test and control is indicative of hepatotoxicity of the interaction between the first test compound and the second test compound.

In any of the foregoing methods, the population of stem cell derived hepatocytes can be disposed in a micropattern on the culture substrate. The micropattern can comprise a predetermined two-dimensional pattern of multiple microdots, the micropattern defined by a microdot diameter and a center-to-center spacing between each of any two neighboring microdots. Each microdot can have a diameter of about 500 µm to about 700 µm, and preferably a diameter of about 500 µm. The center-to-center spacing between each microdot can be from about 1000 µm to about 1200 µm, and preferably about 1200 µm. In any of the methods, the hepatocytes can be derived from any mammalian, including human pluripotent stem cells. The stem cells can be for example, human induced pluripotent stem cells (iPSCs), embryonic stem cells, hepatic resident stem cells, or any combination thereof. In any of the methods, the at least one non-parenchymal cell population can comprise stromal cells, such as for example fibroblasts, fibroblast-derived cells, macrophages, endothelial cells, stellate cells, pericytes, inflammatory cells, cholangiocytes and other types of stromal cells, and combinations thereof. Stromal cells can comprise embryonic fibroblast, including murine embryonic fibroblasts, such as but not limited to 3T3-J2 murine embryonic fibroblasts. Any of the methods may further comprise maintaining the co-culture for at least about 8 days, or at least about 28 days to at least about 35 days.

In another aspect, the present disclosure provides a composition as disclosed herein, further comprising a culture medium comprising: a base of Dulbecco's modified Eagle's medium (DMEM), combined with about 0.5% to about 10% (vol:vol) bovine serum, an insulin-transferrin-selenium (ITS) mixture at about a dilution of about 1:50 to about 1:200, about 0.05 µM to about 1.0 µM dexamethasone, about 0.5 ng/mL to about 20 ng/mL of at least one interleukin-6 cytokine, about 0.5 ng/mL to about 10 ng/mL glucagon, and a B-27® supplement diluted to 1×, or about 1% to about 5%. The medium can further contain about 1% (vol:vol) penicillin/streptomycin, and a buffer, is such as HEPES at about 1.5%. The culture medium can contain, for example, about 1%, about 2%, about 3%, about 4%, about 5%, about 6%, about 7%, about 8%, or about 9% (vol:vol) bovine (e.g., fetal calf) serum. The ITS mixture can be any ITS or ITS+ mixture, such as for example insulin-transferrin-selenium-selenous acid. The culture medium can contain the ITS mixture at a dilution of about 1:75, 1:100, 1:125, or 1:150. The culture medium can contain, for example, about 0.1 µM, about 0.2 µM, about 0.3 µM, about 0.4 µM or about 0.5 µM dexamethasone. In the culture medium, the interleukin-6 cytokine can be for example any one of IL-6, IL-11, IL-31, cardiotrophin-1 (CT-1), ciliary neurotrophic factor (CNTF), cardiotrophin-like cytokine (CLC), neuropoietin (NP), leptin, leukemia inhibitory factor (LIF), oncostatin M, or any combination thereof. The culture medium can contain, for example, about 1.0 ng/mL, about 1.5 ng/mL, about 2.0 ng/mL, about 2.5 ng/mL, about 3.0 ng/mL, about 3.5 ng/mL, about 4.0 ng/mL, or about 4.5 ng/mL, of the at least one interleukin-6 family cytokine. The culture medium can contain, for example, about 1.0 ng/mL, about 2.0 ng/mL, about 3.0 ng/mL, about 4.0 ng/mL, about 5.0 ng/mL, about 6.0 ng/mL, about 7.0 ng/mL, about 8.0 ng/mL, or about 9.0 ng/mL glucagon.

BRIEF DESCRIPTION OF THE DRAWINGS

The application file contains at least one drawing executed in color. Copies of this patent application publication with color drawings(s) will be provided by the Office upon request and payment of the necessary fee.

1A Stable morphology of iHeps in iMPCC model over time in culture. Morphology of iHeps in a micropatterned pure culture (iMPH) model is shown for comparison. Scale bars, 250 µm. FIG. 1B Functional bile canaliculi transporter activity in iMPCCs as assessed by the internalization, processing and excretion of 5-(and-6)-carboxy-2',7'-dichlorofluorescein diacetate. Uptake of low-density lipoproteins was assessed by incubation with DiL-LDL. Scale bars, 250 µm. FIG. 1C Rates of albumin synthesis and urea secretion in iMPCC, iMPH and conventional confluent monolayer culture (iCC) models over 4 weeks. All error bars represent s.d. (n=3).

FIG. 2A Quantitative comparison of liver-specific mRNA from iMPCC and iCC models to mRNA from freshly obtained iHeps in suspension (day 0). All data was normalized to the reference gene, GAPDH, glyceraldehyde-3-phosphate dehydrogenase. A1AT (SERPINA10), α-antitrypsin, ALB, albumin, ARG1, arginase 1, GCR (NR3C1), glucocorticoid receptor, HNF4a, hepatocyte nuclear factor 4a, HNF6 (ONECUT1), hepatocyte nuclear factor 6, OATP2 (SLCO1B1), solute carrier organic anion transporter family, member 1B1, TAT, tyrosine aminotransferase, and TDO2, tryptophan 2,3-dioxygenase. FIG. 2B Quantitative comparison as in (a), except that genes for different CYP isozymes are displayed. FIG. 2C CYP enzyme activity levels in iMPCCs over time assessed using luminescence-based assays. Two specific substrates to CYP2C9 and CYP3A4 were used in addition to a substrate measuring the 'combined' activity of CYPs 1A1, 1A2, 2B6 and 2D6. FIG. 2D CYP enzyme activity levels using conventional substrates in iMPCCs (day 16). Data was normalized to MPCC stabilized primary human hepatocytes. Substrates to assess CYP activity are as follows: 1A2 phenacetin (100 µM); 2A6 coumarin (50 µM); 2B6 bupropion HCl (500 µM); 2C8 paclitaxel (30 µM); 2C9 tolbutamide (50 µM); 2C19 s-mephenytoin (100 µM); 2D6 dextromethorphan (16 µM); and 3A4 testosterone (200 µM). All error bars represent s.d. (n=3).

FIGS. 3A, 3B, 3C, 3D, 3E, and 3F Utility of iMPCC model for screening of drug toxicity and drug interactions. FIG. 3A Rank ordering of true positive compounds by albumin TC50 values, defined as the drug concentration which reduces the albumin secretions to 50% of DMSO-only controls. Arrows indicate a measurable TC50 (below $100 \cdot C_{max}$) while missing bars indicate a TC50 above $100 \cdot C_{max}$. FIG. 3B Rank ordering of false negative compounds detected in the iMPCC model. FIG. 3C Time- and dose-dependent albumin secretions with tolcapone (withdrawn by FDA) and its structural analog entacapone (FDA approved). Data were normalized to DMSO-only controls. FIG. 3D Time- and dose-dependent albumin secretions of cultures dosed with acetaminophen (APAP) and with or without the glutathione depleting agent L-buthionine (S,R)-sulfoximine (BSO). FIG. 3E Rifampicin (25 µM) mediated induction of CYP2C9 and CYP3A4 gene expression and functional activity in iMPCCs. Cultures were treated with inducers for 4d before incubation with CYP-specific luminescence-based substrates (day 22). The effect of rifampicin induction in iCCs is shown for comparison. FIG. 3F Same as in FIG. 3E, except phenobarbital (1 mM) was used as the clinical inducer. Data were normalized to DMSO-only vehicle controls. All error bars represent s.d. (n=3). * p<0.05.

FIG. 6A CYP enzyme activity levels in a micropatterned pure iHep (iMPH) model over time assessed using luminescent based assays. Two specific substrates to CYP2C9 and CYP3A4 were used in addition to a substrate measuring the 'combined' activity of CYPs 1A1, 1A2, 2B6 and 2D6. FIG. 6B Same as in FIG. 6A, except CYP activities were measured from a conventional confluent monolayer of iHeps (iCC). Data from representative study shown. All error bars represent s.d. (n=3).

FIG. 12A Bar graph of gene expression ration of CYP3A4 to CYP3A7 in suspension iHeps, iCCs, and iMPCCs. FIG. 12B Bar graph of ratio of ALB to AFP protein levels in iMPCCs.

FIG. 15A Collagen is simultaneously micropatterned within standard tissue culture polystyrene (TCPS) wells using PDMS mask-based soft-lithography. iHeps attach selectively onto the collagen domains, followed by seeding of 3T3-J2 fibroblasts in the surrounding areas within 24 hours. Addition of an extracellular matrix overlay (i.e. Matrigel™) 2 days after fibroblast seeding establishes iMPCCs. FIG. 15B Left: image of a 24-well tissue culture polystyrene plate with hepatocyte islands stained purple using the MTT [3-(4,5-dimethylthiazol-2-yl)-2,5-diphenyltetrazolium bromide] dye. Right: image of 4 wells with MTT stained hepatocyte islands. Similar patterning can be obtained in a 96-well plate format (images not shown).

FIGS. 16A, 16B and 16C Characterization of iHep morphology and polarity. FIG. 16A Phase contrast images of iHeps attached to collagen domains at different magnifications (4 hours post seeding). Glycogen and albumin staining in the iHep islands within 2 days of seeding. FIG. 16B Phase contrast images of iHeps in micropatterned formats 1 and 4 weeks after culturing either without fibroblasts (iMPHs: micropatterned pure iHep cultures) or with fibroblasts (iMPCCs). FIG. 16C Functional bile canaliculi in iMPCCs as assessed by the excretion of CDF [5-(and-6)-carboxy-2',7'-dichlorofluorescein diacetate] into the bile canaliculi between iHeps. Uptake of fluorescent low-density lipoproteins (DiI-LDL) in iHep cytoplasm in iMPCCs. Images from 1-week-old cultures are shown. All scale bars are 250 µm.

FIG. 17A Quantitative comparison of liver mRNA transcripts in iMPCCs and iCCs (conventional confluent cultures of iHeps with Matrigel™ overlay) to transcripts in fresh iHeps in suspension prior to seeding (line $2^0$). All data were normalized to GAPDH (glyceraldehyde-3-phosphate dehydrogenase). ALB (albumin); ARG1 (arginase 1); HNF4α (hepatocyte nuclear factor 4α); NR3C1 (GCR, glucocorticoid receptor); ONECUT1 (HNF6, hepatocyte nuclear factor 6); SERPINA10 (A1AT, α1-antitrypsin); SLCO1B1 (OATP2, solute carrier organic anion transporter family, member 1B1); TAT (tyrosine aminotransferase); TDO2 (tryptophan 2,3-dioxygenase); and, CYP450 (cytochrome P450). FIG. 17B Rate of albumin and urea secretion in iMPCC, iMPH, and iCC models over 4 weeks.

FIGS. 18A-18C Time-course of CYP450 enzyme activities in iMPCCs and iMPHs. Non-specific CYP450 (contribution from CYP1A1, 1A2, 2B6, 2D6), CYP2C9 and CYP3A4 activities were assessed using luminescent assays (Promega). FIG. 18D Time-course of coupled phase-I and phase-II enzyme activity in iMPCCs and iMPHs. Coumarin is converted to 7-hydroxycoumarin (7-HC) by CYP2A6 followed by conjugation with sulfate group (7-HC-sulfate) by phase-II enzymes.

FIGS. 19A and 19B iMPCCs and iCCs were treated with rifampicin (RIF) or phenobarbital (PB) for 4 days followed by quantitation of CYP3A4 and CYP2C9 gene expression on day 22 of culture. Gene expression was normalized to DMSO-only vehicle controls (dotted line at value of 1). FIG. 19C Nuclear receptor gene expression in iMPCCs relative to iCCs (dotted line at value of 1) on day 22 of cultures, normalized to GAPDH (glyceraldehyde-3-phosphate dehydrogenase). CAR (constitutive androstane receptor); PXR (pregnane X receptor). FIGS. 19D-19E iMPCCs and iCCs were treated with drugs as described above followed by assessment of CYP450 activities using luminescent substrates on day 22 of culture. *p<0.05.

FIG. 20A Correlation of global gene expression profiles (Affymetrix whole genome microarrays) in iMPCCs after 9 and 21 days of culture. FIG. 20B Correlation of global gene expression profiles in iMPCCs and freshly isolated PHHs. FIG. 20C Correlation of global gene expression profiles in iMPCCs and PHH-MPCCs (same donors as in panel 'b'). FIGS. 20D-20E Quantitative comparison of liver-specific transcripts in iMPCCs and PHH-MPCCs normalized to freshly isolated PHHs (dotted line at value of $2^0$ or 1). The data for PHHs is averaged across two donors and was obtained from a previously published study (6). PHH-MPCCs were cultured for 42 days for donor 1 and 6 days for donor 2 with hepatic functions stabilized during this timeframe. Gene expression levels in iMPCCs ranged from 0.5- to 2-fold (panel 'd') and from 0.1- to 0.5-fold (panel 'e') as compared to fresh PHH levels. Phase-I enzymes (Ph. I), phase-II enzymes (Ph. II), transporters (TP), transcription factors (TF), nuclear receptors (NR), and other liver-specific genes (*).

FIG. 21A Liver functions in iMPCCs, PHH-MPCCs and 24-hour PHH conventional cultures, normalized to PHH on day of seeding (day 0, dotted line at value of 100). Data from 2 PHH donors is averaged. Non-specific CYP450 substrate (N.S.); glucuronidation (Gluc.); and sulfation (Sulf.). FIG. 21B Drug-mediated induction of CYP2C9 and CYP3A4 transcripts in iMPCCs and PHH-MPCCs (2 donor average). Cultures were treated with rifampicin (RIF) or phenobarbital (PB) for 4 days followed by RNA extraction. Data was normalized to transcript expression measured in DMSO-only treated cultures (dotted line at value of 1). FIG. 21C Same experiment as in panel 'b' except CYP450 activities were measured following drug treatment.

FIG. 22A Albumin and urea secretion in iMPCCs following treatment for 8 days with multiple doses of prototypical hepatotoxins. $C_{max}$ represents the maximum blood concentration observed in human plasma for a given drug (21,40). FIG. 22B Same experimental design as in panel 'A' except iMPCCs were dosed with non-liver-toxins.

FIGS. 30A and 20B Prolonged in vitro culture of cryopreserved iHeps. FIG. 30A Albumin secretion and FIG. 30B CYP3A4 enzyme activity (luciferin-IPA substrate from Promega) in iMPCCs relative to conventional confluent cultures with Matrigel™ overlay (iCCs). All error bars represent standard deviation (n=3). The donor used for this experiment was iPSC donor #1 (see methods).

FIG. 31A Albumin and urea secretion and FIG. 31B CYP3A4 enzyme activity (luciferin-IPA substrate from Promega) in iMPCCs over time. The donor used to collect this data is iPSC donor #2 (see methods). All error bars represent standard deviation (n=3).

FIG. 33A Scatter plot comparing gene expression profiles (Affymetrix whole genome human microarray) in two donors of freshly isolated PHHs in order to demonstrate donor-to-donor variability. Data was acquired from a previous publication (1). FIG. 33B Scatter plot comparing gene expression intensities in iMPCCs to expression intensities in PHH donor 1 of freshly isolated PHHs. FIGS. 33C-33D Similar to panel 'b' but comparisons between iMPCCs (two time-points in culture, days 9 and 21) and PHH donor 2 is shown.

FIG. 14: CellNet gene regulatory network (GRN) establishment scores from iMPCCs, freshly isolated primary human hepatocytes (PHHs) and PHH-MPCCs. Liver GRN scores represent the extent to which gene regulatory networks are established in a given set of samples as compared to liver-specific training data. Liver GRN scores for iMPCCs (0.959 for day 9 and 0.925 for day 21) fall between the scores provided for freshly isolated (0.978 for PHH donor 1 and 0.848 for PHH donor 2) and PHH-MPCCs (0.924 for PHH donor 1 and 1.005 for PHH donor 2). More details for the CellNet analysis schemes are provided in (2).

FIG. 37B iMPCC transcripts with less than 10% of PHH levels. Ph. 1, phase I enzymes; Ph. II, phase II enzymes; TP, transporter proteins; NR, nuclear receptors; *, other liver-specific genes. All PHH gene expression levels (freshly isolated and PHH-MPCC) are the average of two donors.

FIGS. 39A, 39B, 39C, and 39D CYP1A2 induction in iMPCCs and PHH-MPCCs via omeprazole and β-naphthoflavone. FIG. 39A Functionally stable iMPCCs were treated with omeprazole (25, 50 and 100 μM) for 4 days followed by quantitation of CYP1A2 activity though the 1A2-mediated O-dealkylation of 7-ethoxyresorufin into fluorometric resorufin. FIG. 39B PHH-MPCCs were tested in a similar manner as described in panel 'a', but at a single dose of omeprazole (50 μM). Induction levels in PHH-MPCCs were compared to those obtained in iMPCCs at the same dose administered for the same time duration. (FIGS. 39C-39D) Same as in panels 'a' and 'b', but iMPCCs and PHH-MPCCs were treated with β-naphthoflavone as a CYP1A2 inducer. All error bars represent standard deviation (n=3).

DETAILED DESCRIPTION OF THE DISCLOSURE

Figures 1A, 1B, 1C:
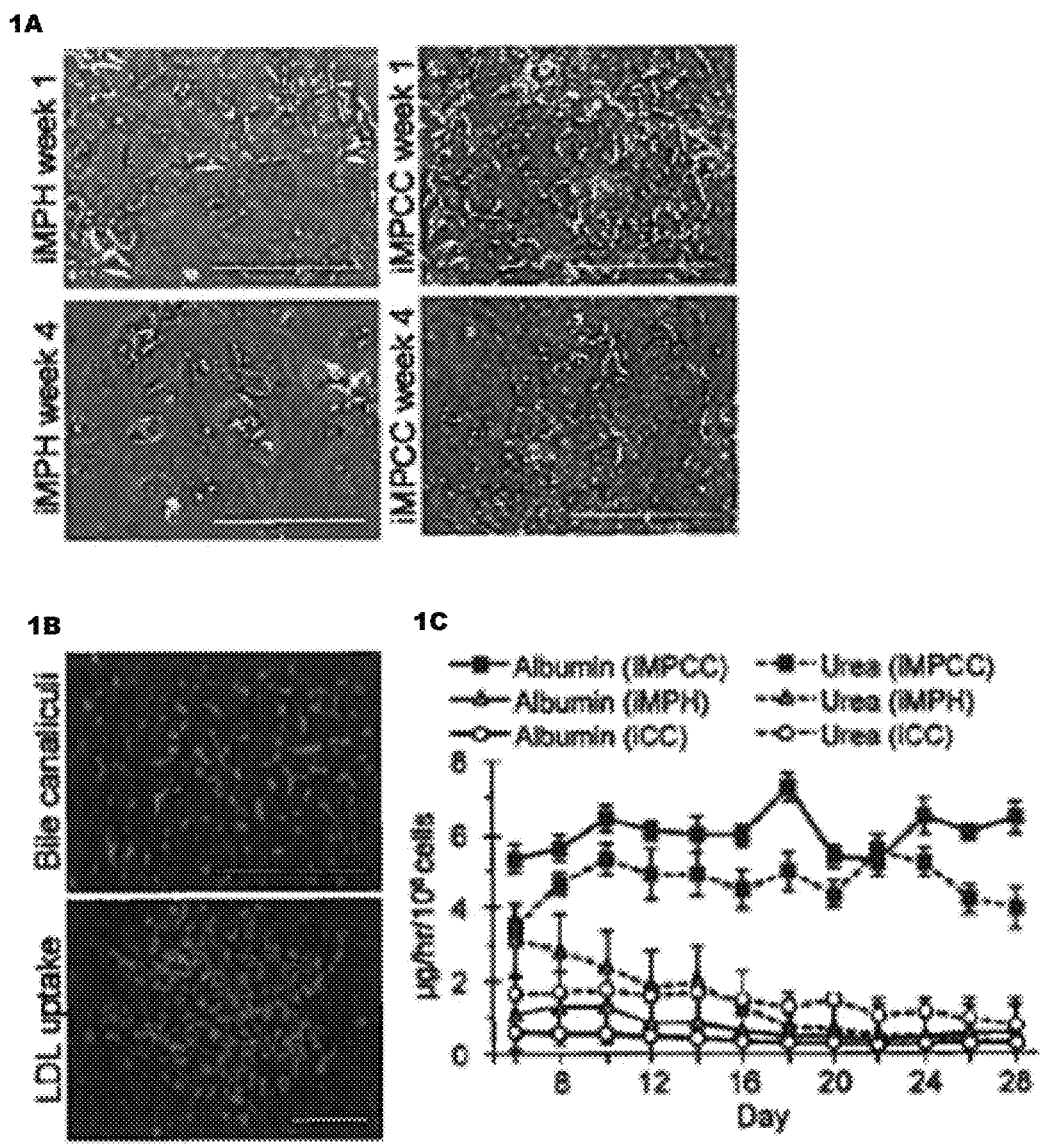
FIGS. 1A, 1B and 1C are a series of photomicrographs and a graph showing morphological and functional stability of an iHep micropatterned co-culture (iMPCC) model. FIG.

The present disclosure describes compositions and methods based in part on the surprising finding that stem cell derived human hepatocytes, when maintained in micropatterned co-culture with non-parenchymal cells, such as for example fibroblast or fibroblast-derived cells, exhibit a more stable adult human hepatocyte phenotype than the same stem cell derived human hepatocytes cells maintained under conventional culture conditions, which remain more fetal-like in phenotype, thus limiting their use in toxicology. Additionally, the hepatocytes in co-culture remain viable for extended periods relative to hepatocytes maintained in conventional (mono) culture, while at the same time also appearing to maintain adult phenotype for a period of at least about 8 days and at least as long as about 28 days to about 35 days.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms as used herein and in the claims shall include pluralities and plural terms shall include the singular. For example, reference to "a cellular island" includes a plurality of such cellular islands and reference to "the cell" includes reference to one or more cells known to those skilled in the art, and so forth.

The use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated. Enzymatic and staining reactions, and purification techniques are performed according to manufacturer's specifications and protocols, as commonly accomplished in the art or as described herein. The nomenclatures used in connection with, and the laboratory procedures and techniques of, analytical chemistry, synthetic organic chemistry, and medicinal and pharmaceutical chemistry described herein are also those well-known and commonly used in the art. Standard techniques are used for chemical syntheses, chemical analyses, pharmaceutical preparation, formulation, and delivery, and treatment of all subjects, human and animal.

As used herein, the term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig). Preferably, the subject is a human.

The term "treatment" as used herein, is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

The term "donor" includes human and other mammalian subjects from which cells such as stem cells and/or primary hepatocytes may be obtained.

The term "patient" includes human and other mammalian subjects that receive either prophylactic or therapeutic treatment.

That the present disclosure may be more readily understood, select terms and phrases as used herein are defined below.

A. Co-cultures of Induced Pluripotent Stem Cell Derived Hepatocytes

The present disclosure encompasses a composition comprising a population of mammalian stem cell derived hepatocytes and at least one non-parenchymal cell population in co-culture. The co-cultures as described herein provide a useful in vitro liver model and thus also provides a unique platform for the development and toxicology screening of therapeutic agents, including high-throughput screening of drug candidates for efficacy and toxicity. The co-cultures described herein include but are not limited to co-cultures that are a hybrid of ECM overlay ("sandwich") cultures and micropatterned co-cultures ("MPCCs"). Co-culturing methods and techniques have been described in detail in the literature, and in particular MPCC co-culturing materials, methods and techniques are described in detail in Khetani and Bhatia, Nature Biotechnology, 2008, 26(1):120-126, and in US 2006-0270032 A1, the entire disclosures of which are incorporated herein by reference. The presently disclosed MPCCs comprising hybrid cultures including an ECM overlay of hepatocytes derived from induced pluripotent stem cells are referred to herein as iMPCCs.

The parenchymal cells used in the co-cultures are human hepatocytes derived from any mammalian pluripotent stem cells, for example human induced pluripotent stem cells (iPSC's), embryonic stem cells (ESC's), hepatic resident stem cells (oval cells), and the like. A non-limiting, exemplary co-culture is one which includes hepatocytes derived from human induced pluripotent stem cells such as iCell® Hepatocytes ("iHep" or "iHeps") available from Cellular Dynamics International of Madison, Wis. The non-parenchymal cells are may be human or non-human, and are preferably fibroblast or fibroblast-derived cells. At least one of the non-parenchymal cell populations may comprise stromal cells, such as but not limited to fibroblasts, fibroblast-derived cells, macrophages, endothelial cells, stellate cells, pericytes, inflammatory cells, cholangiocytes and other types of stromal cells, and combinations thereof. Fibroblasts may be for example mammalian fibroblasts, such as for murine embryonic fibroblasts. Non-limiting, exemplary fibroblasts are 3T3-J2 murine embryonic fibroblasts. Human non-parenchymal cells from normal and diseased patients can also be used. For instance, it can be useful to use stellate cells in the liver, which are known to cause fibrosis, to provide an in vitro model for fibrosis. It is contemplated that other non-parenchymal cells, both liver and non-liver, and non-parenchymal cells specifically implicated in a disease can be used to provide an in vitro model for drug testing new drugs to treat the disease.

Additionally, the present disclosure contemplates that hepatocytes derived from induced pluripotent stem cells obtained from an individual donor can be cultured with disease causing non-parenchymal cells (e.g., stellate cells) obtained from the same individual donor. Non-parenchymal cells such as endothelial cells can also be derived from iPSCs (e.g., iEndothelial, iMacrophage and the like). Non-parenchymal cells such as endothelial cells can also be derived for example from the same individual donor via an iPSC intermediary. The resulting co-culture can be used to screen optimal drug formulations to treat the disease (e.g., fibrosis) and resulting hepatic dysfunction in the individual donor. iHep colonies can be surrounded with different stromal cell populations to create stem cell-derived liver models enabling controlled investigations of specific heterotypic interactions on hepatic functionality and maturation. For example, a combination of human mesenchymal stem cells and endothelial cells may also provide a supportive stromal environment. Additionally, small molecules for iHep maturation can also be applied in the co-cultures described herein model. Small molecule iHep maturation factors can be any from among those described in the literature and as known to those of skill in the art, including for example any of the small molecules described in Shan et al., NATURE CHEM BIOL. 9(8): 514-20 (2013), the entire disclosure of which is herein incorporated by reference.

The co-cultures are established on substrate, which may comprise a glass or elastomeric structure with a suitable culture surface, such as a glass, polystyrene, or silicon slide, or polystyrene microwells. The co-cultures described herein are established according to a micropattern established on the culture surface. The micropattern may comprise for example a predetermined two-dimensional pattern of multiple microdots ("islands") of the hepatocytes, wherein each microdot has approximately the same microdot diameter and each of any two neighboring microdots shares approximately the same edge-to-edge spacing. While the microdot diameters and microdot spacing may be varied and do vary for cultures with different cell types, it has been found that for stem-cell derived hepatocytes, a preferred micropattern is characterized by microdots each having a diameter of about 500 µm to about 700 µm, and a center-to-center spacing between each microdot of at least about 1000 µm to at least about 1200 µm, including at least about 1100 µm, and preferably a micropattern characterized by microdots each having a diameter of about 500 µm, and an edge-to-edge spacing between each microdot of at least about 1200 µm. A micropattern having the foregoing characteristics has been found to result in co-cultures of stem cell derived hepatocytes that remain viable and show evidence of mature phenotype retention for several days and weeks, including up to at least about 8 days, at least about 28 days, and at least 35 days.

To establish the micropattern, a cell adhesion molecule may be applied to the culture substrate at the microdots, using for example a PDMS stencil. The cell adhesion molecule is any molecule to which the stem cell derived hepatocytes selectively adhere relative to inter-microdot space, such as collagen, fibronectin, vitronectin, laminin, extracellular matrix proteins, Arg-Gly-Asp (RGD) peptide, Tyr-Ile-Gly-Ser-Arg (YIGSR) peptide, glycosaminoglycans, hyaluronic acid, integrins, ICAMs, selectins, cadherins, cell surface protein-specific antibodies, any combination thereof, and any composition composed substantially of purified extracellular matrix protein, or mixtures of extracellular matrix proteins. Suitable extracellular matrix can be provided for example by ECM derived directly from mammalian liver, such as porcine or human liver. In one micropatterned stem cell derived hepatocyte co-culture, the cell adhesion molecule is for example any of the many extracellular matrix protein products available from a variety of commercial suppliers. In another micropatterned stem cell derived hepatocyte co-culture, the cell adhesion molecule is for example a commercially available collagen, such as rat tail collagen.

Following seeding of the hepatocytes onto the micropattern, the non-parenchymal cell population may be seeded onto the culture surface to occupy the inter-microdot space which is not occupied by the hepatocytes.

A biopolymer scaffold may optionally be disposed on the culture substrate to further support and promote cell viability. Biopolymers suitable as scaffold material include but are not limited to alginate, chitosan, hyaluronate, fibrous proteins, collagen, silk and elastin and gelatinous protein mixtures. It has also been found that the addition of a Matrigel™ (Corning Life Sciences) layer over the iMPCC's, as has been used in primary hepatocyte cultures, increased albumin production and CYP3A4 activity in co-cultured stem cell derived hepatocytes. Matrigel™ is a commercially available gelatinous protein mixture secreted by Engelbreth-Holm-Swarm (EHS) mouse sarcoma cells. It should be understood that any gelatinous protein mixture that mimics the extracellular environment found in biological tissues can also be used as the overlay.

The co-cultures described herein can be prepared using a culture medium starting with an Eagle's minimal essential medium (EMEM), and preferably a base of Dulbecco's modified Eagle's medium (DMEM) supplemented with about 0.5% to about 10% (vol:vol) bovine (e.g., fetal calf) serum; an insulin-transferrin-selenium (ITS) mixture at about a dilution of about 1:50 to about 1:200; about 0.05 µM to about 1.0 µM dexamethasone; about 0.5 ng/mL to about 20 ng/mL of at least one interleukin-6 cytokine; about 0.5 ng/mL to about 10 ng/mL glucagon; and a B-27® supplement diluted to 1×, or about 1% to about 5%. The medium can further contain about 1% (vol:vol) of an antibiotic or antibiotic mixture, such as penicillin/streptomycin, and a physiological buffering agent, such as HEPES buffer, at about 1.5%. For example, the culture medium can contain, for example, about 1%, about 2%, about 3%, about 4%, about 5%, about 6%, about 7%, about 8%, or about 9% (vol:vol) bovine (e.g., fetal calf) serum. The ITS mixture can be any ITS or ITS+ mixture as known in the art, such as for example insulin-transferrin-selenium-selenous acid. The culture medium can contain the ITS mixture at a dilution of about 1:75, 1:100, 1:125, or 1:150. The culture medium can contain, for example, about 0.1 µM, about 0.2 µM, about 0.3 µM, about 0.4 µM or about 0.5 µM dexamethasone. The interleukin-6 cytokine can be for example any one of IL-6, IL-11, IL-31, cardiotrophin-1 (CT-1), ciliary neurotrophic factor (CNTF), cardiotrophin-like cytokine (CLC), neuropoietin (NP), leptin, leukemia inhibitory factor (LIF), oncostatin M, or any combination thereof. The culture medium can contain, for example, about 1.0 ng/mL, about 1.5 ng/mL, about 2.0 ng/mL, about 2.5 ng/mL, about 3.0 ng/mL, about 3.5 ng/mL, about 4.0 ng/mL, or about 4.5 ng/mL, and so on up to about 20 ng/mL of the at least one interleukin-6 family cytokine. The culture medium can contain, for example, about 1.0 ng/mL, about 2.0 ng/mL, about 3.0 ng/mL, about 4.0 ng/mL, about 5.0 ng/mL, about 6.0 ng/mL, about 7.0 ng/mL, about 8.0 ng/mL, or about 9.0 ng/mL glucagon. A culture medium may comprise for example a DMEM base supplemented with about 1% bovine serum (vol:vol); about 1% (vol:vol) an ITS+ mixture; 0.1 µM dexamethasone; about 2.5 ng/mL oncostatin M; a B-27® supplement at about 2%; about 7 ng/mL glucagon; about 1% penicillin/streptomycin; and about 1.5% HEPES buffer.

The present disclosure also provides a kit for use according to the drug screening methods as described herein below. A kit may comprise for example: a population of stem cell derived hepatocytes and at least one non-parenchymal cell population for preparing one or more iMPCC's as disclosed herein. The kit may further comprise a culture medium as described herein, and/or additional materials or reagents for testing various biological activities of the cells in culture. For example, the kit may contain separately packaged amounts of a glucose-free medium, pyruvate, lactate, glucose, insulin, glucagon, dexamethasone, metformin, a stain or dye such as but not limited to a fluorometric dye, a lipid dye such as Nile red, and/or a cellular stain for glycogen such as PAS stain. The kit may further comprise one or more culture substrates such as a glass, silicon, or polystyrene slide or culture well, and an amount of a cell adhesion molecule. The cell adhesion molecule may be disposed according to a micropattern on the culture substrate as described herein above. Alternatively the kit may provide an amount of the cell adhesion molecule and a PDMS stencil which can be used together to establish a micropattern as described herein on the culture substrate.

The kit may further comprise a reporter molecule or label capable of generating a signal indicative of a level of a cellular activity of interest in the hepatocytes, such as but not limited a vital dye, a lipid dye, a colorimetric agent, or a bioluminescent marker. The kit may include a detectable label such as a fluorophore, a radioactive moiety, an enzyme, a chromophore, a chemiluminescent label, or the like, and/or reagents for carrying out detectable labeling. The labels and/or reporter molecules, any calibrators and/or controls can be provided in separate containers or pre-dispensed into an appropriate assay format, for example, into microtiter plates.

It is contemplated for example that one or more of the presently disclosed co-cultures can be provided in the form of a kit with one or more containers such as vials or bottles, with each container containing a separate population of cells and/or reagents and washing reagents employed in an assay. The kit can comprise at least one container for conducting the assay, and/or a buffer, such as an assay buffer or a wash buffer, either one of which can be provided as a concentrated solution, a substrate solution for the detectable or a stop solution. Preferably, the kit comprises all components, i.e., reagents, standards, buffers, diluents, etc., which are necessary to perform the assay. The kit may contain instructions for determining the presence or amount of any metabolite, biomarker, label or reporter of interest in the co-culture, in paper form or computer-readable form, such as a disk, CD, DVD, or the like, and/or may be made available online.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme cofactors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

B. Uses of Micro-patterned Co-cultures of Primary Human Hepatocytes

The present disclosure encompasses various methods of using the hepatocyte co-cultures described herein. For example, the present disclosure provides a method for preserving the phenotype of a population of stem cell derived hepatocytes in vitro following preparation and culture of the stem cells in vitro. The method may comprise stabilizing a mature hepatocyte phenotype of stem cell derived hepatocytes in co-culture for at least about 8 days, or at least about 28 days to at least about 35 days. Stem cell derived hepatocytes may be derived from stem cells donated from one or more human donors suffering from a disease or disorder of the liver, and the methods encompass preparing iMPCCs as described herein using such stem cells, and preserving the phenotype of such hepatocytes in co-culture for at least about 8 days, or at least about 28 days to at least about 35 days. Maintenance of the diseased or disordered phenotype may be identified using any of the methods disclosed herein or as known in the art.

Micro-patterned co-cultures of pluripotent stem cell derived hepatocytes as described herein may be further used in various methods, such as but not limited to drug discovery and drug screening. For example, such co-culture systems can be used to develop and screen drug candidates for treating any hepatic disease or disorder, or for screening the hepatotoxicity of drug candidates for treating any other disease or disorder. For example, iMPCCs as described herein show superiority over conventional culture models and perform comparably with co-culture stabilized primary human hepatocytes for the in vitro prediction of drug induced liver toxicity, and establish a new direction in in vitro models of the liver.

A candidate therapeutic agent may be a small molecule, a peptide, a polypeptide, an oligonucleotide, a polynucleotide, or an antibody.

Any of the methods may involve determining a baseline or control value, for example, of any indicator of liver function such as gluconeogenesis, glycolysis, glycogen storage, enzyme activity, albumin secretion, urea production, gene expression, inducible liver enzyme activity and the like, in the hepatocytes in co-culture before administering a dosage of a candidate therapeutic agent or other test agent, and comparing this with a value or level after the exposure and noting any significant change (i.e., greater than the typical margin of experimental error in repeat measurements of the same sample, expressed as one standard deviation from the mean of such measurements) over the control. In non-limiting example, at least one is indicator of hepatic function can be a measure of albumin production, urea production, ATP production, glutathione production, liver gene expression, liver protein expression or inducible liver enzyme activity in the hepatocytes.

Screening Assays

The present disclosure provides micro-patterned co-cultures of pluripotent stem cell derived hepatocytes which induce phenotypic stability in the hepatocytes for several weeks. The micropatterned co-cultures can be utilized in various methods for identifying and screening of potential therapeutic agents, and for drug development. For example, the compositions of the present disclosure may be used in vitro to screen a wide variety of compounds, such as small molecules, antibodies, peptides, polypeptides, nucleic acid-based agents and the like, to identify therapeutic agents having a therapeutic effect on liver function in any disease or disorder of the liver, and/or to assess the hepatotoxicity of any such therapeutic agent before clinical implementation, For example, following contact of a micropatterned co-culture with a candidate therapeutic agent, various cellular functions in the hepatocytes may be assessed by examining gene expression, albumin production, urea production, cytochrome P450 (CYP) metabolic activity or any inducible liver enzyme activity, uptake and secretion of liver-specific products, and response to hepatotoxins, by detecting and/or measuring level of a protein, metabolite, reporter molecule, label, or gene expression level such as through gene fluorescence in the cell or in the culture media. In non-limiting example, at least one indicator of hepatic function can be, for example, albumin production, urea production, ATP production, glutathione production, liver gene expression or liver protein expression in the hepatocytes.

For example, gluconeogenesis and other liver functions such as albumin secretion, urea production, glycolysis and glycogen storage may be monitored in the presence and absence of one or more stimuli, test agent or candidate therapeutic agent. For example, stem cell derived hepatocytes in co-culture as described herein may be tested for any one or more of albumin secretion, urea production, ATP production, induction of inducible liver (e.g., CYP) enzyme levels, gluconeogenesis, glycolysis and glycogen storage in the presence and absence of varying levels of candidate therapeutic agents. In any method involving measurement of one or more inducible liver enzymes, such enzymes include, in non-limiting example, CYP enzymes such as CYP2C9 (luciferin-H), CYP3A4 (luciferin-IPA), a combination of CYP1A1, CYP1A2, CYP2B6 and CYP2D6 (luciferin ME-EGE), all CYP450 enzymes such as CYP2C8, CYP2C19, CYP2E1, and phase II enzymes such as UGTs, SULTs and NATs, and any combination thereof.

Levels of biomarkers such as for example specific metabolites may also be used in screening assays for agents. This may also be accomplished using standard cytological and/or histological techniques including the use of immunocytochemical techniques employing stains that recognize specific cellular components such as lipids, or antibodies that specifically bind to biomarkers with antigenic activity. For example, stable iMPCCs may be exposed to a test agent or candidate therapeutic agents. After incubation, the micropattern cultures may be examined for change in biomarker production as an indication of the efficacy of the test substance. Varying concentrations of a candidate therapeutic agent may be tested as known in the art to derive a dose-response curve.

Target Validation

The compositions of the invention can be used in drug development for specific target identification and target validation. The iMPCCs are useful for identifying targets and predicting the role of one or more biomolecules in liver function in a disease or disorder of the liver. A "disease or disorder of the liver" is any medical condition having a negative effect on any liver function. Non-limiting examples of liver diseases and disorders include cirrhosis, diabetes, fibrosis, any chronic hepatitis (including but not limited to A, B, C, D, E), non-alcoholic fatty liver, alcoholic fatty liver, tumors of the liver such as hepatic carcinoma, and genetic disorders such as alpha-1-anti-trypsin deficiency.

For example, the cultures and systems may be used to identify proteins playing a potential role in fibrosis of the liver, or those playing a potential role in diabetic processes or diabetic liver pathways. Identified proteins may be modulated (e.g., up-regulated or down-regulated) in the co-cultures described herein, and processes and pathways related to diabetes may be assayed following modulation.

The cultures and/or systems are also useful for validating the predicted role of one or more biomolecules in liver function in a disease or disorder of the liver. For example, proteins identified in preliminary studies (e.g., studies of primary hepatocytes in conventional culture systems or cryogenically preserved hepatocytes, studies in other liver models, differential expression studies, etc.) as playing a potential role in disease processes or disease pathways can be tested in a composition as described herein to confirm the potential role. Proteins identified from preliminary studies, for example proteins suspected to play a role in diseased or disordered liver function, may be modulated (e.g., up-regulated or down-regulated) in the co-cultures described herein, and processes and pathways related to the disease or disorder may be assayed following modulation. For example, candidate proteins can be "knocked out/down" using gene knockout or suppression techniques, for example, using various genomic editing techniques, or the introduction of RNA interference (RNAi) agents. Inhibition of liver pathways may be tested following down-regulation and candidate proteins thought to be important in disease or disordered liver function may be thus validated.

Any method using the co-cultures as disclosed herein may comprise initially preparing or otherwise obtaining a micro-patterned co-culture of pluripotent stem cell derived hepatocytes and non-parenchymal cells as described herein, including a layer of material comprising at least one extracellular matrix protein disposed on the co-culture. In one aspect, a stable, growing co-culture is established having a desired size (e.g., island size and distance between islands) as described herein above. In one aspect, the present disclosure provides a method of determining the efficacy of a candidate therapeutic agent for treating a disease or disorder of the liver. The candidate therapeutic agent may be a small molecule, a peptide, a polypeptide, an oligonucleotide, a polynucleotide, or an antibody.

The co-culture is exposed to varying concentrations of the candidate therapeutic agent. The amount of the candidate therapeutic agent may be, according to knowledge is available to those of skill in the art, an amount representing a proposed dose or range of proposed doses in a clinical population. The time over which the hepatocytes in the co-culture are exposed to the candidate therapeutic agent may be, according to knowledge available to those of skill in the art, a period of days, weeks or months representing time course of exposure in a clinical population. After incubation with the agent, the culture is examined to determine impact of the agent if any on one or more target biomolecules or pathways identified as potentially involved in liver function in a disease or disorder of the liver, as described above. Once a testing range is established, varying concentrations of the agent can be tested to determine therapeutically effective amount of the test compound.

As noted above, stem cell derived hepatocytes can be derived from stem cells obtained from one or more human donors suffering from a disease or disorder of the liver. For example, stem cell derived hepatocytes can be derived from stem cells obtained from one or more human donors suffering from a metabolic disorder of the liver, such as Type 2 diabetes. The methods therefore encompass, for example, a method for testing a candidate therapeutic agent for treating a metabolic disorder of the liver, including maintaining a co-culture as described herein for a time and under conditions sufficient to allow glucose production by the hepatocytes; and determining a level of glucose production by the hepatocytes, wherein the level of glucose production relative to the level of glucose production in a population of control stem cell derived hepatocytes is indicative of the efficacy of the test compound as an therapeutic agent for treating the metabolic disorder of the liver. The method may further comprise, prior to determining the level of glucose production by the hepatocytes: depleting the co-culture of glycogen in glucose-free medium for a period of at least about twelve hours; contacting the co-culture with at least one substrate of a gluconeogenesis enzyme; and maintaining the co-culture for a period of at least about 12 hours under conditions sufficient for glucose production in the hepatocytes to occur. The co-culture may be maintained for a period of at least about 24 hours, or at least 48 hours under conditions sufficient for glucose production in the hepatocytes to occur. The at least one substrate of a gluconeogenesis enzyme may be for example lactate or pyruvate.

It should be understood that the present disclosure encompasses methods of identifying any test agent useful for modulating a biological activity of interest in a hepatocyte, in which a co-culture as disclosed herein is contacted with the test agent; the co-culture is maintained for a time and under conditions sufficient for the hepatocytes to generate a signal indicative of the biological activity; and a signal generated by the stem cell derived hepatocytes in the presence of the test agent is detected, wherein the signal relative to a signal generated in a control stem cell derived hepatocyte in a control co-culture is indicative of an effect on the biological activity of interest in the hepatocytes. The signal indicative of the biological activity of interest may be for example a protein expression level or a protein secretion level. The biological activity of interest may be glucose metabolism. The biological activity of interest may be albumin secretion or urea synthesis. The agent may be a small molecule, a peptide, a polypeptide, an oligonucleotide, a polynucleotide, and an antibody.

Toxicity Studies

In addition to the above-described uses of the cultures and/or systems of the invention in screening for therapeutic agents for treating a disease or disorder of the liver, the co-cultures may also be used in toxicology studies to determine the hepatotoxicity of an agent identified as a potential therapeutic agent. Toxicology studies may be performed on co-cultures featuring hepatocytes derived from stem cells from human donors suffering from a disease or disorder of the liver, as described herein, which may be contrasted with comparable studies in cells from a different source. The co-cultures described herein may be used in vitro to test a variety of potential therapeutic compounds for hepatotoxicity. Any of the screening methods described herein above may further comprise determining the toxicity of the agent by measuring in the stem cell derived hepatocytes at least one cell signal indicative of cell toxicity.

Toxicity results may be assessed for example by observation of any of the following: a change in albumin and/or urea production, induction of any inducible liver is enzyme such as cytochrome P450 (CYP) enzymes, cellular necrosis, loss of membrane integrity, cell lysis, decrease in cell viability, apoptosis, mitochondrial membrane potential, mitochondrial DNA, ER stress, and steatosis, using any one or more of vital staining techniques, ELISA assays, RT-qPCR, immunohistochemistry, and the like or by analyzing the cellular content of the culture, e.g., by total cell counts, and differential cell count, by metabolic markers such as MTT and XTT, or by hepatocyte imaging technology (HIAT).

For example, co-culture as described herein are exposed to varying concentrations of a candidate therapeutic agent. The amount of the candidate therapeutic agent may be, according to knowledge available to those of skill in the art, an amount representing a proposed dose or range of proposed doses in a clinical population. The time over which the hepatocytes are exposed to the candidate therapeutic agent may be, according to knowledge available to those of skill in the art, a period of days, weeks or months representing time course of exposure in a clinical population. After incubation with the agent, the culture is examined to determine the highest tolerated dose, i.e., the concentration of the agent at which the earliest morphological and/or functional abnormalities appear or are detected. Cytotoxicity testing may also be performed using a variety of supravital dyes to assess cell viability in the culture system, using techniques known to those skilled in the art. Once a testing range is established, varying concentrations of the agent can be examined for hepatotoxic effect.

The present disclosure thus provides a method for determining the cellular toxicity of a candidate therapeutic agent or test compound, the method comprising contacting a co-culture as described herein with the test compound; maintaining the co-culture for a time and under conditions sufficient to allow an effect of the test compound on the stem cell derived hepatocytes; and taking a test measurement and/or otherwise obtaining test data indicative of a negative impact of the test compound on the stem cell derived hepatocytes, which is indicative of hepatotoxicity of the test compound. The test measurement can be any measurement which provides an indicator of hepatic cell function. For example, the test measurement can be a measurement of at least one or any combination of albumin, urea and ATP production. The test measurement can be a measurement of at least one inducible liver (e.g., CYP) enzyme level. Test data may include applying hepatocyte imaging technology (HIAT) to the hepatocytes to obtain a test image. The test measurement and/or test image is compared to a control measurement or control image from the hepatocytes before contact with the test compound, and a difference between the test measurement and control measurement, or between test image and control image is indicative of hepatotoxicity of the test compound. For example, a relative decrease in albumin and/or urea production in test measurements as compared to control, following exposure of the co-culture to the test compound is indicative of hepatotoxicity. A relative increase in inducible CYP enzyme test measurements as compared to control, following exposure of the co-culture to the test compound is indicative of hepatotoxicity.

The present disclosure also provides a method of determining the hepatotoxicity arising from a drug interaction. For example, the potential hepatotoxicity of an interaction between a first test compound and a second test compound can be examined by contacting a co-culture as described herein with the first and second test compounds; maintaining the co-culture for a time and under conditions sufficient to allow an effect of an interaction between the first and second test compounds on the stem cell-derived hepatocytes; and taking a test measurement and/or otherwise obtaining test data as described above, which is indicative of hepatotoxicity of the interaction of the first and second test compounds.

It should be understood that many other signals of hepatotoxicity from the stem cell derived hepatocytes can be detected and/or measured and compared to controls to identify and/or quantify hepatotoxicity induced by a candidate therapeutic agent, wherein the signal relative to a signal generated in a control co-culture is indicative of a toxic effect of the candidate agent on the stem cell derived hepatocytes. Such signals include, in non-limiting example, cellular necrosis, loss of membrane integrity, cell lysis, decrease in cell viability, apoptosis, mitochondrial membrane potential, mitochondrial DNA, ER stress, and steatosis, any one of which can be readily measured using techniques and materials known in the art.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

Personalized Medicine

It has been found that certain correlations can exist between an individual subject's particular genotype with respect to specific molecular markers, and drug treatment efficacy. Any of the co-cultures and methods described herein can also be used to develop personalized medicine, to determine whether any such correlation exists between a particular genotype and selected drug treatment for a disease or disorder of the liver. For example, co-cultures can be prepared using hepatocytes derived from pluripotent stem cells obtained from a variety of donors of different genotypes, and any therapeutic candidate can be tested for efficacy against each genotype to determine whether any one or subset of the tested genotypes fares better or worse with a given therapeutic candidate. Any therapeutic candidate can be tested for effect on any inducible liver enzymes, and/or for a negative interaction with a second therapeutic candidate. Such information considered together with the genotype of an individual patient, can be used by a health care provider to determine a treatment option with the highest likelihood of efficacy for the individual subject, and/or to determine a risk of a negative side effect in the individual subject from a therapeutic candidate.

C. Examples

Example 1

Micropatterned Pure iHep Cultures

Micropatterned cultures of primary iHeps (Cellular Dynamics International) were first prepared to confirm the ability of iHeps to exhibit characteristics of human hepatocytes. Initial iHep processing proceeded as follows. Induced pluripotent stem cell-derived human hepatocytes were provided fresh in suspension by Cellular Dynamics International (CDI). Using a published protocol, CDI generates ~95% pure iHeps (via α1-antitrypsin). Upon arrival, iHeps were processed according to manufacturer-supplied protocols. Briefly, iHep cell aggregates were rinsed with divalent cation-free Hank's Balanced Saline Solution (HBSS, Hyclone), dissociated with 0.5% trypsin-EDTA (Life Technologies), neutralized with a 1:1 solution of Roswell Park Memorial Institute 1640 (RPMI, Life Technologies) media and fetal bovine serum (FBS, Life Technologies), and pelleted via centrifugation. iHeps were re-suspended in Kryothaw (SciKon Innovation, Inc.) and further centrifuged to remove ineffective cells and excess debris. Finally, iHeps were diluted in CDI's seeding media, composed of RPMI, 1 μM dexamethasone, 2% (v/v) B27 (Life Technologies), 1% (v/v) penicillin/streptomycin, and 20 ng/mL Oncostatin M (R&D Systems), and plated.

Micropatterned pure iHep cell cultures were prepared substantially as described in Khetani and Bhatia, NATURE BIOTECHNOLOGY 26(1):120-6 (2008) (the entire disclosure of which is incorporated herein by reference), except that the cells, i.e., the hepatocytes were iHeps, and unlike the co-cultures the pure iHeps did not receive the iMPH. Pure iHeps and co-cultures as described below also optionally included a Matrigel™ overlay as described in further detail below. Micropatterned pure iHep cultures were also used as density-matched controls in examples described below.

Unless otherwise indicated, in this and other examples control cultures were established using conventional confluent monolayer culture techniques to prepare confluent monolayer cultures of iHeps (iCCs). Following manufacturer protocols, processed iHeps were diluted to a density of $8 \times 10^5$ cells/mL and seeded in collagen-coated wells (500 μL/well in 24-well format). After attachment (2-4 hrs for >85% confluent iHeps), BD Matrigel™ Basement Membrane Matrix (BD Biosciences; "Matrigel™") was diluted to 0.25 mg/mL in cold maintenance media (identical to CDI's seed media, except 100 nM dexamethasone instead of 1 μM) and added to the cultures. Maintenance media was replaced after the first 24 hours and every other day thereafter.

Figure 4:
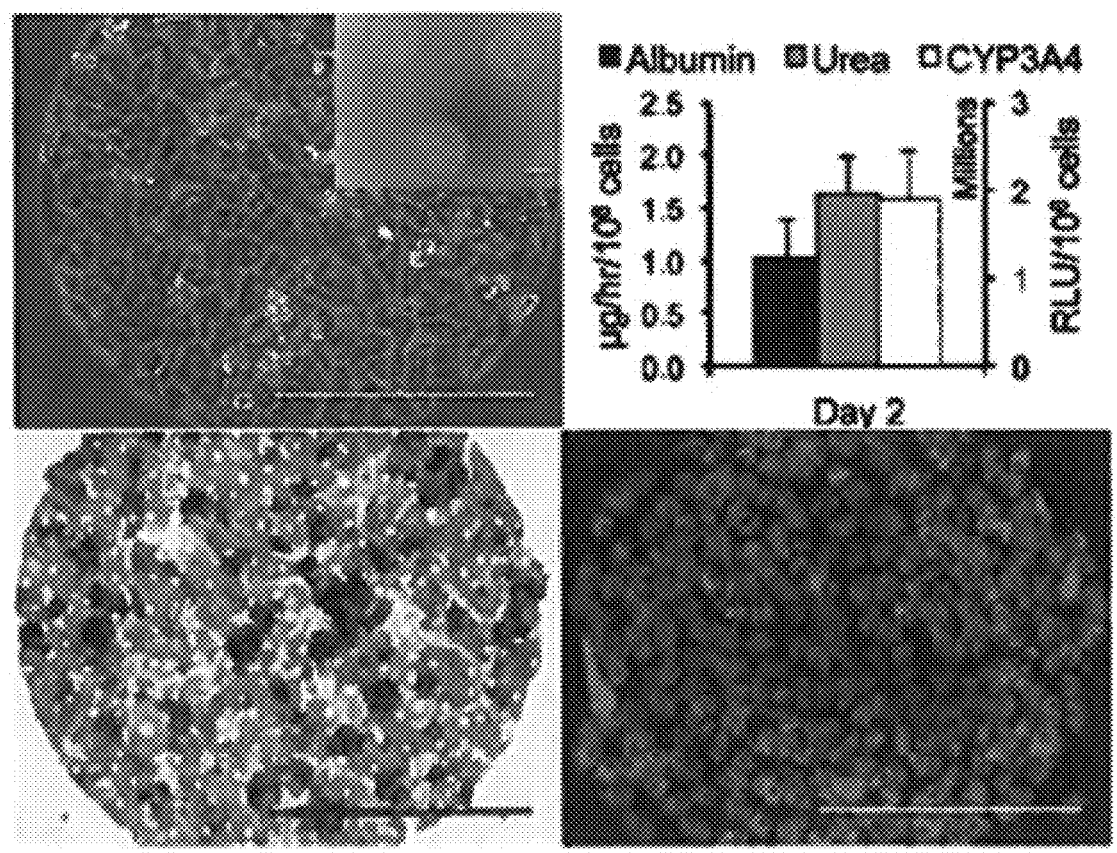
FIG. 4 Initial iHep characterization. Commercially supplied iHeps (Cellular Dynamics International) were capable of attaching and spreading onto micropatterned type I collagen domains with precise geometries (500 µm in diameter and 1200 µm center-to-center) (see inset, upper left). iHeps exhibited morphology typical of human hepatocytes. Average albumin production, urea secretion, and CYP3A4 activity across three independent batches of micropatterned iHeps on day 2 (upper right). Positive staining for intracellular glycogen storage (lower left) and albumin (lower right) after 2d of culture is indicative of hepatocellular functions. All error bars represent s.d. (n=3).

Selective adhesion of iHeps yielded micropatterned 'islands' 500 μm in diameter and spaced 1200 μm apart (center-to-center). Freshly attached iHeps displayed the is cobblestone appearance, round nuclei, distinct nucleoli, and occasional bi-nucleation typical of primary hepatocyte morphology. Functional characterization revealed demonstrable levels of albumin and urea production (protein synthesis and metabolism), CYP3A4 activity (phase-I drug metabolism), and positive staining for glycogen storage (glucose metabolism) (FIG. 4). Gene expression analysis of iHeps in suspension (immediately after receipt) verified the presence of mature hepatocyte markers ALB, HNF4A, ONECUT1 (HNF6), SERPINA10 (A1AT), SLCO1B1 (OATP2), TAT, and TDO2 (data not shown).

Example 2

Micropatterned Co-cultures of iHeps and iMPHs

Micropatterned co-cultures (iMPCCs) of iHeps and iMPHs were established using the following methods.

Murine embryonic 3T3-J2 fibroblasts were the gift of Howard Green (Harvard Medical School). Cells were cultured at 37° C., 10% $CO_2$ in Dulbecco's Modified Eagle's Medium (DMEM) with high glucose, 10% (v/v) calf serum, and 1% (v/v) penicillin-streptomycin.

Tissue culture polystyrene 24-well and 96-well plates (BD Falcon) were homogeneously coated with 25 µg/mL rat tail collagen I (BD Biosciences) and subjected to soft lithography-based methods to micropattern circular collagenous islands (500 µm diameter with 1200 µm center-to-center spacing). To establish iMPCCs, iHeps were seeded at a density of $6.66 \times 10^5$ cells/mL into micropatterned wells (300 µL and 50 µL per well in 24-well and 96-well plates, respectively) and agitated every 20 minutes to distribute cells for selective binding to collagen islands. Following 4-5 h for complete cellular attachment and spreading, wells were washed 3 times in RPMI base media to remove unattached iHeps. A typical collagen island contains 250-300 iHeps, yielding ~25,000 iHeps per well in 24-well format (96 islands/well) and 4,500 iHeps per well in 96-well format (16 islands/well). 3T3-J2 fibroblasts were subsequently seeded at a density of $4 \times 10^5$ cells/mL and allowed to fill the remaining area surrounding the iHep islands. Micropatterned pure iHep cultures, which did not receive murine fibroblasts (iMPHs), were used as density-matched controls. Matrigel™ overlays were applied to micropatterned cultures 2 days after fibroblast seeding to allow for the formation of a confluent layer of stromal cells.

Figure 5:
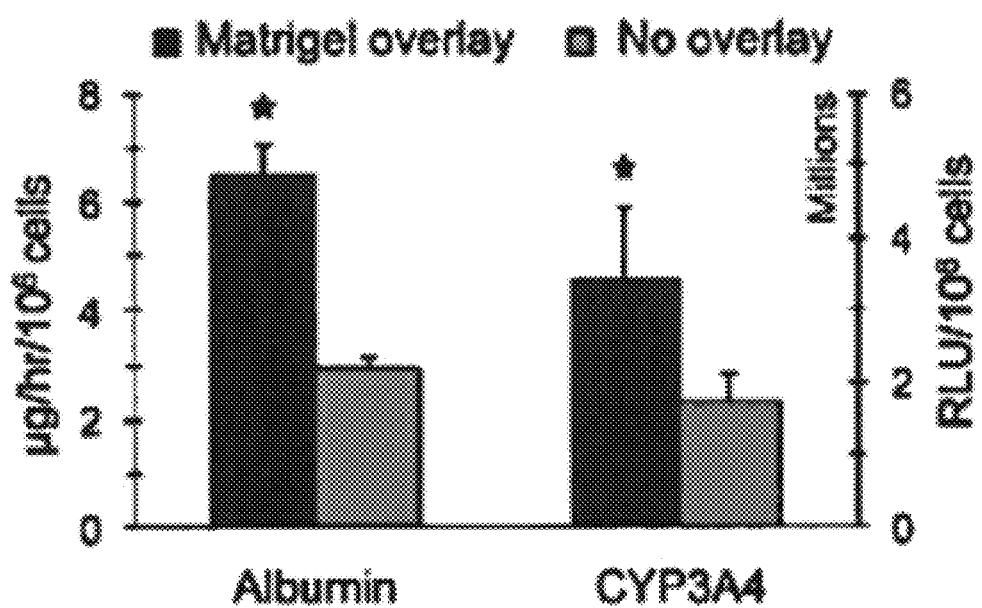
FIG. 5 Matrigel™ overlays enhance hepatic functionality in the iMPCC model. The addition of Matrigel™ overlays significantly increases albumin synthesis and CYP3A4 activity in the first week of culture (day 6). Data from representative study shown. All error bars represent s.d. (n=3). * p<0.05.

Following established protocols, hepatocyte culture medium was changed every other day thereafter. Following iHep attachment and spreading (4-6 h), embryonic murine 3T3-J2 fibroblasts were added to form a confluent layer of supportive stromal cells surrounding the iHep islands. The addition of a Matrigel™ overlay, commonly used for primary hepatocyte culture, increased albumin production and CYP3A4 activity in co-cultured iHeps (FIG. 5). Accordingly, the combination of iHep/3T3-J2 micropatterned co-cultures with a superimposed layer of Matrigel™ established the initial iMPCC model.

Example 3

Qualitative Assessment of iMPCC Stability

To qualitatively assess iMPCC stability, iHep morphology was monitored using an EVOS®FL cell imaging system with standard 10× or 20× objectives and phase contrast. For immunofluorescence, DAPI (357/44 Ex, 447/60 Em), GFP (470/22 Ex, 510/42 Em), and RFP (531/40 Ex, 593/40 Em) LED light cubes were used.

For albumin immunofluorescence, live cultures were washed once in phosphate buffered saline (PBS), fixed in 4% paraformaldehyde (Alfa Aesar) for 15 minutes, and followed with 3× PBS rinses (5 minutes each). Fixed cells were permeabilized using 0.1% triton X-100 (Amresco) for 10 minutes followed by another 3× PBS rinses (5 minutes each). Samples were incubated at 37° C. for 30 minutes in blocking solution, consisting of 20% goat serum (Thermo Scientific) in PBS. Primary rabbit anti-human intracellular albumin antibody (Rockland) was added to blocking solution 1:100 and incubated for 1 hour at 37° C. After incubation, cultures were washed 3× in PBS, and incubated with rhodamine conjugated goat anti-rabbit IgG secondary antibodies (Rockland), diluted 1:100 in blocking solution, for 1 hour at 37° C. For the final 15 minutes of incubation, DAPI counterstain was added at 300 nM. After 3 additional PBS washes, cultures were imaged with DAPI and RFP light cubes.

Bile canaliculi, glycogen, and LDL uptake staining were performed as follows. For staining functional bile canaliculi, co-cultures were washed three times with phenol-red free DMEM, then incubated at 37° C. with 2 µg/mL CDF [5-(and-6)-carboxy-2',7'-dichlorofluorescein diacetate, Life Technologies] for 10 minutes, and washed three times again prior to examination with fluorescence microscopy using the GFP light cube. Periodic-acid Schiff staining (Sigma) was used to assess glycogen uptake. In brief, cultures were fixed, washed 3× with PBS, and incubated for 7 minutes at room temperature with periodic acid solution. Cultures were again washed 3× with PBS and incubated with a 1:1 solution of Schiff's reagent and PBS for 5 minutes at room temperature. Finally, cultures were washed 10× with PBS and imaged using bright field microscopy. LDL uptake was assessed using Dil-LDL (Life Technologies). Cultures were washed three times with phenol-red free DMEM, then incubated with 20 µg/mL Dil-LDL in serum-free culture medium for 3 hours at 37° C. Cells were washed with PBS to remove unbound LDL and were imaged in phenol red-free DMEM.

Quantitative polymerase chain reaction (qPCR) was performed as follows. Total RNA was prepared using the RNeasy Mini Kit (Qiagen) and treated with RNase-free Optizyme Recombinant DNase I to remove genomic DNA content (Fisher Bioreagents). RNA (100 ng-1 µg) was reverse transcribed into cDNA using random primers and dNTPs with MultiScribe Reverse Transcriptase (Applied Biosystems). QPCR was performed on a MasterCycler EP RealPlex2 (Eppendorf) using select Solaris Human qPCR Gene Expression assays (Thermo Scientific). Expression levels were normalized to the housekeeping gene glyceraldehyde-3-phosphate dehydrogenase, GAPDH. Gene expression levels were calculated using the delta-delta CT method relative to the level in freshly processed iHeps.

Biochemical assays were conducted as follows. Culture supernatants were assayed for albumin secretions using a competitive enzyme-linked immunosorbent assay (ELISA, MP Biomedical) with horseradish peroxidase detection and 3,3',5,5'-tetramethylbenzidine (TMB, Rockland) as the substrate. Similarly, AFP was quantified using a sandwich ELISA (R&D Systems). Urea production was measured by a colorimetric endpoint analysis with diacetylmonoxime, acid, and heat (Stanbio Labs). ATP levels in cell lysates were quantified by CellTiter-Glo (Promega); levels in iMPCCs were subtracted from fibroblast-only controls to establish iHep-only values.

The iMPCCs demonstrated hepatic characteristics (i.e. polygonal morphology, distinct nuclei/nucleoli, presence of bile canaliculi) which were preserved for at least 4 weeks (FIG. 1A). In contrast, micropatterned iHeps lacking the supportive stromal fibroblasts (iMPH) began to spread and separate within the first week of culture, transiently losing hepatic features. Using fluorometric substrates specific to functional bile canaliculi and lipid metabolism, we found co-cultured iHeps to display positive transporter activity and uptake of low-density lipoprotein (FIG. 1B). The magnitude of liver-specific functions in iMPCCs was notably greater than conventional confluent monolayers (iCC) and density matched iMPH cultures, paralleling the observed divergence in morphology (FIG. 1C). Normalized iMPCC albumin and urea secretion rates reached steady state by the first week in culture and maintained levels for at least 28 days. When compared to stabilized micropatterned co-cultures of primary human hepatocytes (8 donors in total) described previously (S. March, et al., Cell Host Microbe 14: 104-15 (2013)), iHeps in the iMPCC model produced equivalent levels of albumin and 30-50% of urea levels.

Figures 2A, 2B:
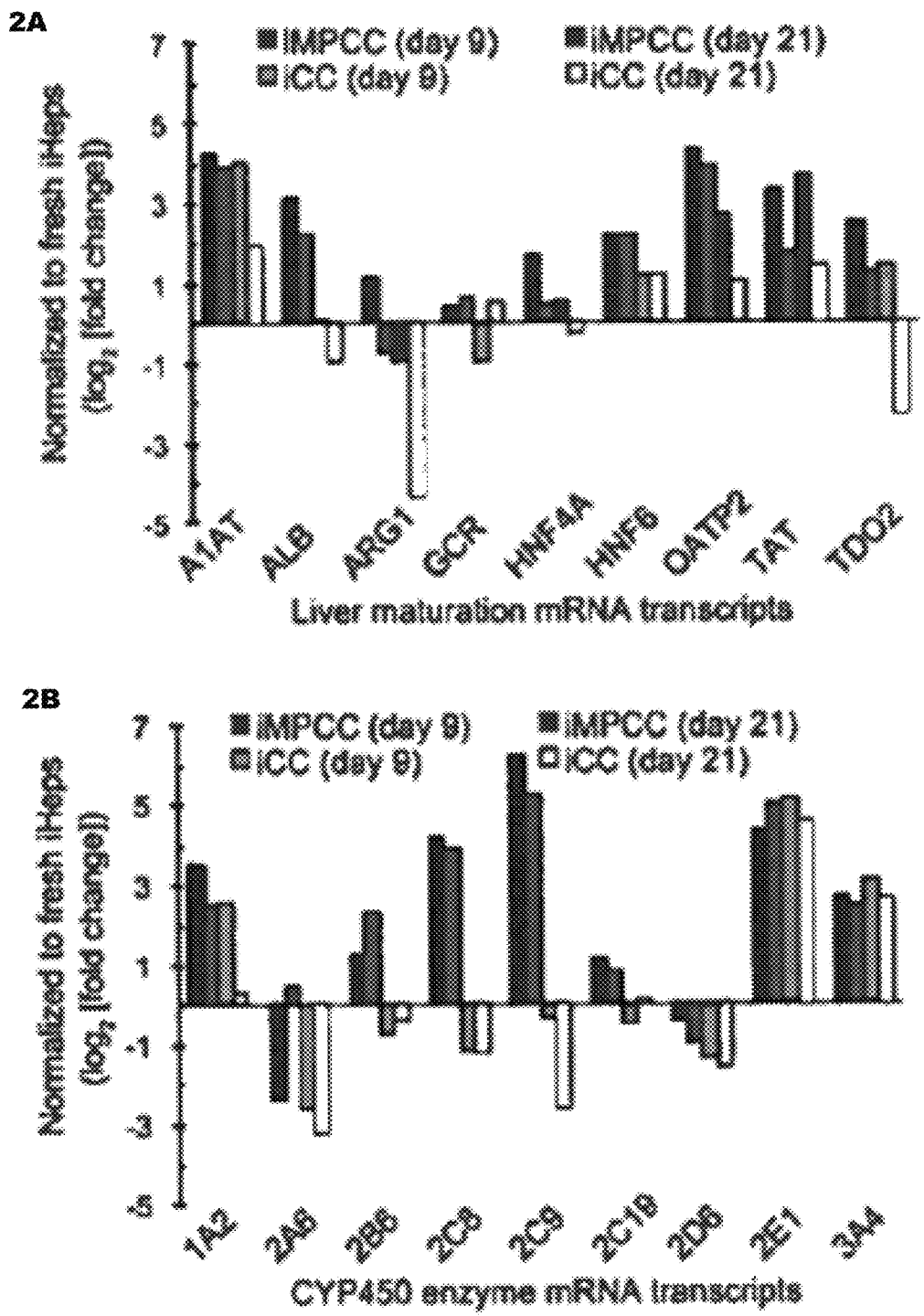
FIGS. 2A, 2B, 2C and 2D, Gene expression and cytochrome P450 (CYP) activity.

Relative gene expression analysis shows controlled stromal interactions to promote the transcriptional maturation of iHeps, as the expression of liver specific genes was greater in iMPCCs compared to fresh iHeps (FIG. 2A). While the majority of mRNA transcripts displayed increased expression (~2-16 fold), the expression of ARG1 was down-regulated by the third week of culture. A decrease in expression of ARG1, a gene encoding the enzyme responsible for the conversion of arginine to urea, perhaps manifests in the reduced urea production rates observed in iMPCCs relative to primary hepatocytes. When likened to iMPCCs, iHep only cultures displayed predominantly reduced levels of expression. Due to the rapid loss of homotypic interactions in iMPH cultures, gene expression in iMPCCs was compared against iCCs, which maintained cellular contact to a greater extent. Down regulation of several mature hepatocyte markers (ALB, ARG1, HNF4A, and TDO2) by the third week of culture reveals the inability of the iCC model to maintain the initial iHep transcriptional state. Similar to liver-specific transcripts, many genes encoding for phase-I CYP enzymes showed marked is up-regulation in iMPCCs while their expression levels in iCCs was below that of fresh iHeps (FIG. 2B).

Example 4

Functional Assays of iMPCCs

Functional activities of phase-I enzymes were analyzed using multiple luminescence-based assays, including two CYP specific substrates (CYP2C9 and CYP3A4) and a third substrate to assess the combined metabolic activity of several CYP isozymes (1A1, 1A2, 2B6 and 2D6).

Cytochrome P450 (CYP) activity assays were conducted as follows. Luminescence-based assays (Promega) for CYP2C9 (luciferin-H), CYP3A4 (luciferin-IPA), and the combined activity of CYPs 1A1, 1A2, 2B6, and 2D6 (luciferinME-EGE) were used to measure iHep CYP activity. Cultures were rinsed in phenol red-free DMEM, and incubated with luminescent substrates, diluted in DMEM, for 1 hour (3 µM luciferin-IPA, 10 µM luciferinME-EGE) or 3 hours (50 µM luciferin-H) at 10% $CO_2$, 37° C. Following incubation, 50 µL of assay media was collected, transferred to a white 96-well plate, combined 1:1 with substrate-specific luciferin detection reagent, protected from light, and incubated for 20 minutes at room temperature. Luminescence was measured using a BioTek Synergy H1 tri-mode plate reader at full gain settings with an integration time of 1.0 second.

Conventional CYP substrates (Sigma) included Bupropion HCl (Bup), Coumarin (Cou), Dextromethorphan (Dex), Phenacetin (Phe), S-Mephenytoin (S-Me), Testosterone (Tes), and Tolbutamide (Tol). Cultures were incubated with substrates (Bup at 500 µM, Cou and Tol at 50 µM, Dex at 16 µM, Phe and S-Me at 100 µM, and Tes at 200 µM) for 3 hours at 37° C. The reactions were stopped by collection of the incubation medium, and the amounts of CYP enzyme processed metabolites were quantified via liquid chromatography/mass spectrometry (Integrated Analytical Services, Berkeley, Calif., and Apredica, Watertown, Mass.).

Figure 2C:
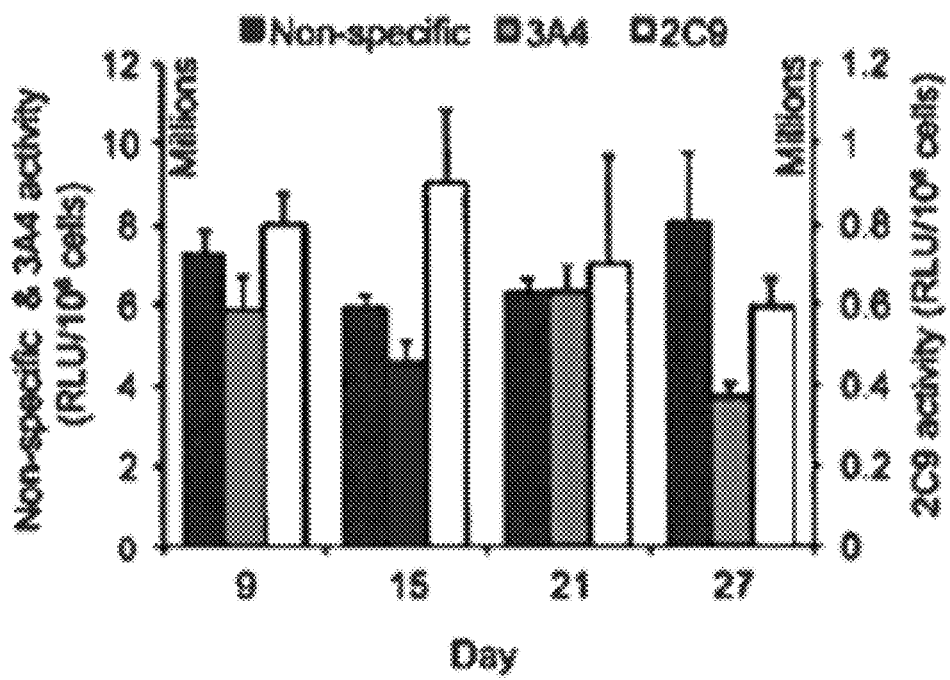
Figure 2D:
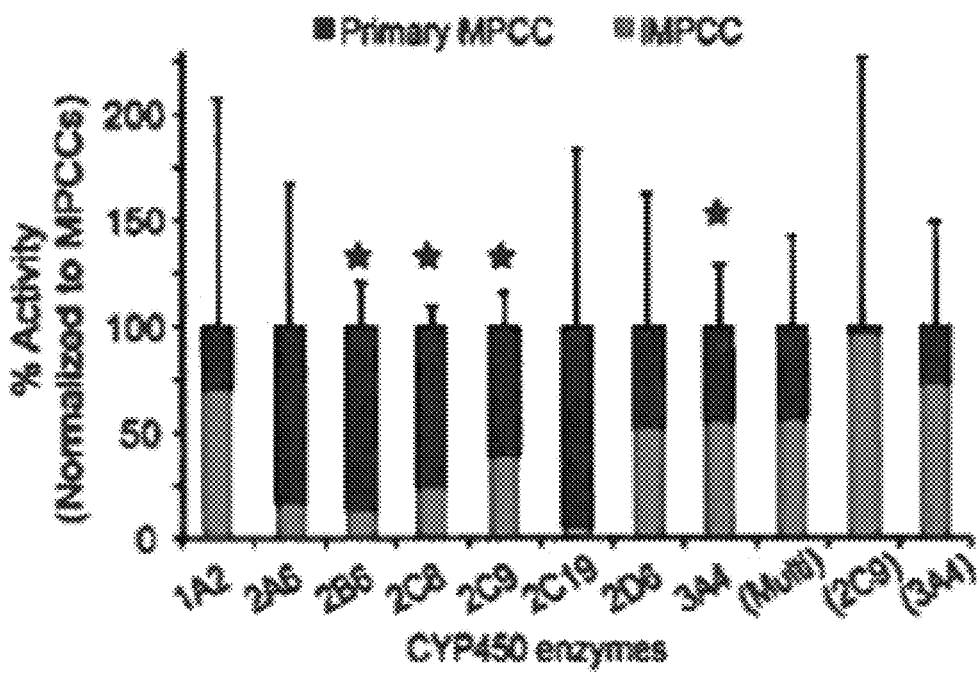
Figures 6A, 6B:
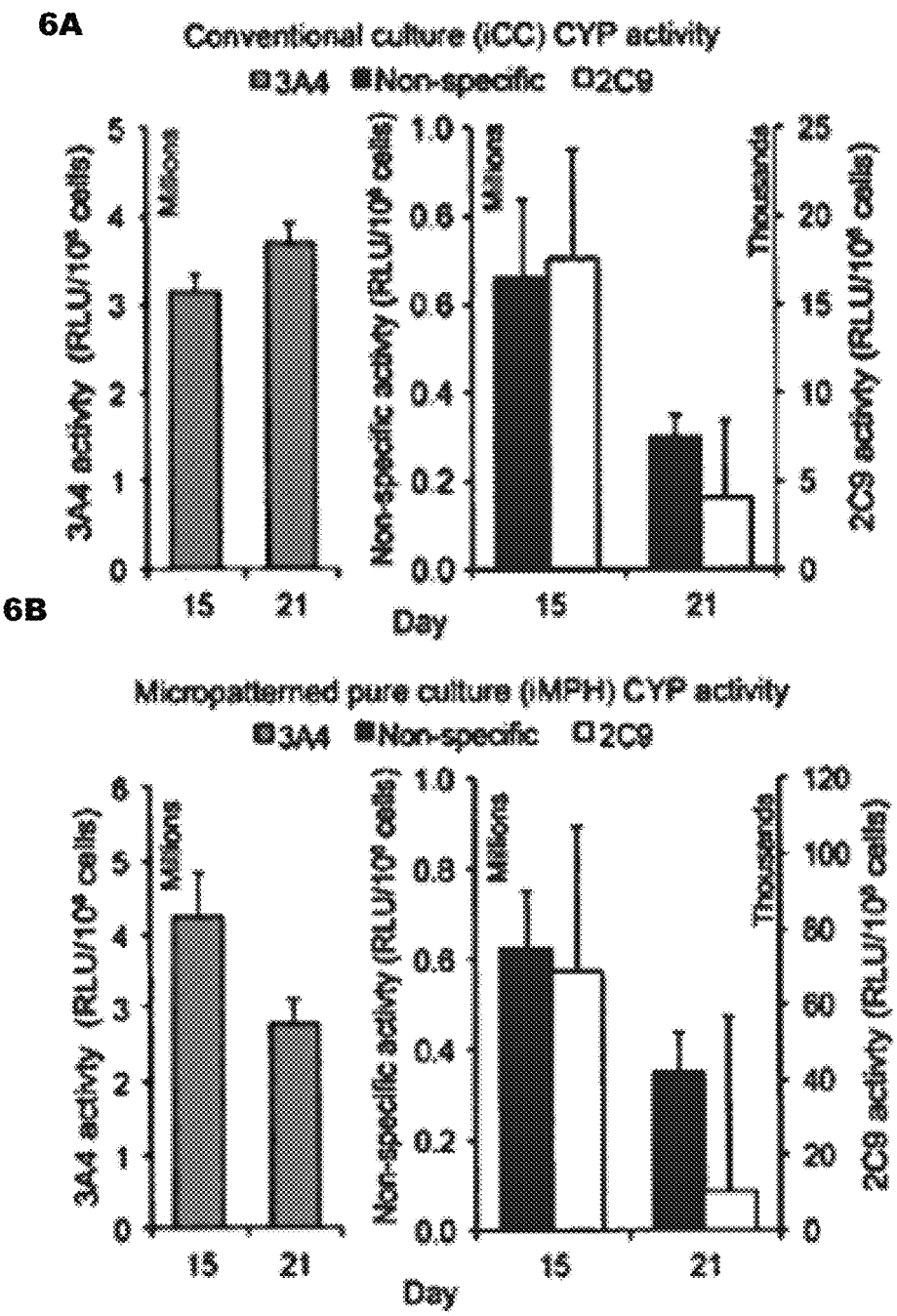
FIGS. 6A and 6B Cytochrome P450 (CYP) activity in pure iHep culture models.
Figure 7:
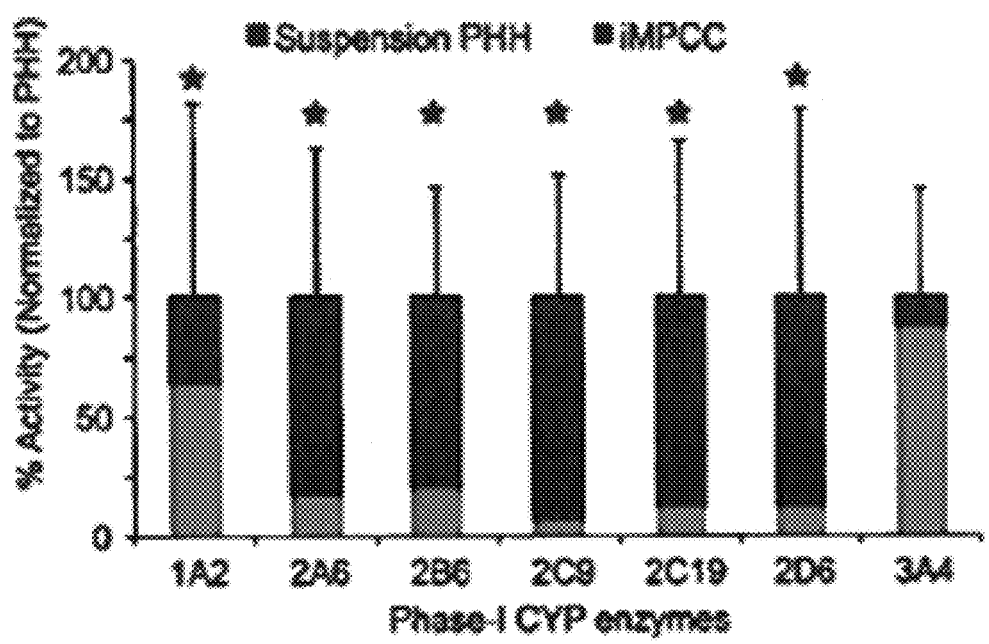
FIG. 7 Cytochrome P450 (CYP) levels in iMPCCs compared to suspension is primary human hepatocytes. Averaged CYP activity from commercial suppliers of cryopreserved human hepatocytes (BioreclamationIVT and Life Technologies). The number of donors ranged from 34 to 186 depending on the data available for a particular CYP substrate. All error bars represent s.d.
Figure 8:
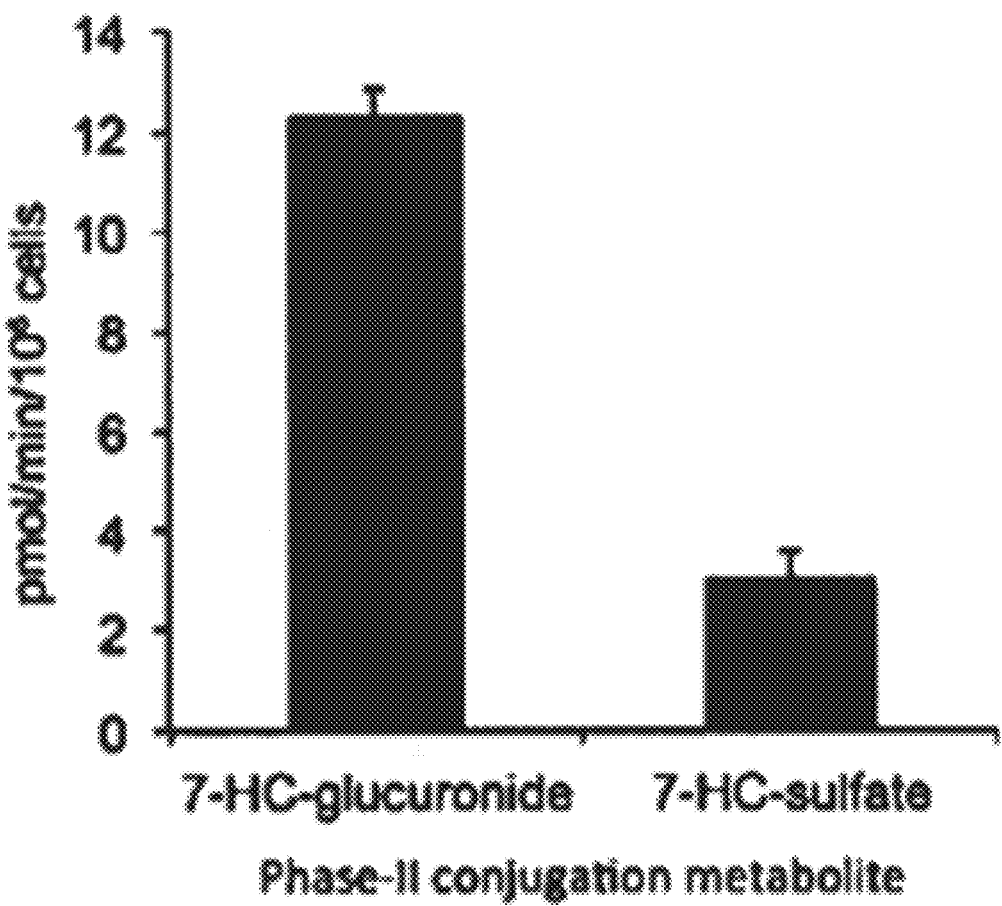
FIG. 8 Coupled phase I and phase II enzyme activities. iMPCCs were dosed with 50 µM coumarin and the rate of formation of 7-hydroxycoumarin-glucuronide and 7-hydroxycoumarin-sulfate was determined.

The iMPCC model stabilized iHep CYP activity levels for at least 4 weeks (FIG. 2C), whereas iHeps in the iMPH model exhibited reduced and largely declining CYP activity (FIG. 6A). Interestingly, while two substrates showed declining CYP activity is levels in iCCs, CYP3A4 maintained reduced but stable activity relative to iMPCCs (FIG. 6B). This observation may be rationalized by the up-regulated, stable expression of ONECUT1 (HNF6), a transcriptional regulator of CYP3A422, in both iMPCC and iCC models (FIG. 2A). Observed CYP activities in iMPCCS were compared against MPCC stabilized primary hepatocytes from multiple donors and found to reach 50-75% of primary hepatocyte CYP3A4 levels and 50-100% of primary hepatocyte CYP2C9 levels (FIG. 2D). In view of concerns about the substrate specificity of luminescence-based assays, CYP enzyme activity was confirmed using conventional FDA approved substrates (FIG. 2D). For several enzymes, the activities in iMPCCs were 50% or higher compared to MPCCs with primary hepatocytes. Further, CYP enzymatic activity levels from commercially available cryopreserved primary human hepatocyte lots were averaged across multiple vendors (FIG. 7). While several iHep CYP enzymes display lower activity levels than their primary hepatocyte counterparts, others, such as CYP3A4, are well within the normal diversity of human function. Coupled phase I and II activity was demonstrated in iMPCCs through the detection of 7-hydroxycoumarin glucuronide and 7-hydroxycoumarin sulfate following coumarin treatment (FIG. 8).

Example 5

Drug Toxicity Screening Using iMPCCs

Despite the great potential of using iHeps for drug toxicity screenings, current in vitro models have been restricted to use with highly toxic compounds, miss some overtly toxic compounds, and lack comparison to primary hepatocytes. Adapting the iMPCC model to a 96-well industry standard plate for high-throughput screening and eliminating Matrigel™ to minimize confounding variables, a set of 49 compounds which had been previously tested on primary human hepatocytes was screened using the iMPCCs (Table 1, below).

Drug dosing for toxicity calls and binary decision making was determined as follows. After approximately 1 week of stabilization, Matrigel™- and serum-free cultures were dosed three times, every other day, at 25·Cmax and 100·Cmax (total human plasma concentration, Table 2, below) at a DMSO concentration of 1.0% (phenacetin, phenylbutazone, and pyrazinamide), 0.2% (acetazolamide, cyclophosphamide, hydroxyurea, mefenamic acid, and quinine), or 0.1% (all other compounds). Vehicle-only controls were maintained at each DMSO concentration and used for subsequent binary decision making. In brief, data were normalized to vehicle-only controls, and any compound that showed at least a 50% reduction in at least one of the three assays (albumin, ATP, and urea) was classified as toxic.

For drug-drug interaction studies, to demonstrate mechanisms of toxicity, the glutathione depleting agent L-buthionine (S,R)-sulfoximine (BSO, Sigma-Aldrich) at 200 µM was co-incubated with acetaminophen (APAP) following the same dosing schedule as the other compounds. Controls without BSO were included as a baseline toxicity measurement.

TABLE 1

Compounds tested and binary decisions of toxicity in iMPCCs

| Compound name | DILI | | | Model predictions | | |
|---|---|---|---|---|---|---|
| | Sev | Cat | Clin | Sand | MPCC | iMPCC |
| True Positives In HIAT | | | | | | |
| Acetaminophen | N/A | P2 | + | + | + | + |
| Amiodarone | 8 | P2 | + | + | + | + |
| Benzbromarone | −2 | P1 | + | + | + | + |
| Clozapine | 2 | P2 | + | + | + | + |
| Diclofenac | 7 | P2 | + | + | + | + |
| Flurbiprofen | 3 | P2 | + | + | + | + |
| Mebendazole | 3 | P2 | + | + | + | + |
| Mefenamic acid | N/A | P2 | + | + | + | + |
| Phenacetin | N/A | P2 | + | + | + | + |
| Phenylbutazone | N/A | P2 | + | + | + | + |
| Quinine | N/A | P2 | + | + | + | + |
| Trazodone HCl | N/A | P2 | + | + | + | + |
| Troglitazone | −2 | P1 | + | + | + | + |
| True negatives in HIAT | | | | | | |
| Aspirin | N/A | O2 | − | − | − | − |
| Buspirone | 3 | N1 | − | − | − | − |
| Dexamethasone | 3 | N1 | − | − | − | − |
| Dextromethorphan HBr | N/A | N1 | − | − | − | − |
| Fluoxetine | 3 | N2 | − | − | − | − |
| Lidocaine | N/A | N1 | − | − | + | + |
| Miconazole | N/A | N1 | − | − | − | − |
| Prednisone | N/A | N2 | − | − | − | − |
| Propranolol | 3 | N1 | − | − | − | − |
| Rosiglitazone | N/A | N2 | − | − | − | − |
| Warfarin | 5 | N2 | − | − | − | − |
| False negatives in HIAT | | | | | | |
| Acetazolamide | N/A | P2 | + | − | + | − |
| Betahistine 2HCl | 6 | P2 | + | − | − | − |
| Captopril | 7 | P2 | + | − | − | − |
| Chloramphenicol palmitate | N/A | P2 | + | − | − | − |
| Ciprofloxacin HCl | 7 | P2 | + | − | + | + |
| Clomiphene citrate | N/A | P2 | + | − | − | − |
| Clomipramine | N/A | P2 | + | − | + | + |
| Cyclophosphamide | 5 | P2 | + | − | + | + |
| Cyproterone acetate | N/A | O1 | + | − | + | + |
| Danazol | 8 | P1 | + | − | − | − |
| Dapsone | N/A | P1 | + | − | + | − |
| Estrone | N/A | P2 | + | − | − | − |
| Hydroxyurea | 8 | P2 | + | − | + | − |
| Imipramine HCl | 3 | P2 | + | − | + | + |
| Isoniazid | 8 | P1 | + | − | + | + |
| Maleic acid | N/A | O1 | + | − | + | − |
| Methimazole | 8 | P2 | + | − | − | − |
| Nifedipine | 3 | P2 | + | − | − | − |
| Norgestrel | N/A | P2 | + | − | − | − |
| Nortriptyline HCl | 8 | P2 | + | − | + | + |
| Phentolamine mesylate | — | P2 | + | − | − | − |
| Piroxicam | 3 | P2 | + | − | − | + |
| Progesterone | N/A | P2 | + | − | − | − |

TABLE 1-continued

Compounds tested and binary decisions of toxicity in iMPCCs

| Compound name | DILI | | | Model predictions | | |
|---|---|---|---|---|---|---|
| | Sev | Cat | Clin | Sand | MPCC | iMPCC |
| Pyrazinamide | 3 | P2 | + | − | + | + |
| Tamoxifen | 6 | P2 | + | − | + | + |
| Overall specificity | | | | 100% | 91% | 91% |
| Overall sensitivity | | | | 34% | 68% | 63% |

Table 1 Notes:
The Sev column lists the DILI severity scores from the LTKB of the FDA, where N/A means not applicable/no information in the database; a negative number, the drug was withdrawn from the market; higher positive numbers, greater DILI concern; and three dashes, no DILI concern.
DILI categories (Cat column):
P1, DILI type 1, dose dependent (toxic);
P2, DILI type 2, idiosyncratic (toxic);
N1, not known to cause liver injury (nontoxic);
N2, sporadic cases (<10) of liver injury reported but generally considered safe drug to use by doctors (nontoxic);
O1, hepatotoxic in animals untested in humans (toxic);
O2, elevated liver enzymes observed in humans but does not lead to frank liver toxicity (nontoxic).
The right four columns compare clinical DILI (Clin) with binary decisions in sandwich cultures (Sand), MPCCs, and iMPCCs.

Figure 9A:
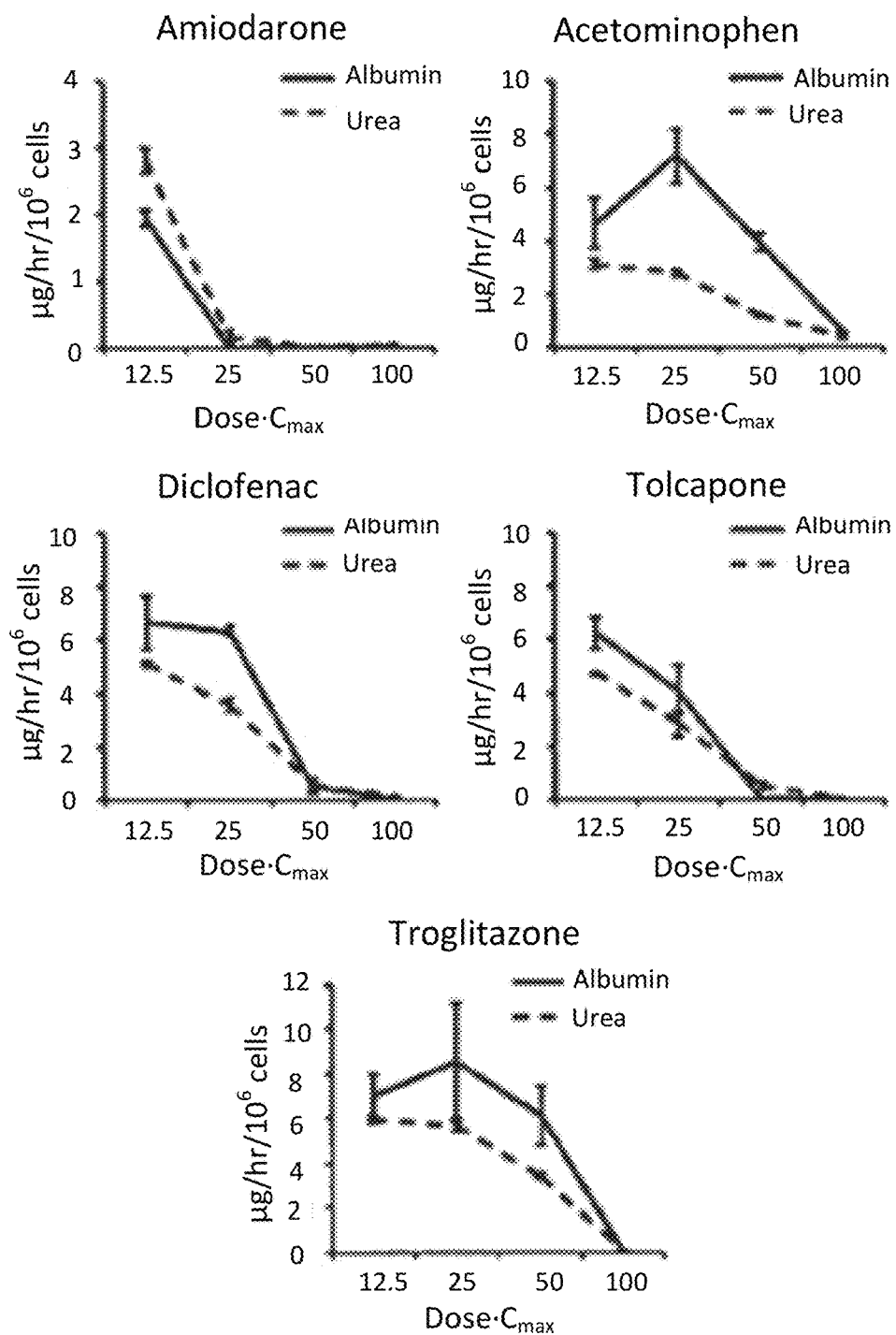
FIGS. 9A and 9B Dose response curves to prototypical hepatotoxins and non-toxins. Albumin synthesis and urea secretion in iMPCCs following 6 d of dosing with FIG. 9A hepatotoxins and FIG. 9B non-toxins.
Figure 9B:
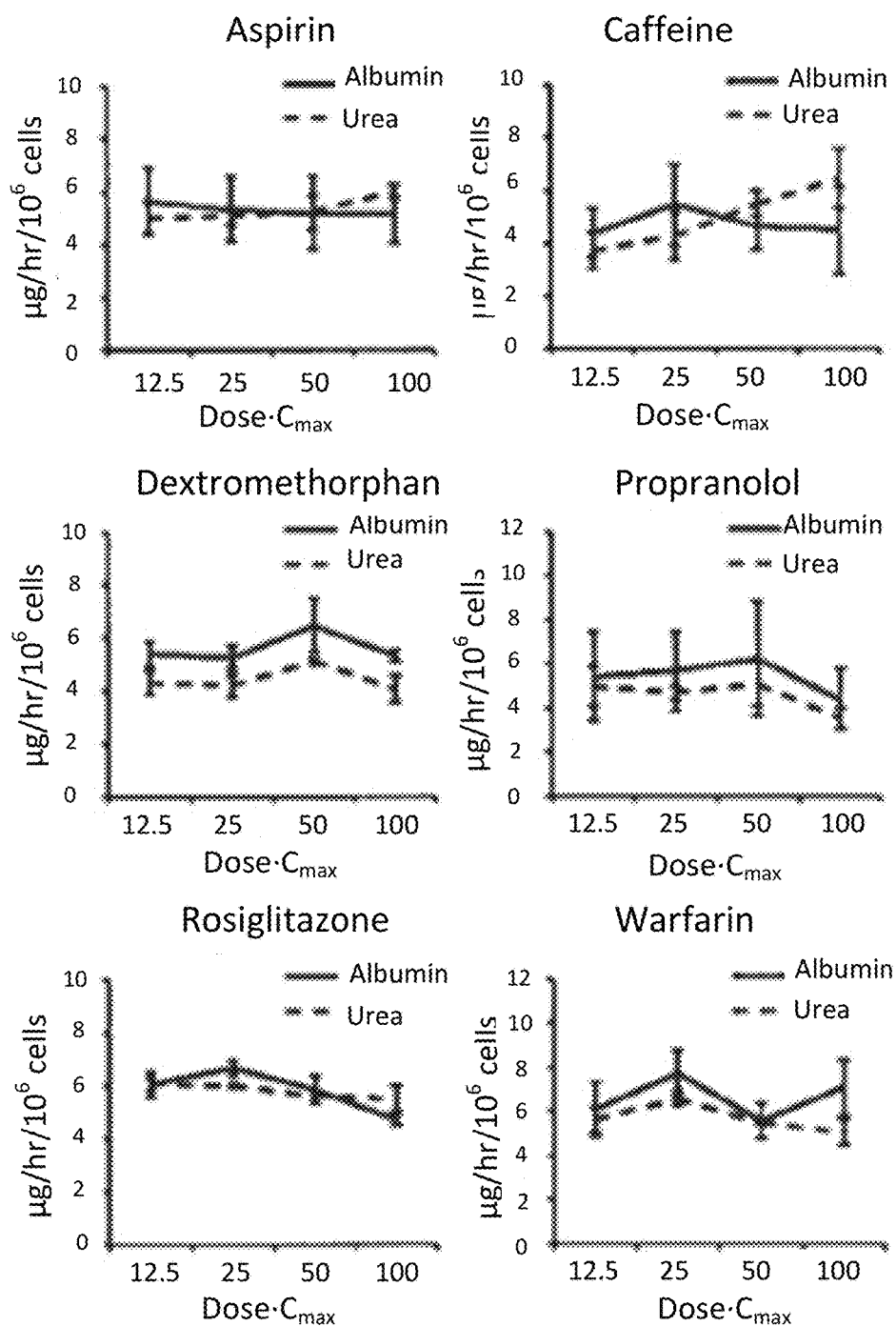

Of the 49 compounds tested, 13 true positive drugs were correctly identified as hepatotoxins in hepatocyte imaging assay technology (HIAT), 11 true negatives were correctly identified as non-toxic in HIAT, and 25 false negatives were incorrectly identified as non-toxic in HIAT. Running albumin, urea, and ATP assays has been is previously shown to be sensitive markers in primary human hepatocytes, so those three markers were used for iHeps and showed a strong dose-dependence (FIGS. 9A and 9B). Ultimately, the specificity and sensitivity of the system on the tested compounds were 91% and 63%, respectively, which were consistent (within 5%) with primary human hepatocytes in MPCCs.

All thirteen of the true positive compounds were correctly identified; lidocaine was the only true negative considered toxic as it was in primary hepatocytes, possibly due to the repeat dosings, variability in CYPs, or the inhibition of CYP1A. Eleven false negative compounds were correctly identified as toxic in iHeps, suggesting a more mature phenotype than in the HIAT model. Three false negative compounds were considered toxic in primary human hepatocytes 19 but not in iHeps. However, testing these compounds in another donor of primary hepatocytes (HUM4011, Triangle Research Labs) showed each was either a false negative (acetazolamide and dapsone) or borderline positive (maleic acid); this could demonstrate donor-to-donor variability seen in different donors of hepatoyctes. The false negative result from dapsone, thought to be metabolized by a variety of CYP enzymes, could indicate a down regulation of certain CYPs in iHeps. Piroxicam was the only compound found to be toxic in the iMPCC model but not in the MPCC model, likely due to donor-to-donor differences in toxicities. Still, eleven compounds were not identified as toxic with either primary hepatocytes or iHeps.

Figures 3A, 3B:
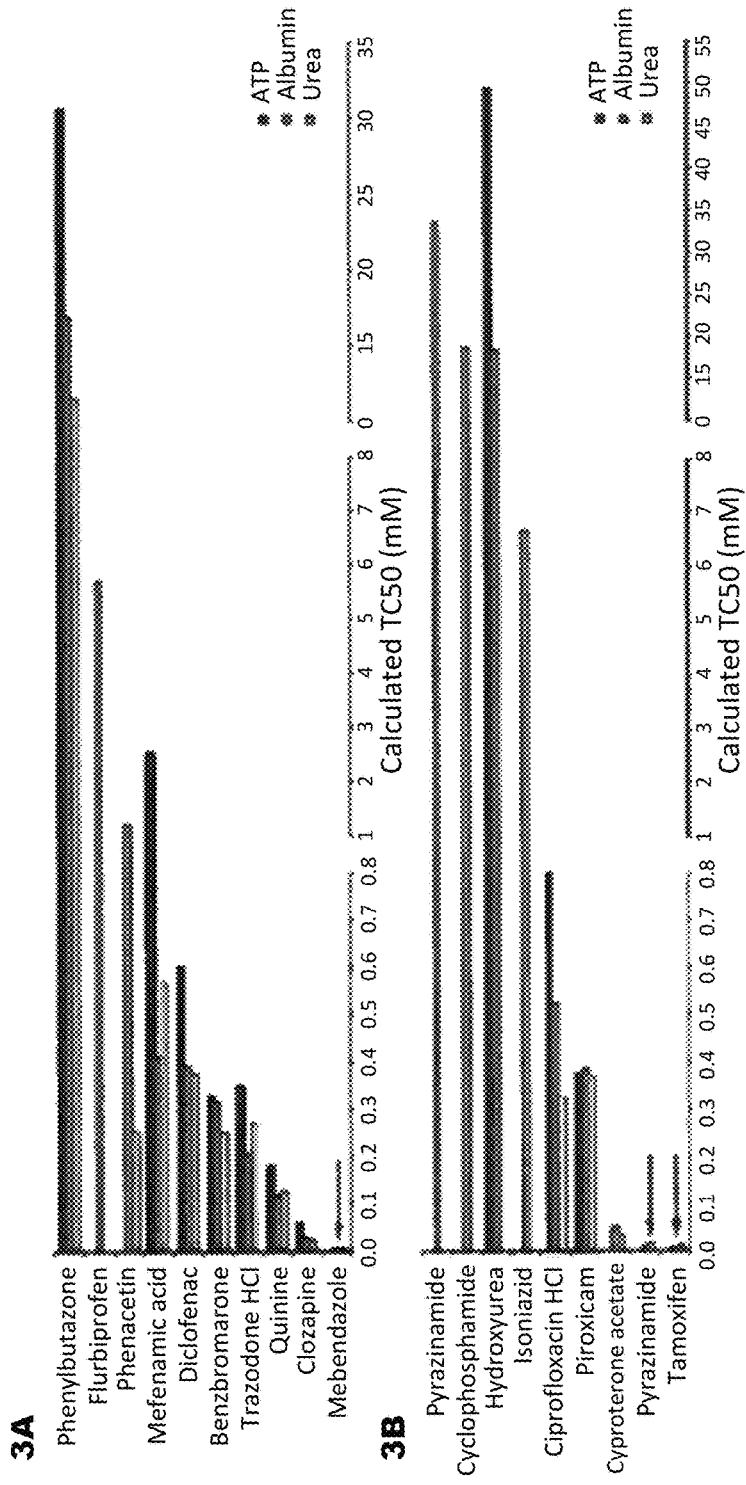

Also of note are the comparison of primary hepatocyte sandwich culture data to iCCs (Table 3, below) and the TC50 values of true positive compounds (FIG. 3A). Notable differences between iCC and iMPCCs are cyproterone acetate, isoniazid, and pyrazinamide, which were all identified as toxic in iMPCCs but non-toxic in iCCs. Of the 13 toxic compounds we tested that were picked up in iMPCCs, iCCs picked up only 8, suggesting a reduction in sensitivity in the iCC model (Table 3, below). This demonstrates the utility of the iMPCC model over iCCs. Phenacetin, despite being picked up in all other model systems, was not identified as toxic in iCCs. Comparing urea TC50 values shows a higher TC50 in iHeps with phenylbutazone, flurbiprofen, diclofenac, and benzbromarone, yet a higher TC50 in primary hepatocytes with the other true positives (Table 4, below). Like the HUM4011 primary hepatocyte data, these all point to donor-to-donor variability, a major drawback of toxicity screens in primary hepatocytes overall.

Similar to primary hepatocytes, the iMPCC model system also has the ability to is distinguish between structural analogs. The anti-Parkinson's drugs tolcapone and entacapone show both time- and dose-dependent toxicities (FIG. 3C), likely due to differences in marker analytes. Comparable results were seen with the diabetes drugs troglitazone (withdrawn by the FDA) and rosiglitazone (FDA approved) (Table 1; FIGS. 9A and 9B). As a demonstration of the power of predicting drug-drug interactions and mechanistic studies, we co-incubated acetaminophen (APAP, an analgesic with the toxic intermediate NAPQI) with L-buthionine (S,R)-sulfoximine (BSO, a glutathione depleting agent) at 200 µM. This co-incubation was designed to knockout a primary method for NAPQI detoxification through glutathione. APAP doses of 25·Cmax and 50·Cmax showed a substantial increase in toxicity when combined with BSO (FIG. 3D), demonstrating the applications for predicting drug-drug interactions and toxicity.

TABLE 2

Additional data for compounds tested

| Compound name | $C_{max}$ (µM)[25] | FW (g/mol) | DMSO (%) |
|---|---|---|---|
| *True positives in HIAT* | | | |
| Acetaminophen | 151.17 | 138.91 | 0.2 |
| Amiodarone | 0.806 | 681.80 | 0.1 |
| Benzbromarone | 4.361 | 424.10 | 0.1 |
| Clozapine | 0.951 | 326.83 | 0.1 |
| Diclofenac | 8.023 | 318.10 | 0.1 |
| Flurbiprofen | 57.356 | 244.27 | 0.1 |
| Mebendazole | 0.126 | 295.30 | 0.1 |
| Mefenamic acid | 26.959 | 241.30 | 0.2 |
| Phenacetin | 13.401 | 179.22 | 1.0 |
| Phenylbutazone | 486.772 | 308.37 | 1.0 |
| Quinine | 9.254 | 391.47 | 0.2 |
| Trazodone HCl | 5.065 | 408.32 | 0.1 |
| Troglitazone | 6.387 | 441.50 | 0.1 |
| *True negatives in HIAT* | | | |
| Aspirin | 5.526 | 180.16 | 0.1 |
| Buspirone | 0.005 | 421.98 | 0.1 |
| Dexamethasone | 0.224 | 392.47 | 0.1 |
| Dextromethorphan HBr | 0.028 | 370.30 | 0.1 |
| Fluoxetine | 0.049 | 345.79 | 0.1 |
| Lidocaine | 36.296 | 288.81 | 0.1 |
| Miconazole | 0.024 | 479.10 | 0.1 |
| Prednisone | 0.068 | 358.43 | 0.1 |
| Propranolol | 0.201 | 295.81 | 0.1 |
| Rosiglitazone | 1.120 | 357.43 | 0.1 |
| Warfarin | 4.888 | 308.34 | 0.1 |
| *False negatives in HIAT* | | | |
| Acetazolamide | 135.142 | 222.25 | 0.2 |
| Betahistine 2HCl | 0.004 | 209.12 | 0.1 |
| Captopril | 4.284 | 217.29 | 0.1 |
| Chloramphenicol palmitate | 19.991 | 561.54 | 0.1 |
| Ciprofloxacin HCl | 11.476 | 331.34 | 0.1 |
| Clomiphene citrate | 0.022 | 598.10 | 0.1 |
| Clomipramine | 0.191 | 351.30 | 0.1 |
| Cyclophosphamide | 265.359 | 279.10 | 0.2 |
| Cyproterone acetate | 0.656 | 416.94 | 0.1 |
| Danazol | 0.074 | 337.50 | 0.1 |
| Dapsone | 6.007 | 248.30 | 0.1 |
| Estrone | 0.022 | 270.37 | 0.1 |

TABLE 2-continued

Additional data for compounds tested

| Compound name | $C_{max}$ (µM)[25] | FW (g/mol) | DMSO (%) |
|---|---|---|---|
| Hydroxyurea | 793.925 | 76.05 | 0.2 |
| Imipramine HCl | 0.087 | 316.87 | 0.1 |
| Isoniazid | 76.609 | 137.14 | 0.1 |
| Maleic acid | 1.000 | 180.04 | 0.1 |
| Methimazole | 1.868 | 114.17 | 0.1 |
| Nifedipine | 0.271 | 348.30 | 0.1 |
| Norgestrel | 0.009 | 312.45 | 0.1 |
| Nortriptyline HCl | 0.122 | 299.84 | 0.1 |
| Phentolamine mesylate | 0.086 | 377.47 | 0.1 |
| Piroxicam | 5.135 | 331.37 | 0.1 |
| Progesterone | 0.193 | 314.46 | 0.1 |
| Pyrazinamide | 407.174 | 123.11 | 1.0 |
| Tamoxifen | 0.162 | 371.53 | 0.1 |

TABLE 3

Comparison of binary decisions in iCCs and iMPCCs

| | DILI | | | Model predictions | | |
|---|---|---|---|---|---|---|
| Compound name | Sev | Cat | Clin | Sand | iCC | iMPCC |
| *True positives in HIAT* | | | | | | |
| Benzbromarone | −2 | P1 | + | + | + | + |
| Clozapine | 2 | P2 | + | + | + | + |
| Diclofenac | 7 | P2 | + | + | + | + |
| Flurbiprofen | 3 | P2 | + | + | + | + |
| Phenacetin | N/A | P2 | + | + | − | + |
| *True negatives in HIAT* | | | | | | |
| Aspirin | N/A | O2 | − | − | − | − |
| Dexamethasone | 3 | N1 | − | − | − | − |
| Dextromethorphan HBr | N/A | N1 | − | − | − | − |
| Warfarin | 5 | N2 | − | − | − | − |
| *False negatives in HIAT* | | | | | | |
| Ciprofloxacin HCl | 7 | P2 | + | − | + | + |
| Cyclophosphamide | 5 | P2 | + | − | + | + |
| Cyproterone acetate | N/A | O1 | + | − | − | + |
| Hydroxyurea | 8 | P2 | + | − | + | + |
| Isoniazid | 8 | P1 | + | − | − | + |
| Piroxicam | 3 | P2 | + | − | + | + |
| Pyrazinamide | 3 | P2 | + | − | − | + |
| Tamoxifen | 6 | P2 | + | − | − | + |

Table 3 Notes.
The Sev column lists the DILI severity scores from the LTKB of the FDA, where N/A means not applicable/no information in the database; a negative number, the drug was withdrawn from the market; higher positive numbers, greater DILI concern; and three dashes, no DILI concern.
DILI categories (Cat column):
P1, DILI type 1, dose dependent (toxic);
P2, DILI type 2, idiosyncratic (toxic);
N1, not known to cause liver injury (nontoxic);
N2, sporadic cases (<10) of liver injury reported but generally considered safe drug to use by doctors (nontoxic);
O1, hepatotoxic in animals untested in humans (toxic);
O2, elevated liver enzymes observed in humans but does not lead to frank liver toxicity (nontoxic).
The right four columns compare clinical DILI (Clin) with binary decisions in sandwich cultures (Sand), MPCCs, and iMPCCs.

TABLE 4

Comparison of TC50 values in MPCCs and iMPCCs

|  | TC50 in MPCCs (μM)[19] | | | TC50 in MPCCs (μM) | | |
| --- | --- | --- | --- | --- | --- | --- |
| Compound name | ATP | Albumin | Urea | ATP | Albumin | Urea |
| True positives in HIAT | | | | | | |
| Benzbromarone | 15.1 | 31.3 | 27.9 | 332.5 | 316.5 | 249.8 |
| Clozapine | 48.6 | 39.6 | 40.4 | 57.9 | 27.8 | 20.9 |
| Diclofenac | 638.4 | 141.9 | 206.2 | 602.1 | 391.5 | 378.3 |
| Flurbiprofen | 3351.1 | 2406.8 | 2459.0 | N/A | 5683.4 | N/A |
| Mebendazole | 11.5 | 11.6 | N/A | N/A | 1.9 | 2.3 |
| Mefenamic acid | 1393.4 | 1291.9 | 1255.1 | 2551.9 | 410.3 | 572.3 |
| Phenacetin | N/A | N/A | 1076.1 | N/A | 1213.3 | 253.3 |
| Phenylbutazone | 7566.7 | 6414.4 | 2532.0 | 30720.2 | 16968.9 | 11497.6 |
| Quinine | 259.1 | 251.6 | 285.2 | 182.2 | 115.7 | 127.9 |
| Trazodone HCl | 201.7 | 64.8 | 121.8 | 351.5 | 205.5 | 272.4 |
| False negativs in HIAT | | | | | | |
| Ciprofloxacin HCl | 285.4 | 160.0 | 320.2 | 804.2 | 525.3 | 326.3 |
| Clomipramine | 12.0 | 9.4 | 9.9 | N/A | 9.4 | 13.8 |
| Cyclophosphamide | 6165.0 | 1449.4 | 1746.0 | N/A | 18670.7 | N/A |
| Cyproterone acetate | 39.1 | N/A | 41.0 | N/A | 51.0 | 33.1 |
| Hydroxyurea | 7407.0 | 28616.2 | 19647.8 | 49358.3 | 18398.4 | N/A |
| Isoniazid | N/A | N/A | 4579.6 | N/A | 6681.5 | N/A |
| Pyrazinamide | 19695.5 | 20420.3 | 14781.6 | N/A | 33457.5 | N/A |
| Tamoxifen | 15.8 | 3.2 | 3.9 | N/A | 4.2 | 11.7 |

Table 4 Note.
N/A indicates that a TC50 value (the interpolated concentration at which activity decreases by 50% of DMSO-only controls) could not be calculated.

Example 6

Drug-mediated CYP Enzyme Induction in iMPCCs

Another important aspect to utilizing iHeps for drug development is their ability to undergo drug-mediated CYP enzyme induction. CYP enzyme induction was assessed as follows. Stock solutions of the prototypic CYP450 inducer rifampicin (Sigma) were made in dimethylsulfoxide (DMSO) and phenobarbital (Sigma) was dissolved in water. Cultures were treated with inducers (rifampin at 25 μM and phenobarbital at 1 mM) dissolved in hepatocyte culture medium for 4 days. Control cultures were treated with vehicle (DMSO) alone for calculations of fold induction. To enable comparisons across inducers, DMSO levels were kept constant at 0.1% (v/v) for all conditions.

Figure 10:
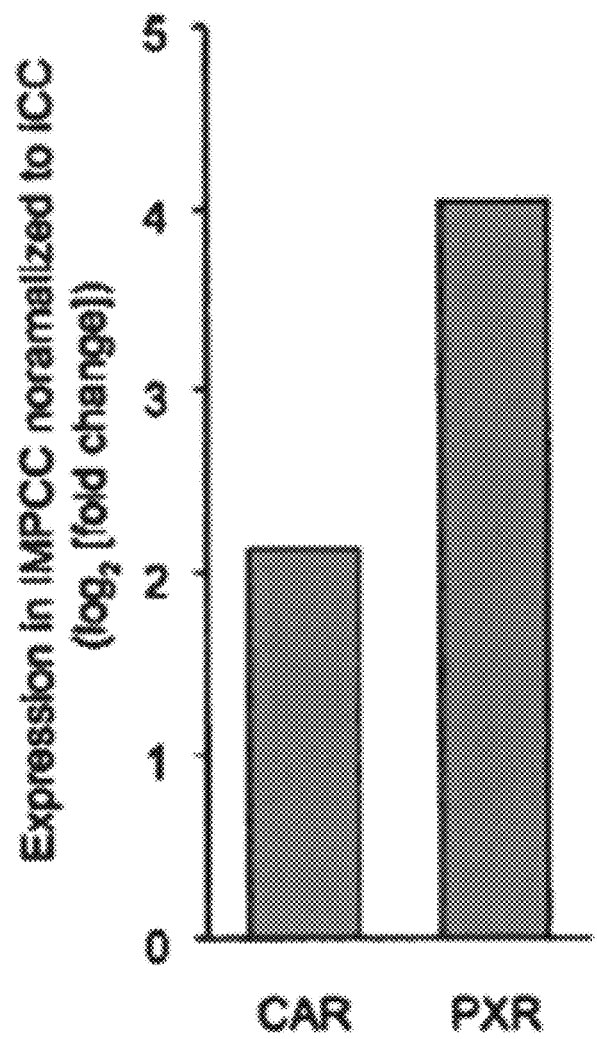
FIG. 10 Nuclear receptor gene expression in iMPCCs. Quantitative comparison of liver nuclear receptor mRNA in iMPCC vehicle-only controls to mRNA in iCC vehicle-only controls (day 22). All data was normalized to the reference gene, GAPDH. Constitutive androstane receptor, CAR (NR1I3), pregnane x receptor, PXR (NR1I2).
Figure 11:
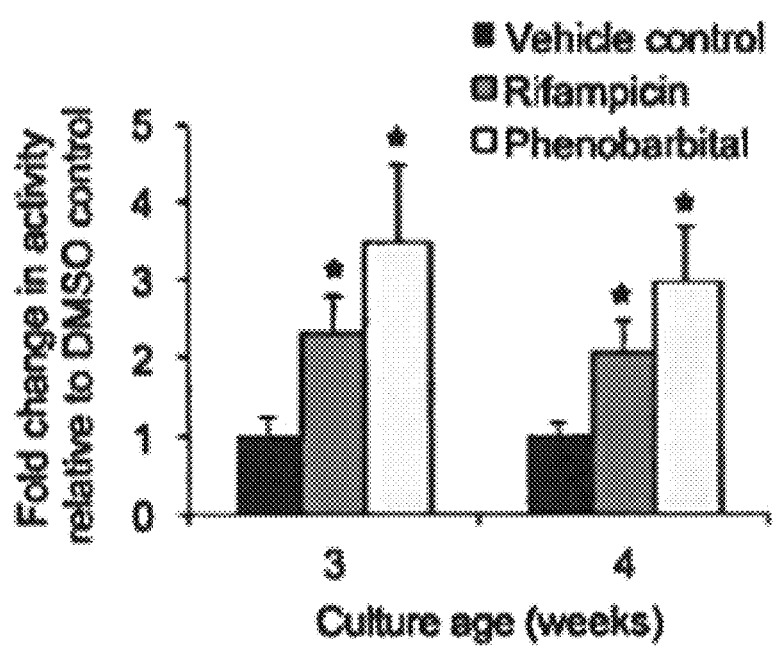
FIG. 11 Repeat induction. Rifampicin (25 µM) and phenobarbital (1 mM) mediated induction of CYP2C9 and CYP3A4 gene expression and functional activity in iMPCCs. Cultures were treated with inducers for 4 d before incubation with CYP-specific luminescence-based substrates (day 22). Following 6 d of normal culture, iMPCCs were induced again for 4 d and the functional CYP assay repeated (day 32). Data from representative study shown. All error bars represent s.d. (n=3). *p<0.05.

The iMPCC model exhibited inducible CYP2C9 and CYP3A4 gene expression and significant increases in functional activity levels in response to both rifampicin (FIG. 3E) and phenobarbital (FIG. 3F) treatment. Meanwhile, conventionally cultured iHeps is only showed induced functional activity in the presence of phenobarbital, albeit at much lower levels than iMPCCs. Functional induction by rifampicin in iMPCCs and lack thereof in iCCs may be partly explained by the differential expression of pregnane X receptor, PXR, and the constitutive androstane receptor, CAR, two nuclear receptors responsible for CYP enzyme induction (FIG. 10). Rifampicin is known to regulate the induction of CYP3A4 and CYP2C9 through PXR and the PXR responsive element (PXRRE), while phenobarbital has been shown to regulate CYP enzymes through both PXR dependent and independent mechanisms, namely through CAR and the phenobarbital responsive element module (PBREM). To show reusability of the iMPCC model, induction assays were repeated within the same cultures and CYP3A4 activity was induced a second time to a similar degree (FIG. 11).

Figure 12A:
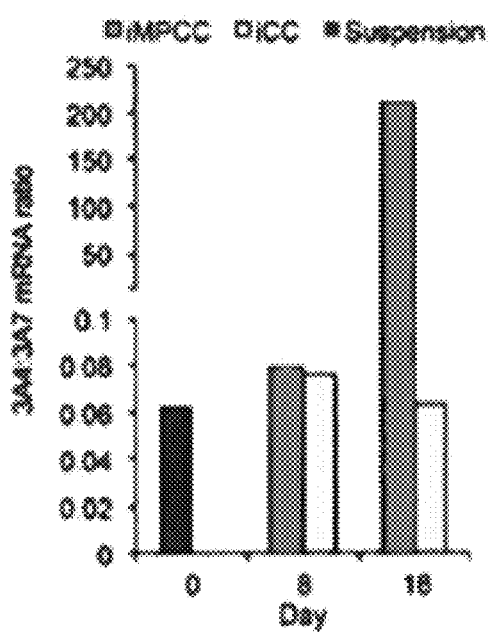
FIGS. 12A and 12B Hepatic maturation of iHeps in iMPCCs.
Figure 12B:
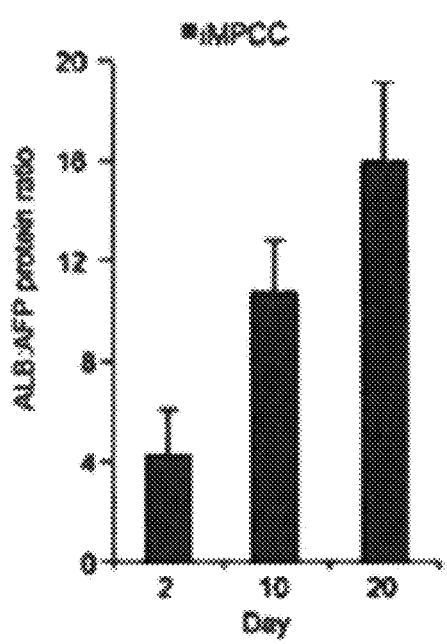

The ratio of two important hepatic maturation factors to their corresponding fetal forms was also examined. Temporal gene expression analysis showed increasing ratios of CYP3A4 to CYP3A7 in the iMPCC model while conventionally cultured iHeps did not show this increase (FIG. 12A). Likewise, the ratio of secreted albumin to alphafetoprotein (AFP) displayed increasing levels in iMPCCs (FIG. 12B).

Figure 13:
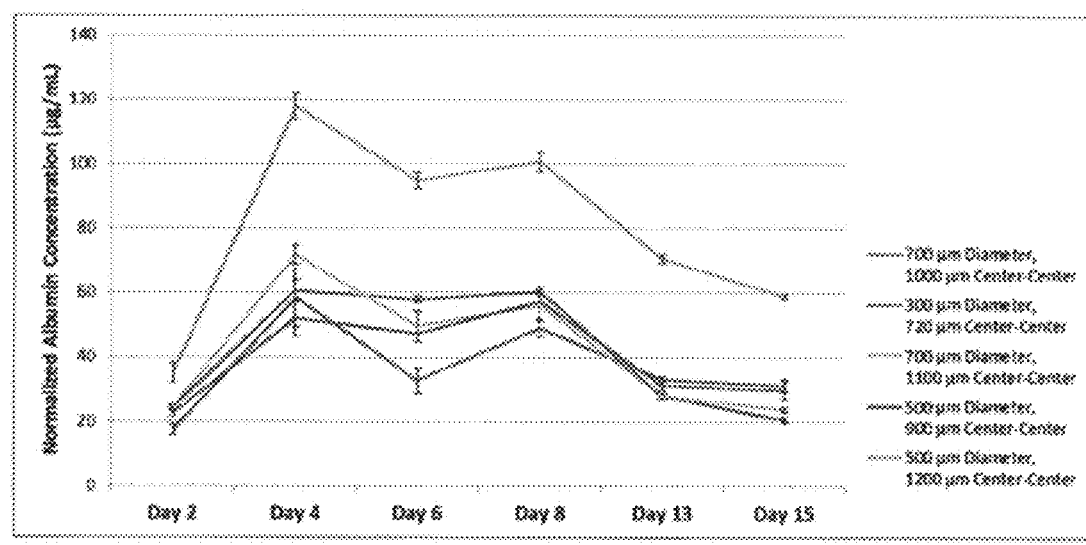
FIG. 13 Time course albumin data for various architectures. Data normalized to DAPI cell counts. Architecture dimensions are given as the island diameter (µm) and center-to-center island spacing (µm).
Figure 14:
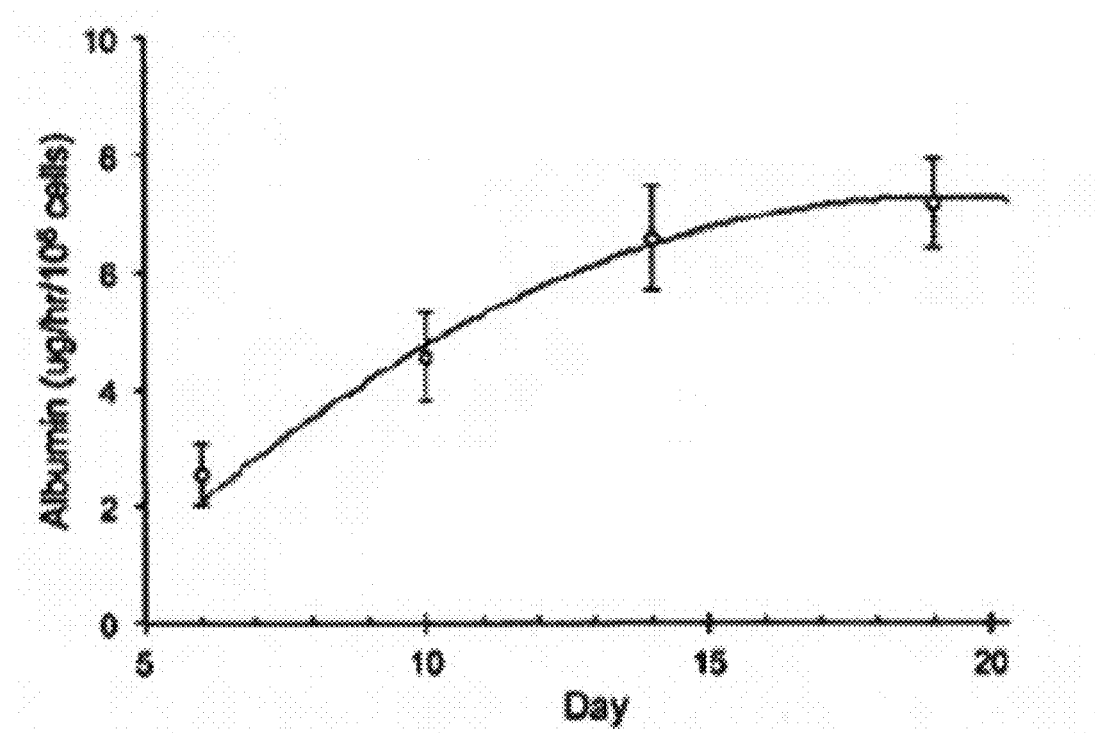
FIG. 14 Functional stabilization of cryopreserved iHeps, showing increase in albumin production levels and stabilization over time.

Modulation of co-culture architecture indicates that a 500 μm microdot (island) diameter with a 1200 μm center-to-center spacing worked best for preserving hepatic function in the stem-cell derived hepatocytes (FIG. 13). The iMPCC model was also shown to induce high levels of hepatic function in cryopreserved iHeps (FIG. 14), thereby allowing on-demand creation of cultures for drug testing in the future.

The results indicate that micropatterned co-cultures of iHeps and stromal fibroblasts increase a diversity of liver-specific functions for several weeks and are amenable to 96-well format, allowing for increased screening capabilities. The disclosed iMPCC model is compatible with in situ image-based and plate reader-based assays and approaches primary human hepatocytes in its prediction of DILI.

Example 7

Engineering the iMPCC Platform

Figure 31A:
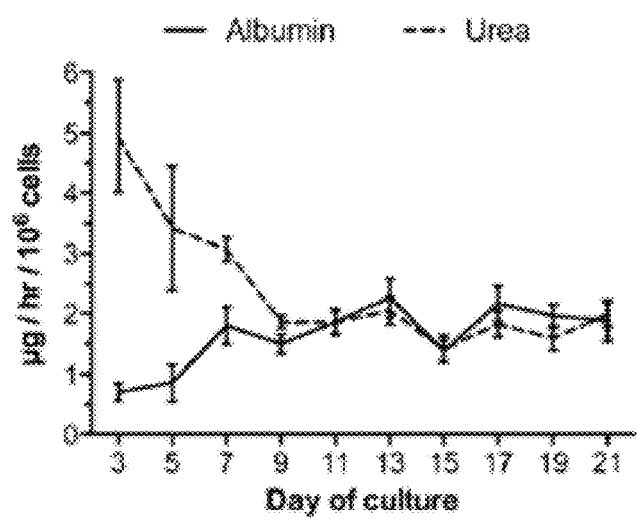
FIGS. 31A and 31B iMPCCs created from another donor of cryopreserved iHeps.
Figure 31B:
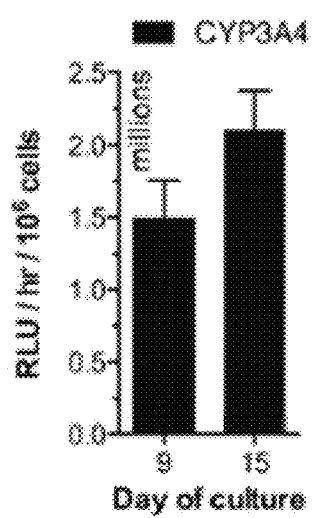

Cellular Dynamics International (CDI, Madison, Wis.) generated ~95% pure iHeps as assessed via α1-antitrypsin using a proprietary differentiation protocol. Per is information provided by CDI, Donor 1 is a Caucasian female and iPSCs were reprogrammed from fibroblasts, while donor 2 is a Caucasian male and iPSCs were reprogrammed from peripheral blood mononuclear cells. The current and all following examples here were conducted with fresh or cryopreserved iHeps differentiated from donor 1 cells, except for the example in (FIGS. 31A and 31B), which utilized donor 2.

Fresh iHeps were processed according to manufacturer's instructions. Briefly, fresh iHep aggregates were pelleted via centrifugation, dissociated with 0.5% trypsin-EDTA (Life Technologies, Carlsbad, Calif.), and cellular debris was removed using KryoThaw (SciKon Innovation, Durham, N.C.). iHeps were diluted in Roswell Park Memorial Institute 1640 medium (Life Technologies), containing 1 μM dexamethasone (Sigma-Aldrich, St Louis, Mo.), 2% v/v B27 (Life Technologies), 1% v/v penicillin/streptomycin (Cellgro, Manassas, Va.), and 20 ng/mL oncostatin-M (R&D Systems, Minneapolis, Minn.). Cryopreserved iHeps were processed according to manufacturer protocols.

Figure 15A:
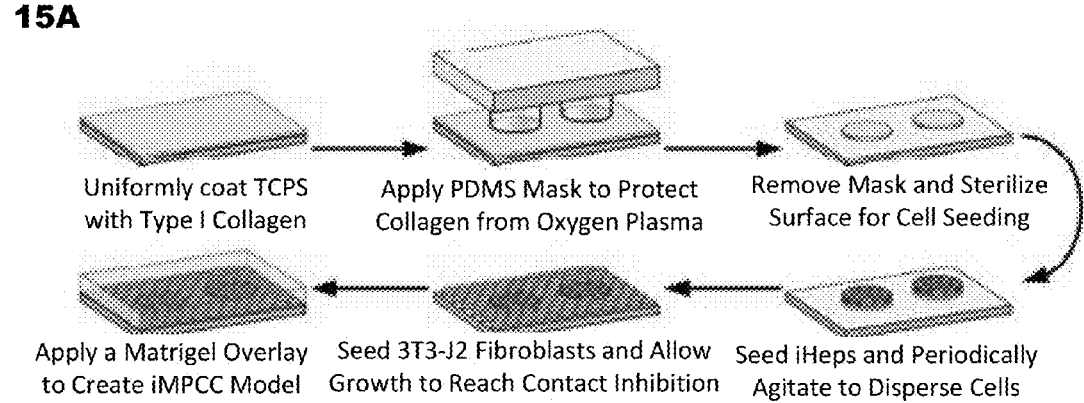
FIGS. 15A and 15B Development of the iHep-based micropatterned co-culture (iMPCC) platform.
Figure 15B:
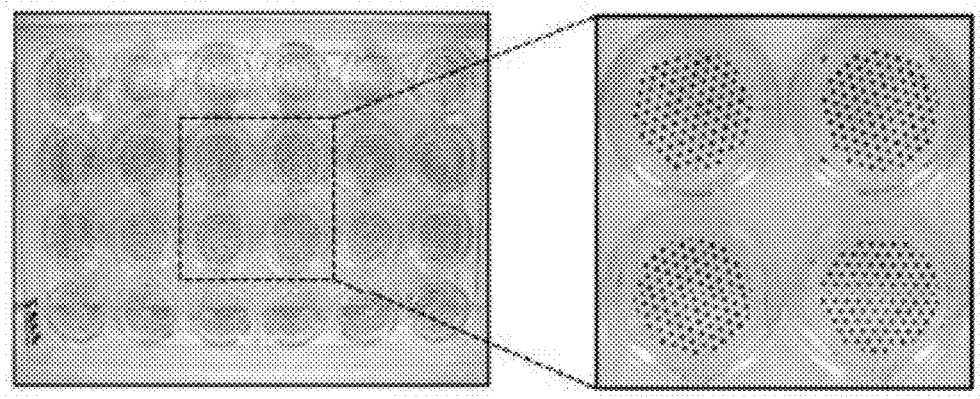
Figure 23:
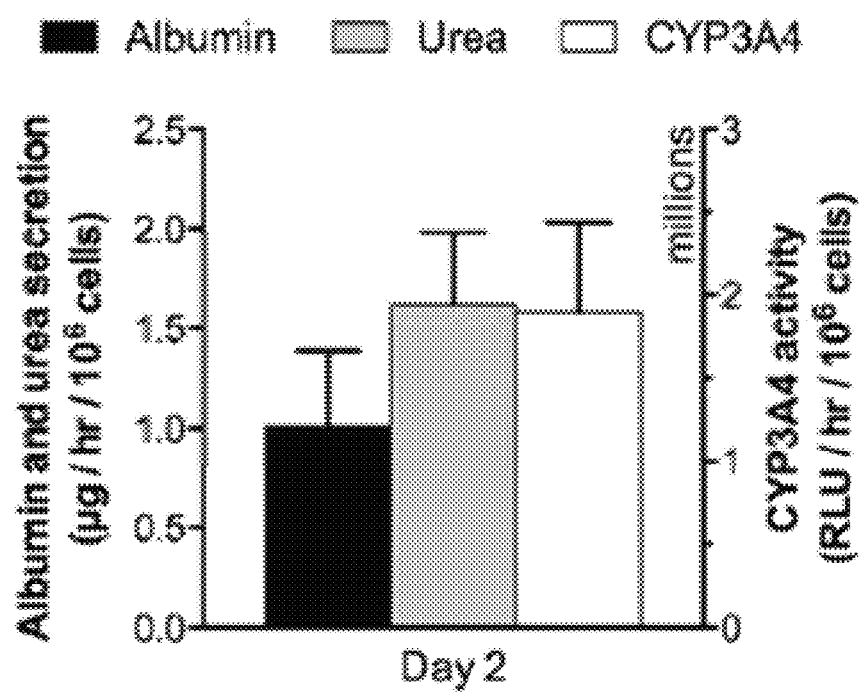
FIG. 23 Characterization of iHep batches received from Cellular Dynamics International (CDI, Madison, Wis.). Average albumin production, urea secretion, and CYP3A4 activity (luciferin-IPA from Promega, Madison, Wis.) across three independent batches of micropatterned iHeps without fibroblasts after 48 hours of culture. All error bars represent standard deviation (n=3). Gene expression analysis of iHep batches (n=3) also verified the presence of mature hepatocyte markers including ALB (albumin), HNF4A (hepatocyte nuclear factor 4-alpha), HNF6 (hepatocyte nuclear factor 6), A1AT (α1-antitrypsin, SERPINA10), OATP2 (solute carrier organic anion transporter family, member 1B1, SLCO1B1), TAT (tyrosine aminotransferase), and TDO2 (tryptophan 2,3-dioxygenase) (data not shown).
Figure 24:
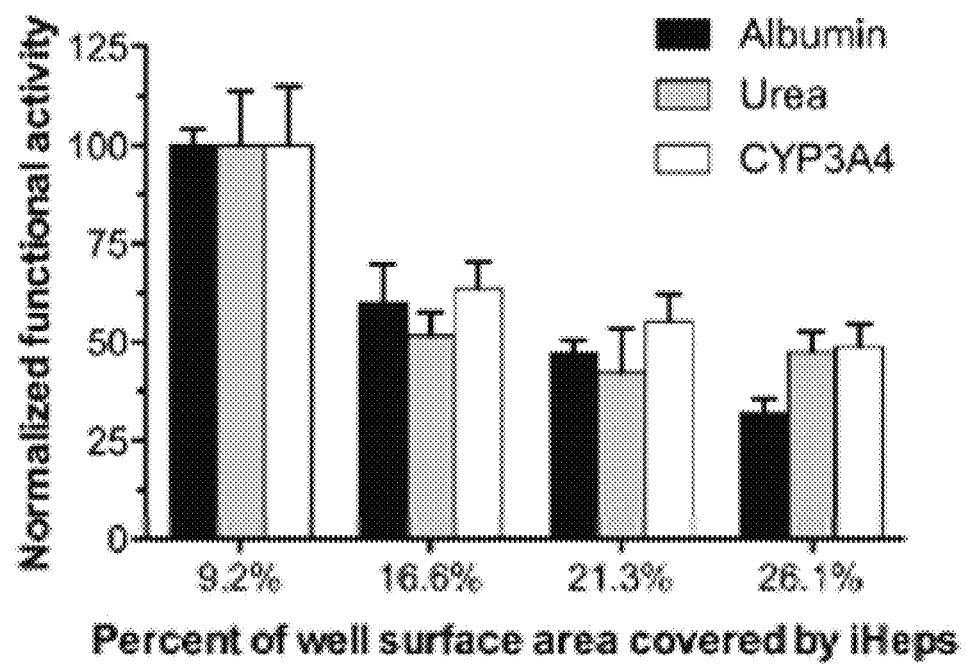
FIG. 24 Effect of island geometry on iMPCC functions. Different micropatterned geometries allowed iHeps to cover 9.2% (500 µm diameter, 1200 µm is center-center spacing), 16.6% (500 µm diameter, 900 µm center-center), 21.3% (700 µm diameter, 1100 µm center-center), or 26.1% (700 µm diameter, 1000 µm center-center) of the available surface area in each well of a 24-well plate. All cultures were then surrounded by 3T3-J2 murine embryonic fibroblasts within 24 hours of iHep seeding. Albumin, urea, and CYP3A4 functions at a representative time point (day 15) are shown. Data was normalized to the 9.2% geometry (500 μm diameter, 1200 μm center-center spacing). All error bars represent standard deviation (n=3).
Figure 25:
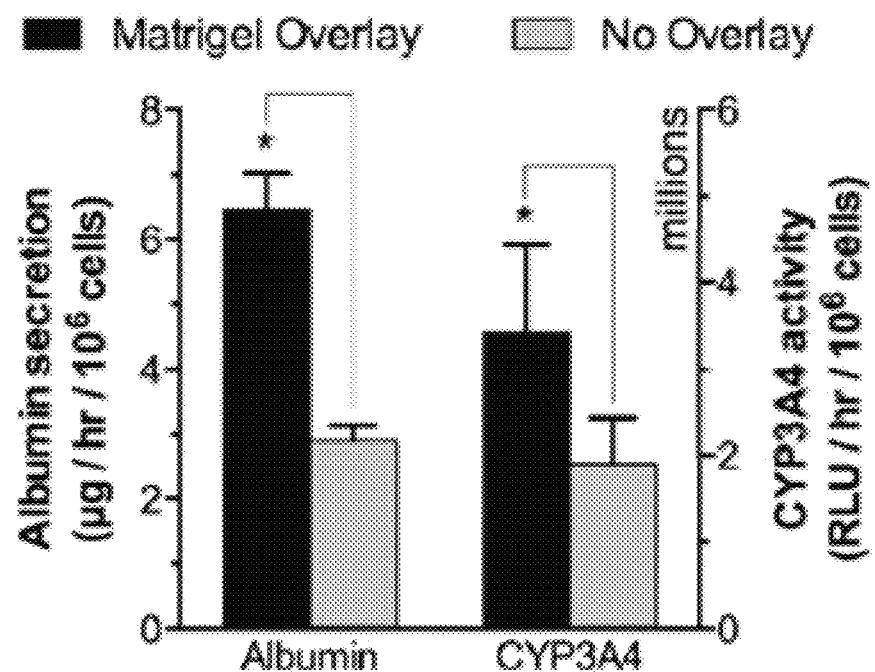
FIG. 25 Matrigel™ overlay enhances iHep liver functions in the iMPCC model. Day 6 of culture is shown, but trends were seen for several weeks. All error bars represent standard deviation (n=3). *p<0.05.

Characterization of liver gene expression and functions indicated that commercial cell batches from Cellular Dynamics International (CDI) were reproducibly iHeps (FIGS. 23). Polydimethylsiloxane (PDMS) masks were applied as described above and elsewhere to simultaneously micropattern rat tail type-I collagen into all wells of a tissue culture polystyrene plate (FIG. 15). Following selective attachment of iHeps to collagen domains, 3T3-J2 murine embryonic fibroblasts were seeded in the surrounding areas within 24 hours to create iMPCCs. The island diameter and spacing were optimized for iMPCCs, with higher liver functions observed when less of the surface area in each well was occupied by iHeps relative to the area available for fibroblast growth (FIG. 24). Overlaying iMPCCs with Matrigel™ further improved liver functions (FIG. 25).

The iHeps that attached to collagen domains were positive for both albumin and glycogen (FIG. 16A). In iMPCCs, iHep morphology improved (polygonal shape, bile canaliculi, distinct nuclei/nucleoli) and was maintained for 4 weeks (FIG. 16B). In contrast, density matched micropatterned iHep cultures without fibroblasts (iMPH) displayed a de-differentiated (i.e. spread-out) morphology. Additionally, iHeps in iMPCCs became polarized as assessed by excretion of a fluorescein dye into the bile canaliculi between cells and uptake of fluorescent low-density lipoprotein (LDL) into the cytoplasm (FIG. 16C). The bile canaliculi network was not completely formed around all iHeps, which is also observed with PHHs.

Example 8

Liver Gene Expression and Functions in IHep Cultures

Profiles were prepared of gene expression in iMPCCs relative to pure iHep conventional confluent cultures with a Matrigel™ overlay (iCCs). Human-specific transcripts representing liver maturation factors and CYP450 enzymes involved in drug metabolism and toxicity (FIG. 17A) were measured. iMPCCs were found to have significantly higher expression for most of the liver transcripts compared to both iCCs and the starting material from CU, thereby suggesting a more highly differentiated phenotype in iMPCCs. Additionally, the expression levels of most genes were maintained for several weeks in iMPCCs. The two exceptions were arginase 1 (urea cycle enzyme) and CYP2D6, which were down-regulated in both iMPCCs (~1.7 fold for arg1, ~1.9 fold for CYP2D6) and iCCs (~20 fold for arg1, ~2.9 fold for CYP2D6) by the third week of culture relative to the starting material. However, the rate of decline of these liver markers was highly dependent on the culture method, as also has been observed with PHHs.

Figures 17A, 17B:
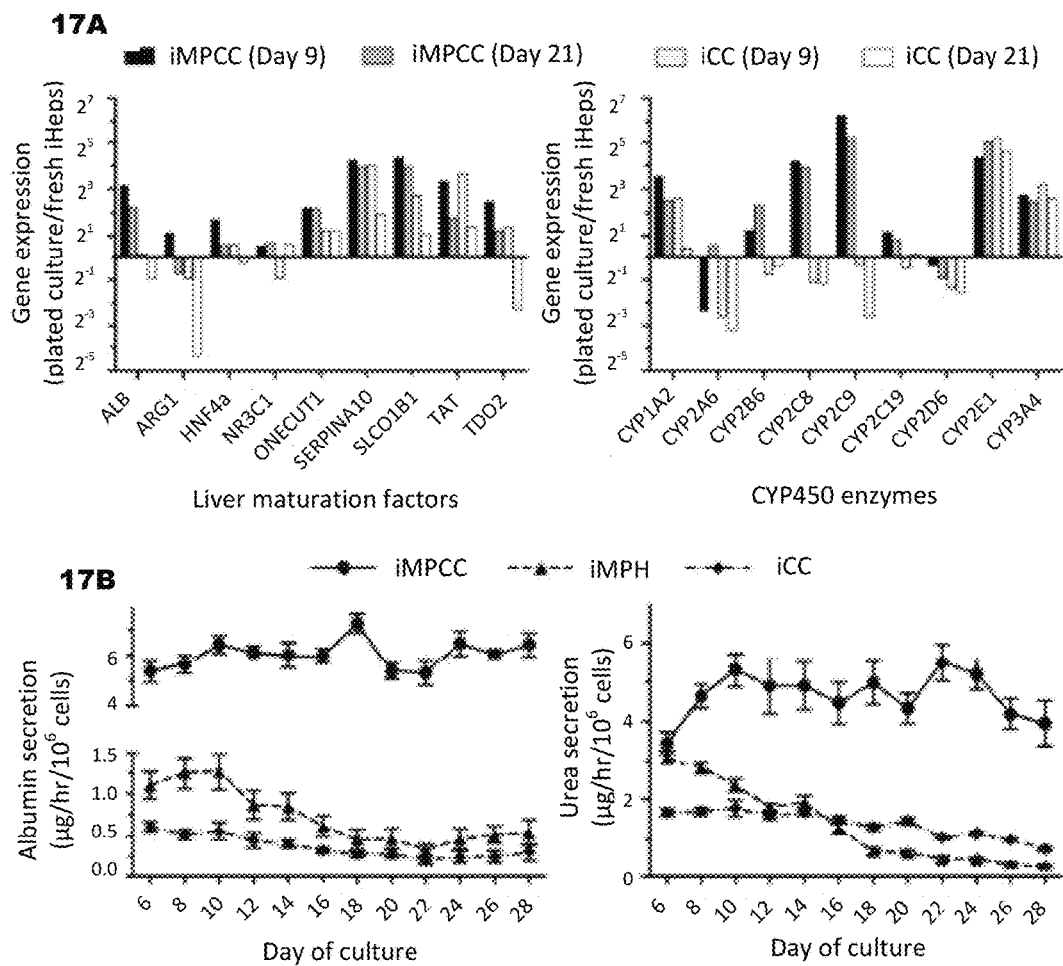
FIGS. 17A and 17B Liver gene expression and synthesis functions in iHeps.
Figure 18A:
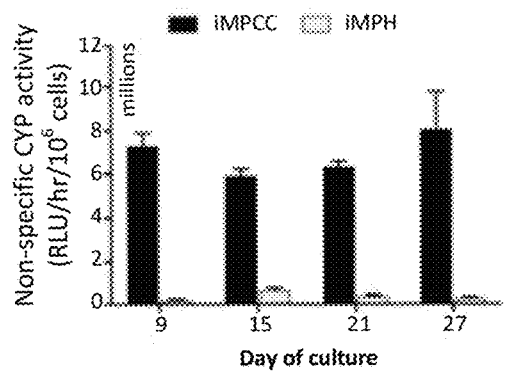
FIGS. 18A, 18B, 18C and 18D Activities of drug metabolism enzymes in iHeps.
Figure 18B:
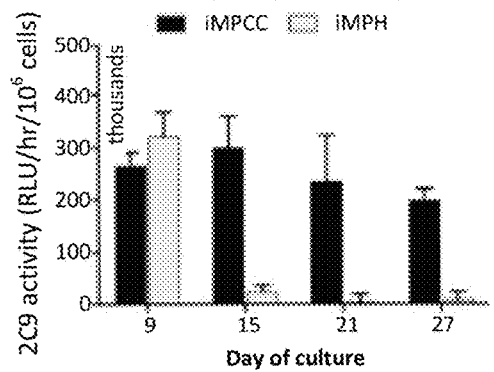
Figure 18C:
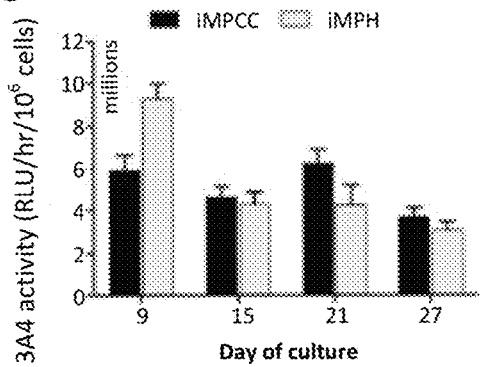
Figure 18D:
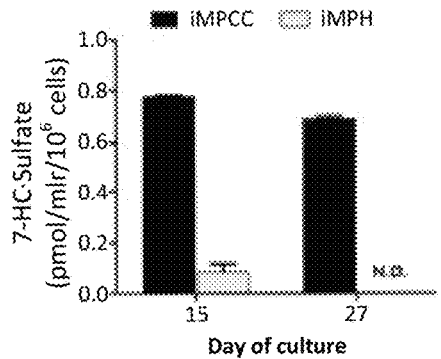
Figures 26A, 26B:
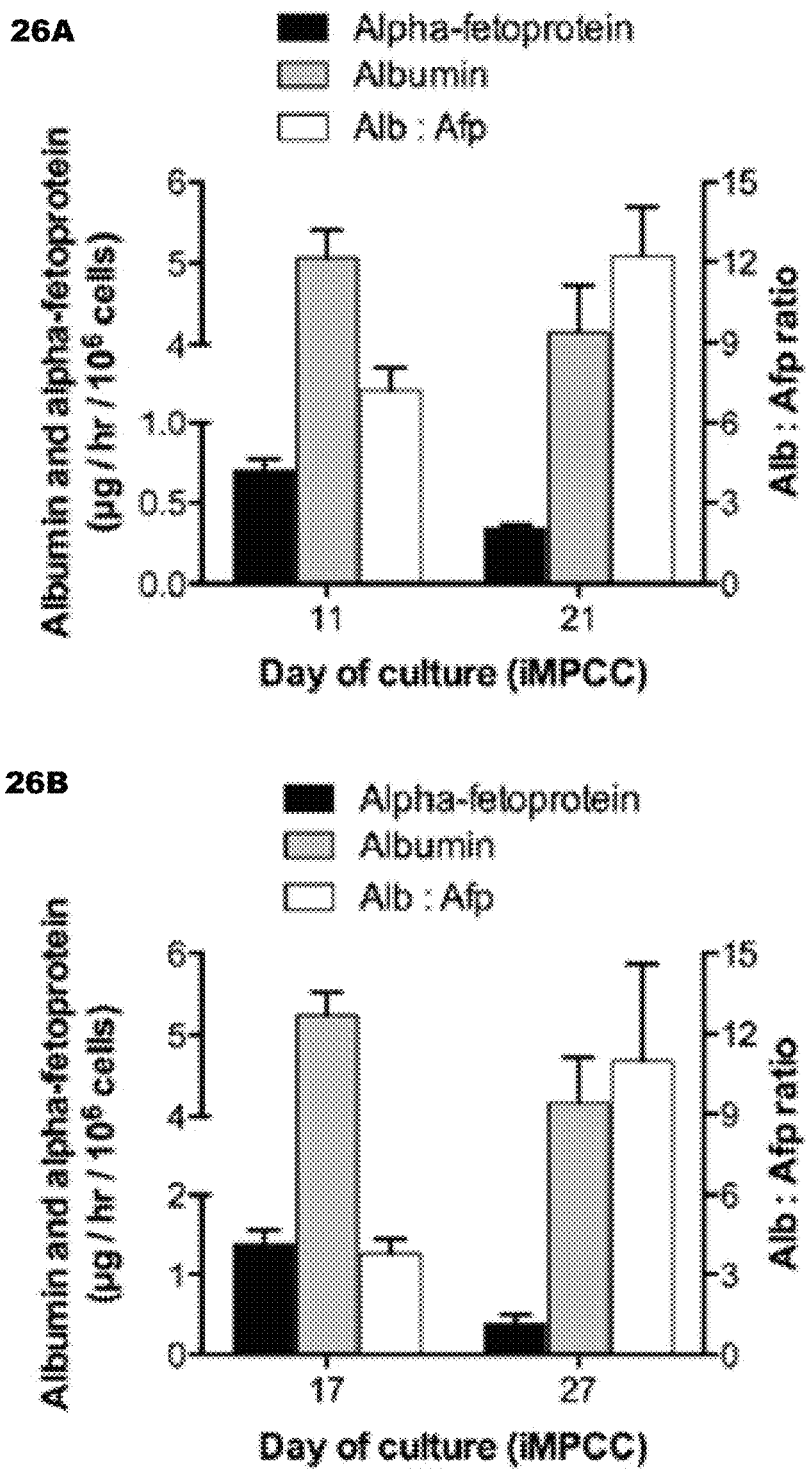
FIGS. 26A and 26B Hepatic maturation of iHeps in iMPCCs. Stabilized albumin (Alb) production and declining alpha-fetoprotein (Afp) production in iMPCC supernatants collected from FIG. 26A fresh iHeps and FIG. 26B cryopreserved iHeps, both from the same donor #1 (see methods for information on donors). All error bars represent standard deviation (n=3).
Figure 27:
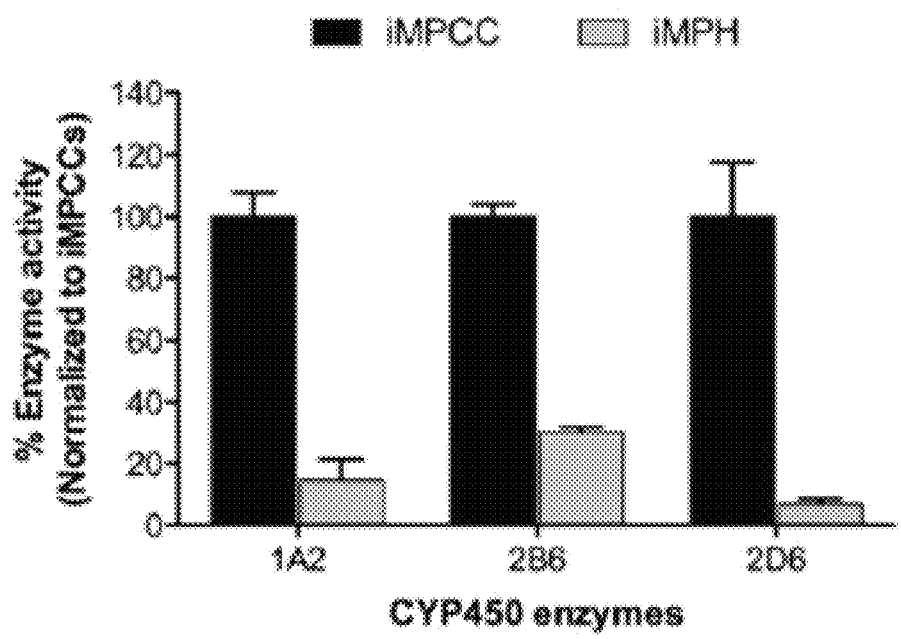
FIG. 27 CYP450 characterization of iHeps in iMPCCs and iMPHs using FDA-approved substrates requiring LC-MS/MS quantitation. Data from day 15 for iMPCCs and iMPHs (micropatterned iHeps without fibroblasts) are shown, yet trends were seen over multiple time-points. Enzyme, substrate, metabolite measured: 1A2, phenacetin, acetaminophen; 2B6, bupropion HCl, hydroxybupropion; and 2D6, dextromethorphan, dextrorphan. All error bars represent standard deviation (n=3).
Figure 28:
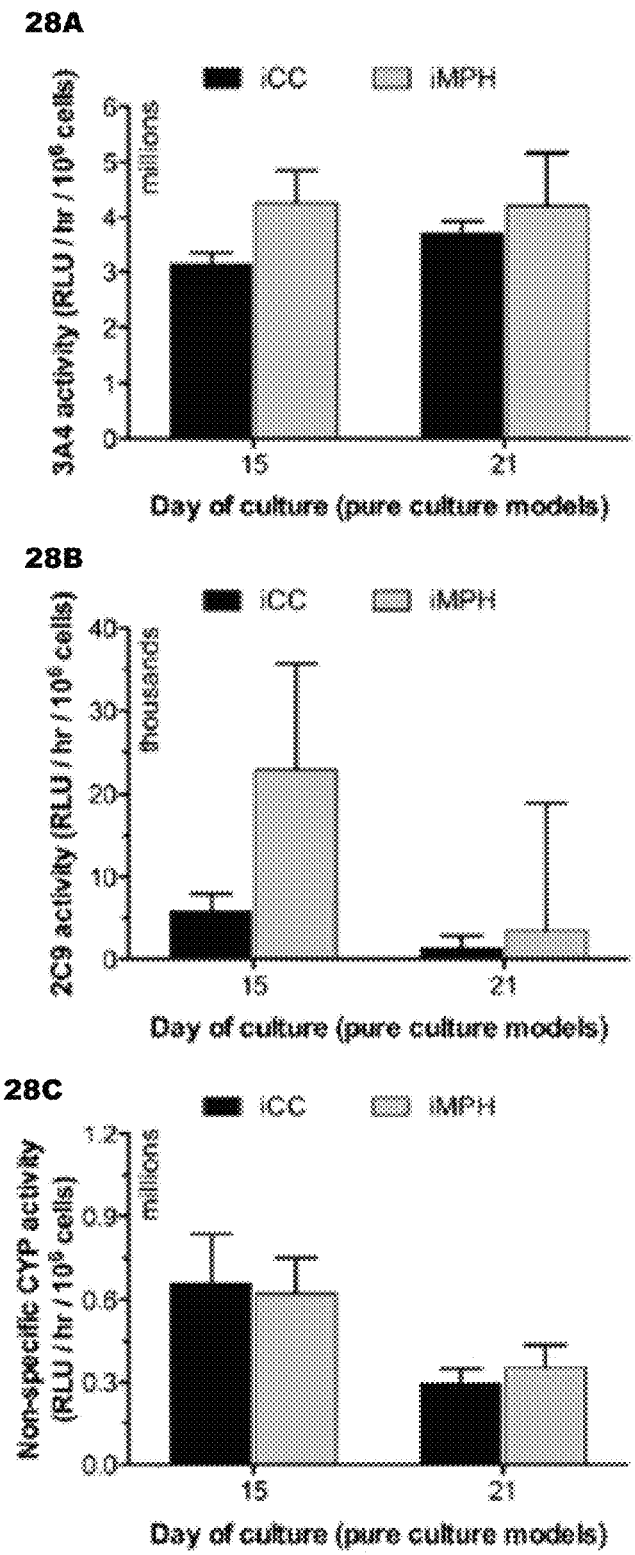
FIGS. 28A, 28B and 28C CYP450 characterization of iHeps in iCCs and iMPHs using luminescent-based substrates. Time-course of FIG. 28A CYP3A4, FIG. 28B CYP2C9, and FIG. 28C non-specific CYP450 activities (cleaved by CYP1A1, 1A2, 2B6, and 2D6) in micropatterned pure iHep cultures without fibroblasts (iMPHs), and conventional confluent iHep cultures with Matrigel™ overlay (iCCs) via assessment with luminescent assays (Promega). All error bars represent standard deviation (n=3).
Figure 29:
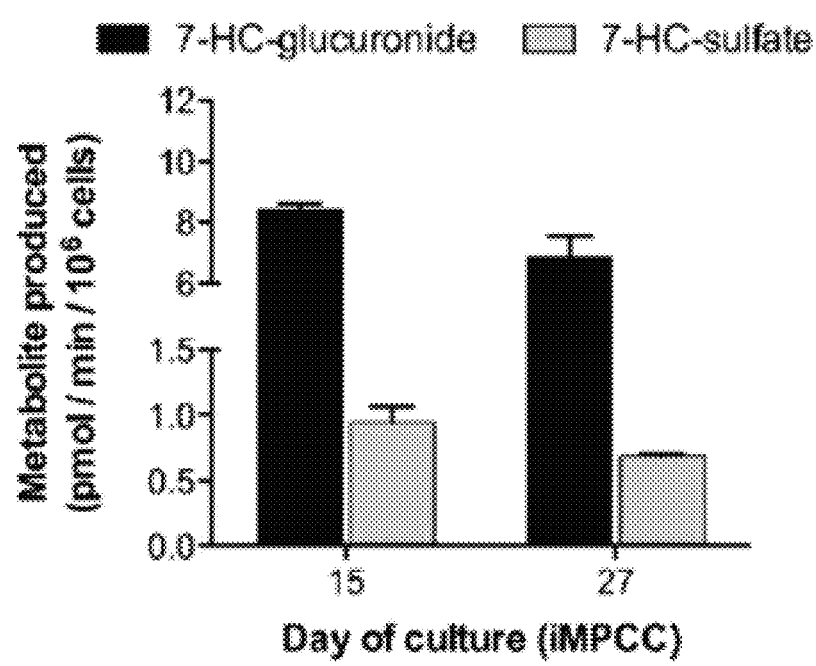
FIG. 29 Time-course of coupled phase-I and phase-II enzymatic activity in iMPCCs. iMPCCs were dosed with 50 μM coumarin and amounts of 7-hydroxycoumarin-glucuronide and 7-hydroxycoumarin-sulfate were quantified in cell culture supernatants using LC-MS/MS (Integrated Analytical Solutions, Berkeley, Calif.). CYP2A6 first generates 7-hydroxycoumarin prior to the subsequent conjugation reactions. All error bars represent standard deviations (n=3).

The magnitude of albumin and urea secretion in iMPCCs was significantly greater (5-20×) than in pure iHep culture formats (FIG. 17B). Rates of secretion reached steady state by the first week in culture and were maintained for 4 weeks in iMPCCs. Despite higher functional maturity, alpha-fetoprotein (AFP) was still detected in supernatants from iMPCCs, albeit the albumin:AFP ratio in iMPCCs increased over time (i.e. AFP declined over time while albumin remained relatively stable), suggesting an improvement in the maturation status of iHeps in iMPCCs (FIGS. 26A-B). Furthermore, iMPCCs displayed stability of CYP450 enzyme activities for at least 4 weeks (FIGS. 18A-18C). CYP3A4 activity also remained stable in pure iHep cultures without fibroblasts for 4 weeks, potentially due to the stable expression of HNF6, a transcriptional regulator of CYP3A4, in all models tested (FIG. 17A). However, the activities of other major CYP450s declined in pure iHep cultures and were significantly is lower (~7-30%) than in iMPCCs, as assessed by luminescence-based and FDA-approved CYP450 substrates (FIGS. 18A-18C, FIG. 27). Even micropatterning iHeps alone without co-culture (i.e. iMPH) yielded higher activities of some CYP450s (i.e. CYP2C9) on a per cell basis as compared to iCCs (FIG. 28A-C). Also detected were coupled phase-I (CYP2A6) and phase-II (glucuronidation, sulfation) metabolism in iMPCCs at higher levels than in pure iHep cultures (FIG. 18D, FIG. 29).

Figure 30A:
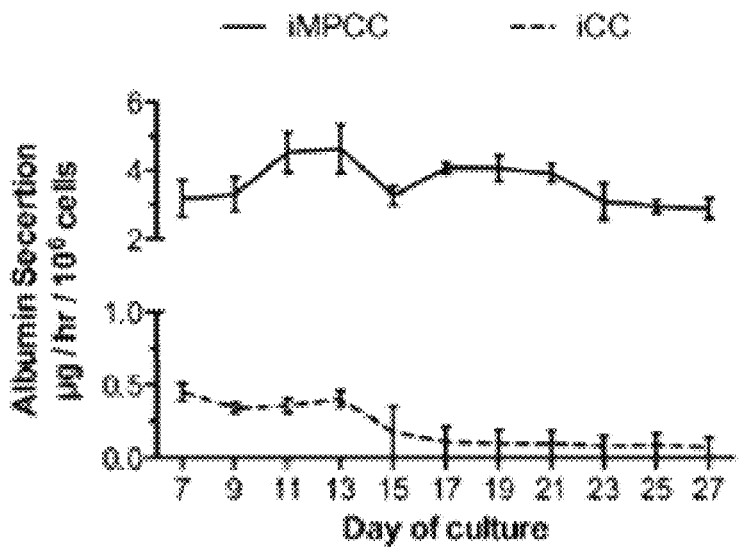
Figure 30B:
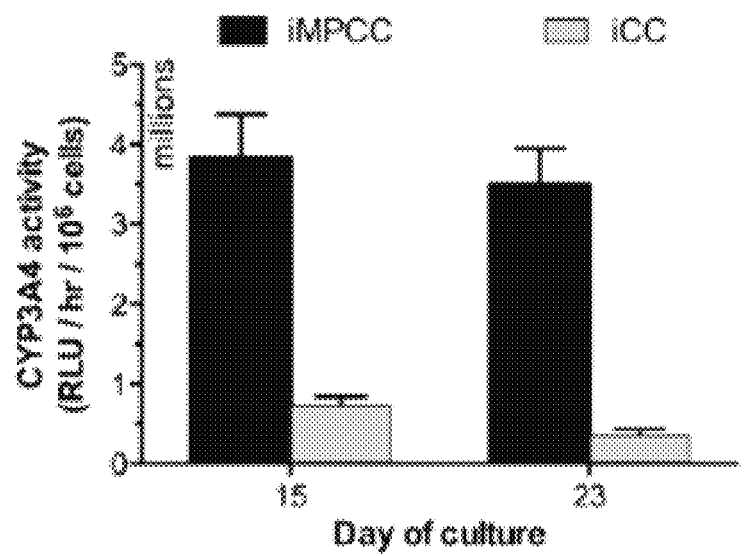

In order to enable on-demand creation of cultures using the same iHep batch, stable functions of cryopreserved iHeps from two different donors (one derived from fibroblasts and another from peripheral blood mononuclear cells were demonstrated in iMPCCs (FIGS. 30A-B, 31A-B). In contrast, cryopreserved iHeps cultured in iCCs did not display stable CYP3A4 activity over time or the same CYP3A4 levels as those cultured in iMPCCs, which was in contrast with the CYP3A4 data obtained in both culture models using fresh iHeps from the same donor (FIG. 18C vs. FIG. 30B).

Example 9

CYP450 Induction Studies

Figures 19A, 19B, 19C, 19D, 19E:
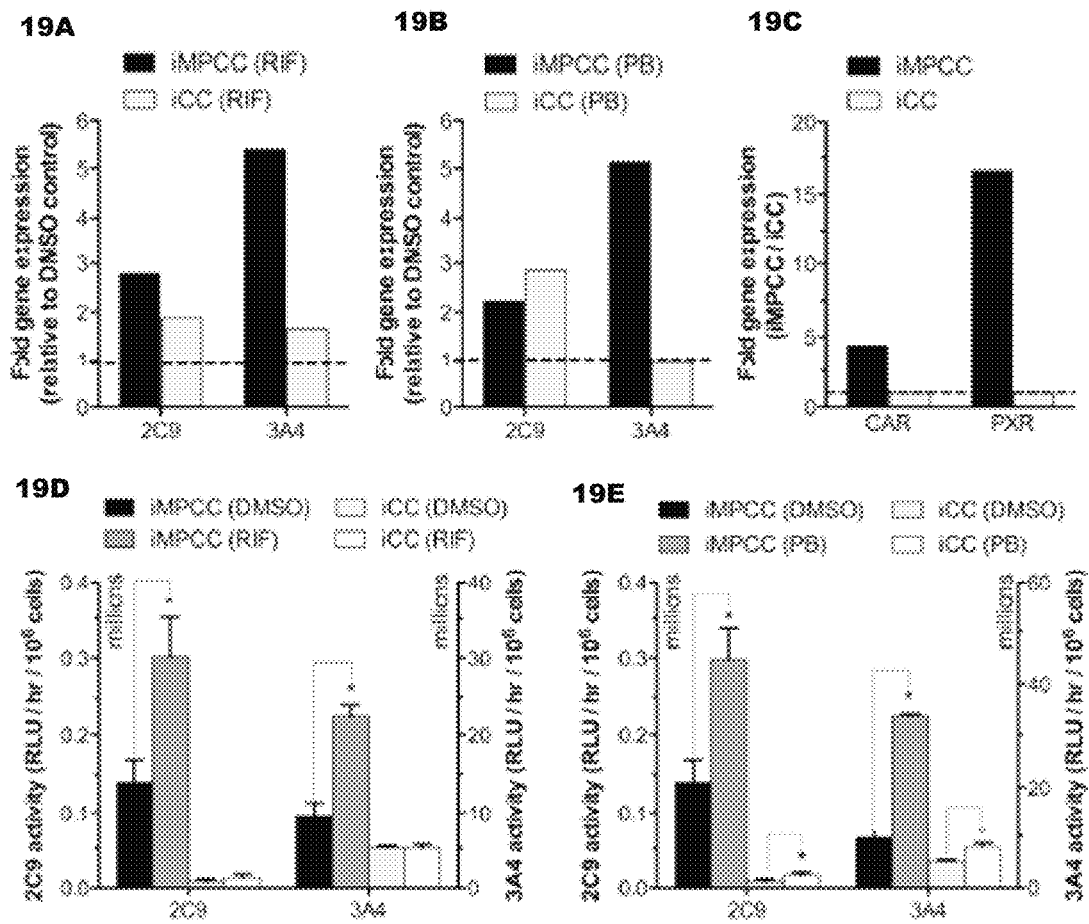
FIGS. 19A, 19B, 19C, 19D and 19E CYP450 induction in iHeps.
Figure 32:
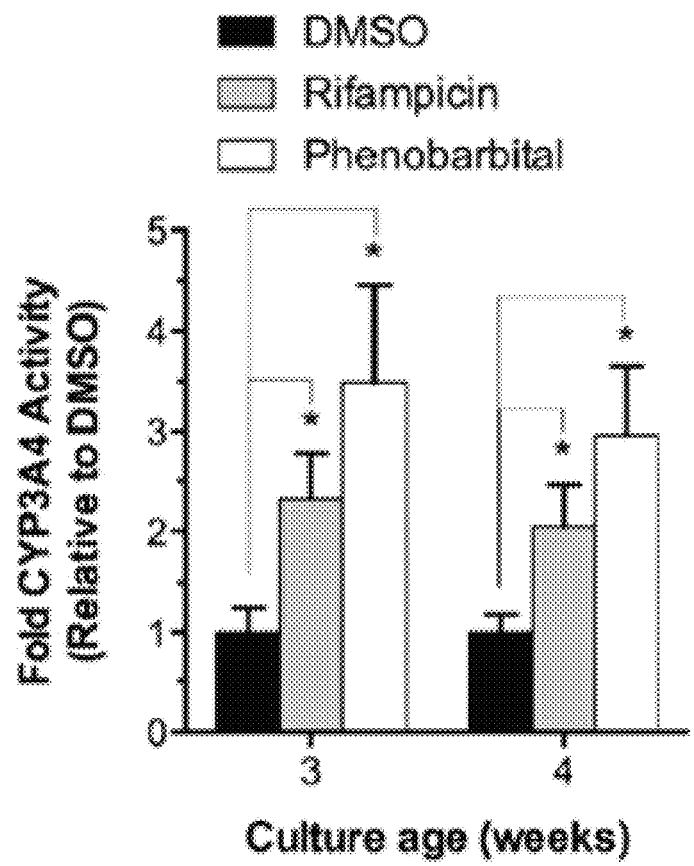
FIG. 32 Repeat drug-mediated CYP450 induction in iMPCCs. Cultures were treated with inducers (rifampicin at 25 μM and phenobarbital at 1 mM) for 4 days followed by incubation with a CYP3A4-specific luciferin-IPA substrate from Promega (day 22). Following 6 more days of culture in drug-free maintenance culture medium, iMPCCs were induced again for 4 days and the aforementioned CYP450 assay repeated (day 32). All error bars represent standard deviation (n=3). *p<0.05.
Figures 33A, 33B, 33C, 33D:
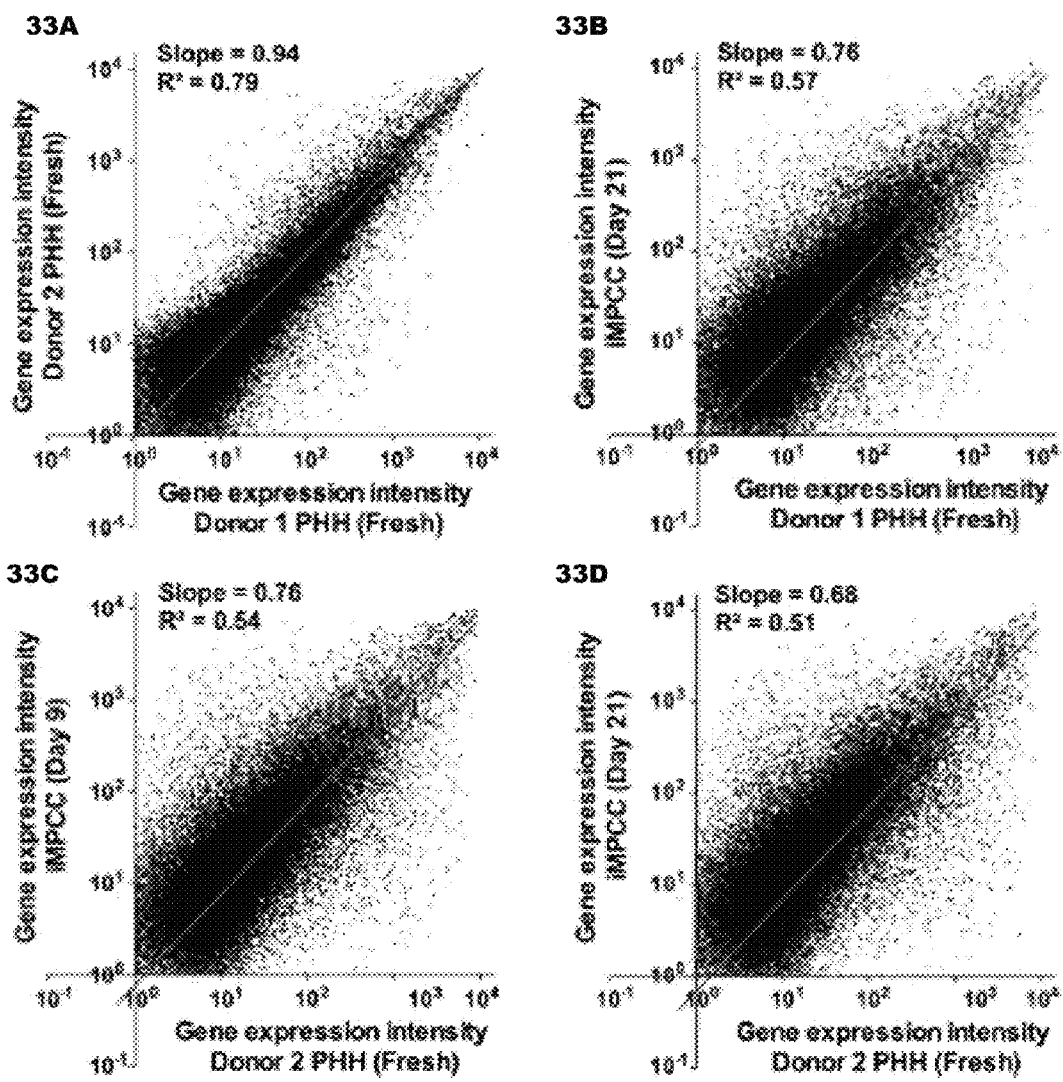
FIGS. 33A, 33B, 33C and 33D Global gene expression profiling of iMPCCs and freshly isolated primary human hepatocytes (PHHs).

Prototypical CYP enzyme inducers rifampicin and phenobarbital induced both CYP450 (3A4, 2C9) mRNA transcripts (FIGS. 19A-19B) and functions in iMPCCs (FIGS. 19D-5E). On the other hand, the induction response was severely blunted in iCCs created from the same donor. Induction response was also not always consistent across gene expression and functional activities in iCCs. Such differences across culture models could be due to the higher expression of key nuclear receptors in iMPCCs as compared to iCCs (FIG. 19C). The same iMPCC wells could be re-induced with drugs over several weeks (FIG. 32).

Example 10

Comparison of iHeps in iMPCCs with Primary Human Hepatocytes

Figures 20A, 20B, 20C, 20D, 20E:
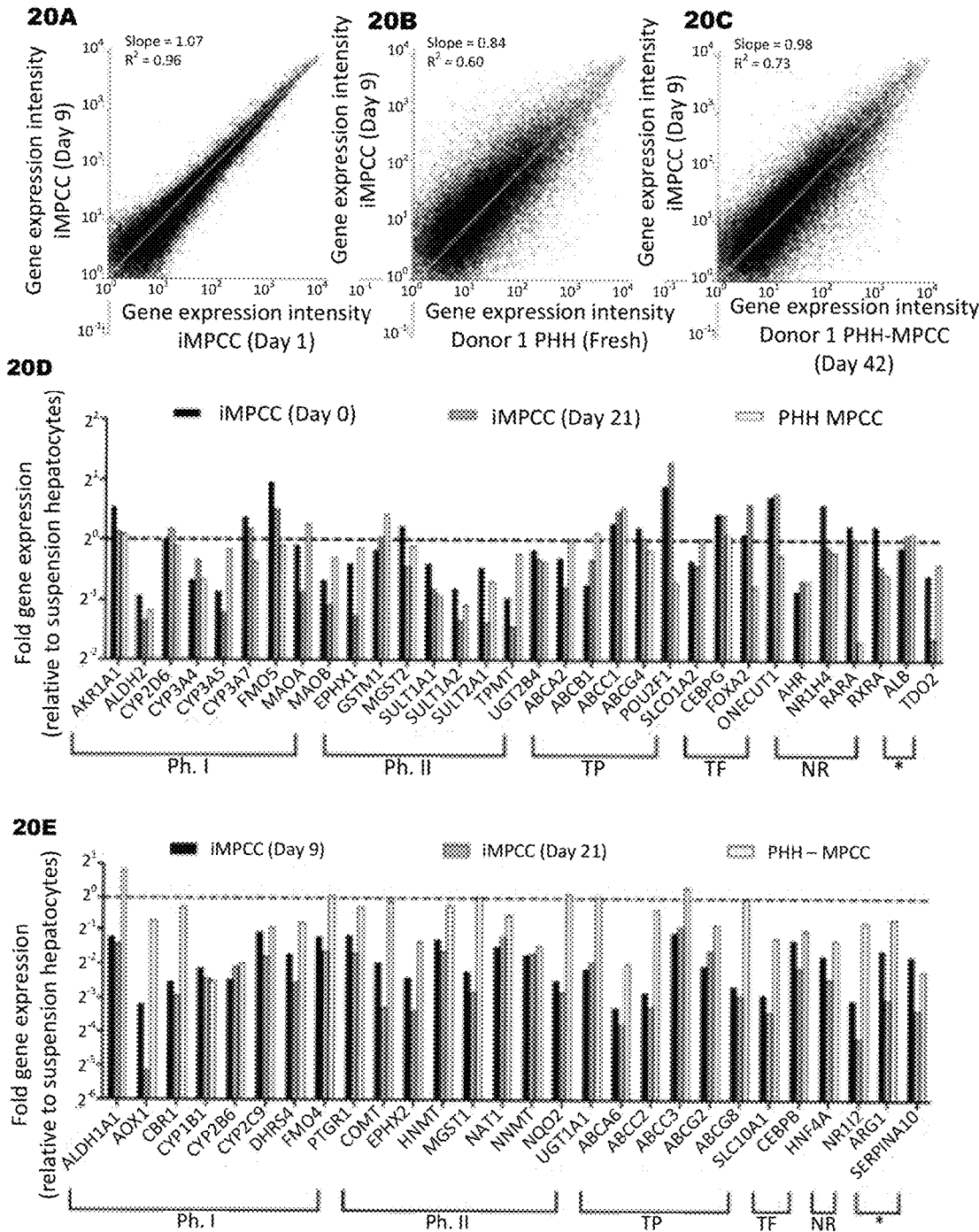
FIGS. 20A, 20B, 20C, 20D and 20E Global gene expression profiling of iHeps and freshly isolated primary human hepatocytes (PHHs).
Figures 34A, 34B:
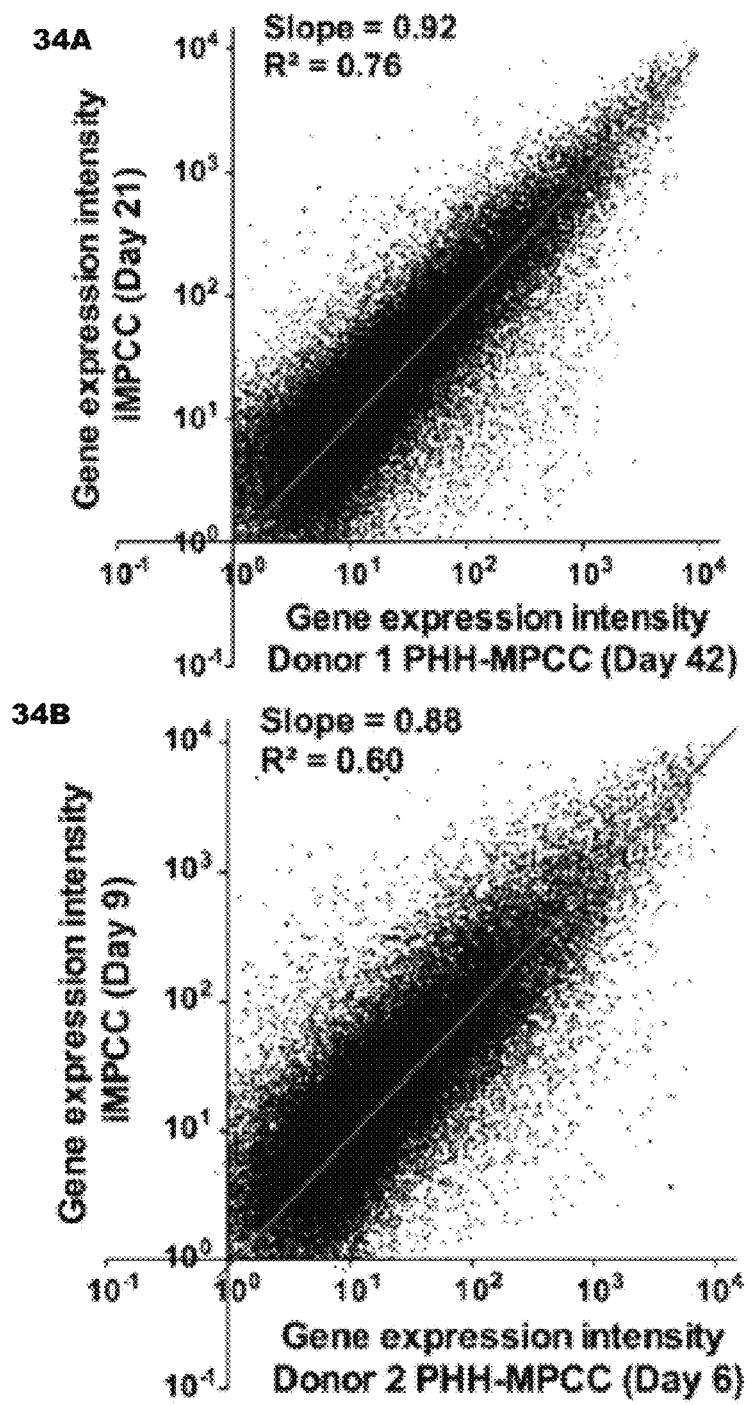
FIGS. 34A, 34B, and 34C Global gene expression profiling of iHeps in iMPCCs and primary human hepatocytes (PHHs) stabilized in PHH-MPCCs. Scatter is plot analysis comparing gene expression intensities (Affymetrix whole genome human microarray) in iMPCCs (day 9 and day 21) created from a single iPSC donor to expression intensities in PHH-MPCCs generated from 2 human donors (PHH donor 1 comparisons shown in panel FIG. 34A and PHH donor 2 comparisons shown in panels FIGS. 34B-C).
Figure 34C:
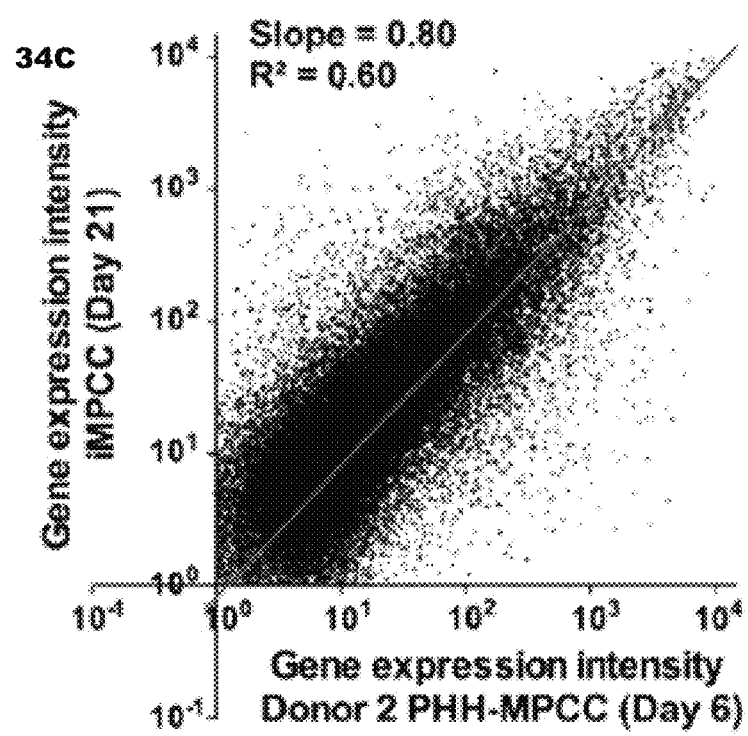
Figure 35:
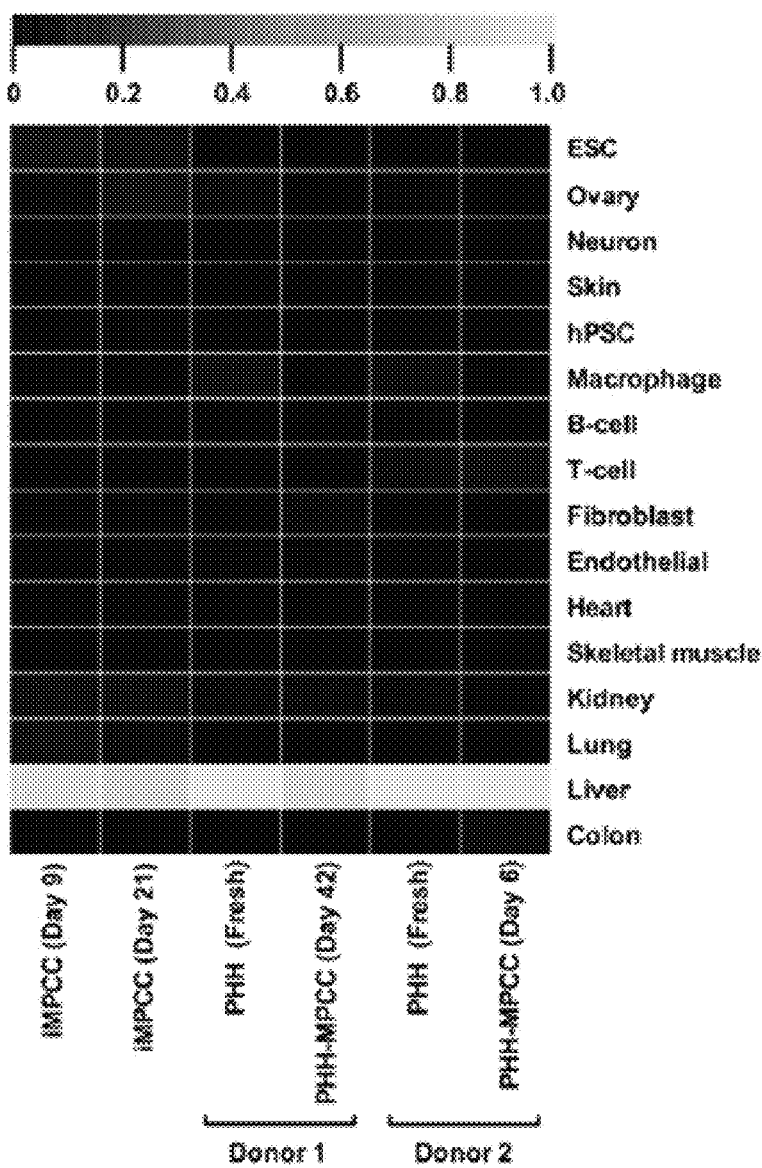
FIG. 35 CellNet cell type and tissue classification of microarray samples from iMPCCs, freshly isolated primary human hepatocytes (PHHs), and PHH-MPCCs. Cell and tissue (C/T) classification scores are displayed in heat map format. C/T scores indicate the probability that a given sample expresses gene regulatory network (GRN) genes to the same extent as those found in tissue specific training data. Liver classification scores for iMPCCs (0.880 for day 9 and 0.837 for day 21 cultures) were similar to scores observed in freshly isolated (0.967 for PHH donor 1 and 0.992 for PHH donor 2) and PHH-MPCCs (0.864 for PHH donor 1 and 0.975 for PHH donor 2). iHeps were classified exclusively as liver with C/T classification scores for all other tissue types 0.09. More details for the CellNet analysis schemes are provided in (2).
Figure 36:
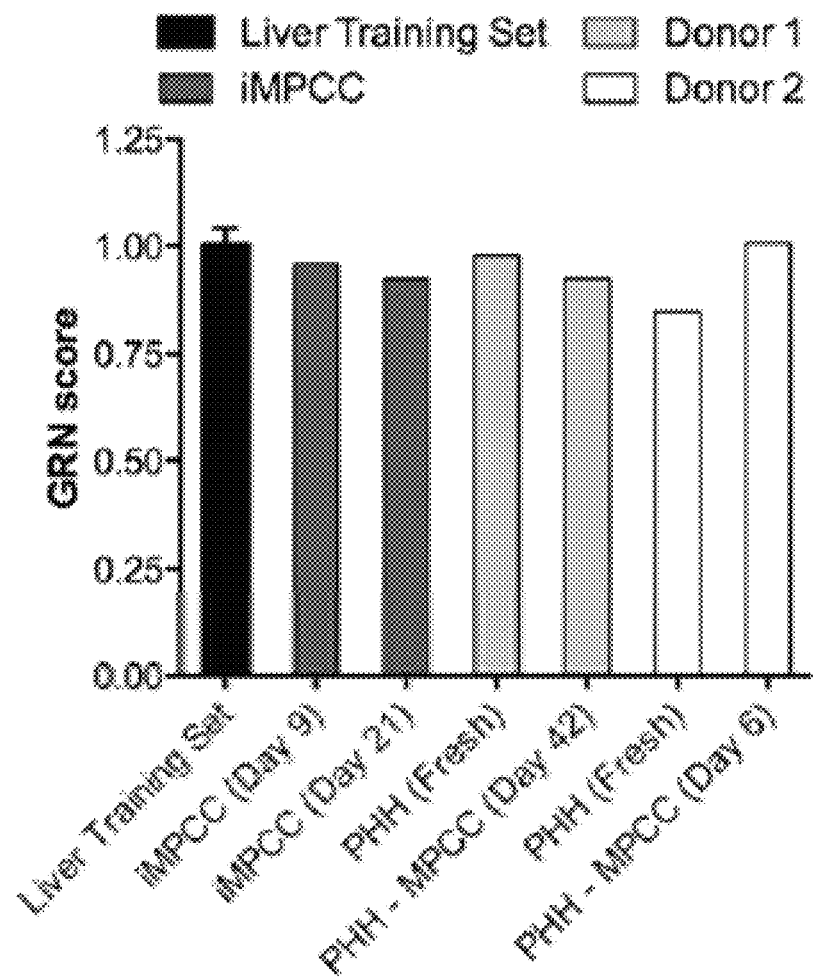
FIG. 36 Supplemental

The transcriptome of iHeps in iMPCCs was relatively stable (linear regression analysis, $R^2=0.96$, slope=1.07) over several weeks in culture, as assessed via Affymetrix whole genome microarrays (FIG. 20A). Gene expression in iMPCCs was is also compared with previously published data from two donors of freshly isolated PHHs and when the same donors were stabilized in PHH-MPCCs, but without the Matrigel™ overlay. iMPCCs at multiple time-points in culture exhibited strong correlations in global gene expression with fresh PHHs ($R^2=0.51-0.6$, slope=0.68-0.84) and PHH-MPCCs ($R^2=0.6-0.73$, slope=0.88-0.98) (FIG. 20B-C, FIGS. 33A-33D and 34A-34C). Part of the variability observed in gene expression between iMPCCs and PHHs could likely be attributed to donor differences as also observed when comparing gene expression between two PHH donors ($R^2=0.79$, slope=0.94) (FIG. 34A). Analysis of iMPCC microarrays by CellNet (P. Cahan et al., Cell 158: 903-15 (2014)), a network biology platform used to evaluate the fidelity of engineered cells by measuring the establishment of tissue-specific gene regulatory networks (GRNs), exclusively classified iMPCCs as liver (classifications scores 0.837-0.880) (FIG. 35). Moreover, the liver-specific GRN establishment scores for iMPCCs (0.925-0.959) fell within the range of scores for the two PHH donors, both when freshly isolated (0.848-0.978) and when stabilized in PHH-MPCCs (0.924-1.005) (FIG. 36).

Figure 37A:
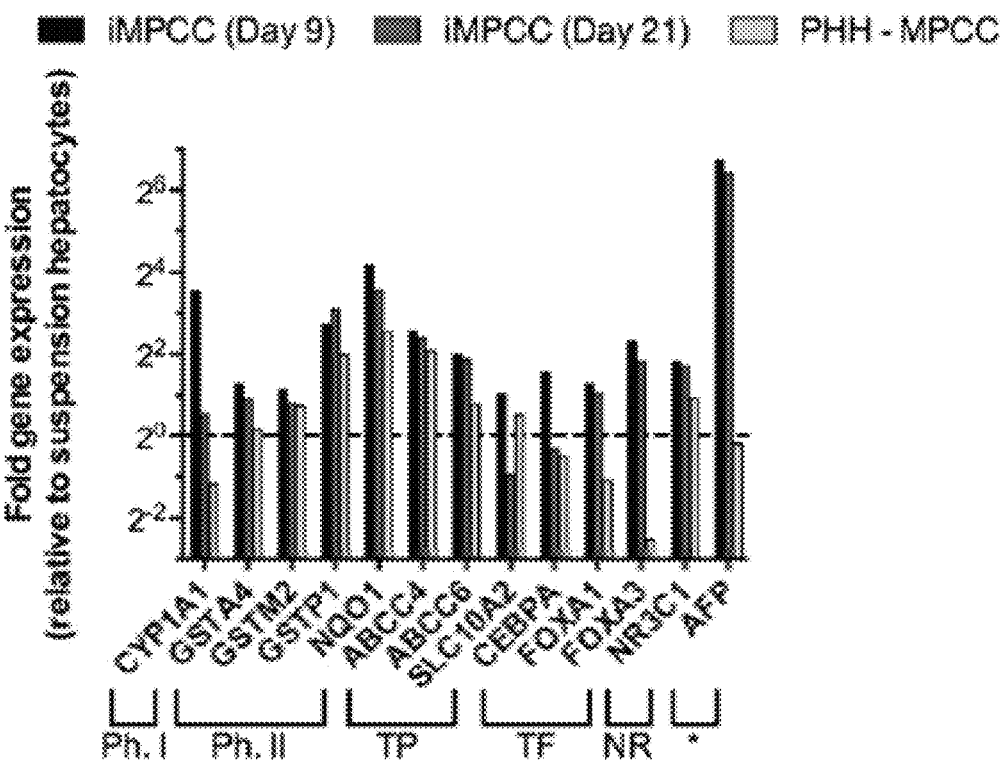
FIGS. 37A and 37B Liver-specific transcripts in iMPCCs with greater than 200% or less than 10% of the gene expression intensities observed in freshly isolated primary human hepatocytes (PHHs). RNA was extracted from 2 donors of freshly isolated PHHs prior to plating (1). PHHs were plated in the micropatterned co-culture format (PHH-MPCCs), and RNA was extracted at day 42 (PHH donor 1) or day 6 (PHH donor 2). iMPCCs were created using iHeps from iPSC donor 1 (see methods) FIG. 37A iMPCC transcripts with greater than 200% of PHH levels.
Figure 37B:
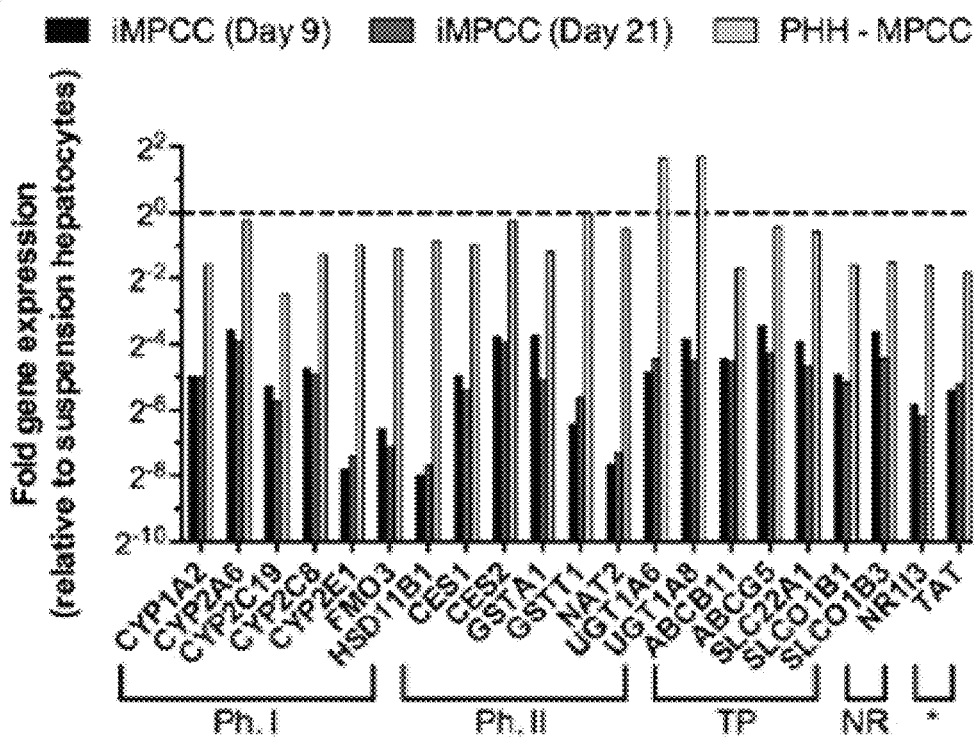

Gene expression values of ~95 liver-specific transcripts within diverse categories were next compared between iMPCCs and two donors of freshly isolated PHHs and the same PHH donors stabilized in PHH-MPCCs. We found that the majority of liver transcripts in iMPCCs were expressed between 10% and 200% of the levels seen in fresh PHHs (FIGS. 20D-20E). A subset of transcripts was shown to be significantly up-regulated in iMPCCs relative to PHHs, including AFP, which was ~100-fold greater, while a subset of transcripts was expressed at levels less than 10% of PHHs (FIGS. 37A and 37B).

Figure 21A:
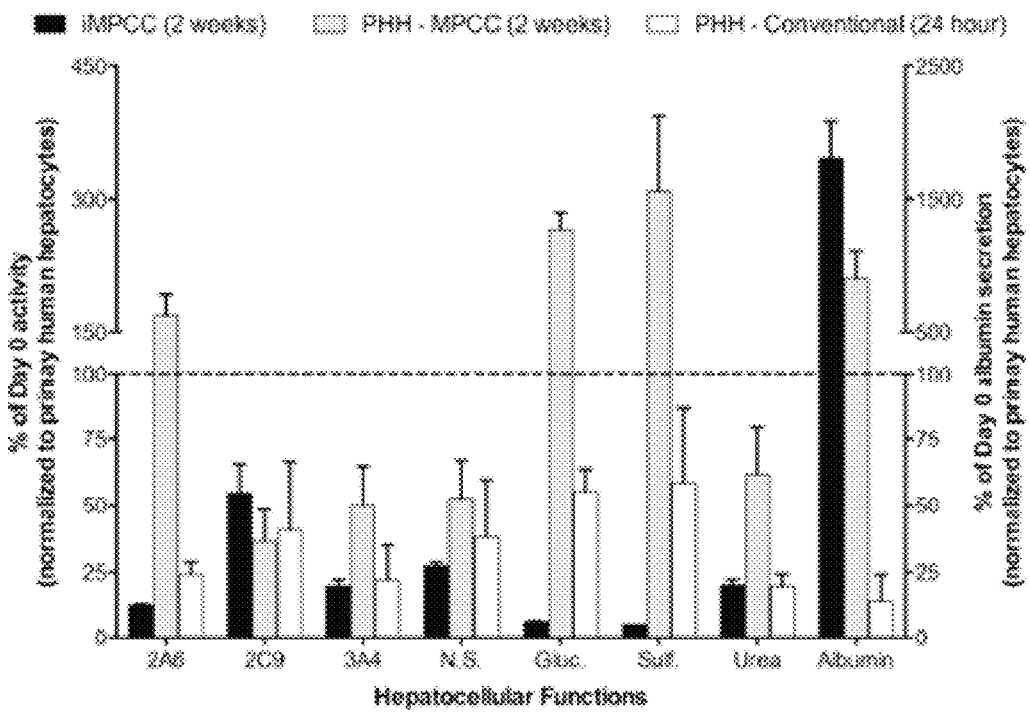
FIGS. 21A, 21B, and 21C Comparison of liver phenotype in iHeps and cryopreserved primary human hepatocytes (PHHs).

Liver functions in iMPCCs were compared with cryopreserved PHHs (2 donors) that were cultured in both conventional confluent and PHH-MPCC formats (FIG. 21A). PHH-MPCCs were observed to outperform PHH conventional cultures for 7 of 8 functions measured, and for 4 of 8 functions, PHH-MPCCs demonstrated increased activity levels over PHHs on day of seeding (day 0). For 7 of 8 functions measured, iMPCCs were found to function between 5% (sulfation) and 55% (CYP2C9) of day 0 PHH levels. Albumin production was substantially greater in iMPCCs and PHH-MPCCs than in day 0 PHHs and conventional PHH cultures, which is believed due to the recovery of this function in more stable culture formats. iMPCCs displayed ~2-fold more albumin production than observed in PHH-MPCCs, however donor dependent differences likely underlie these observed differences.

Figure 21B:
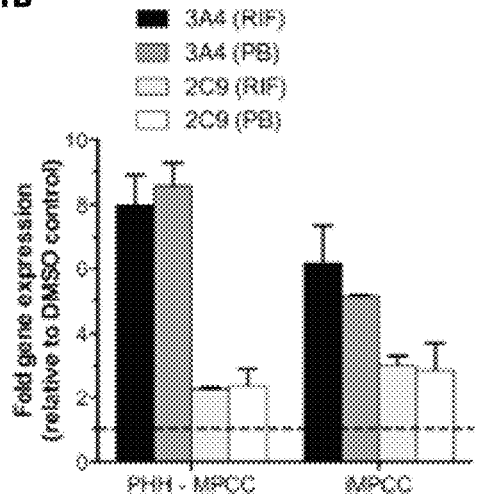
Figure 21C:
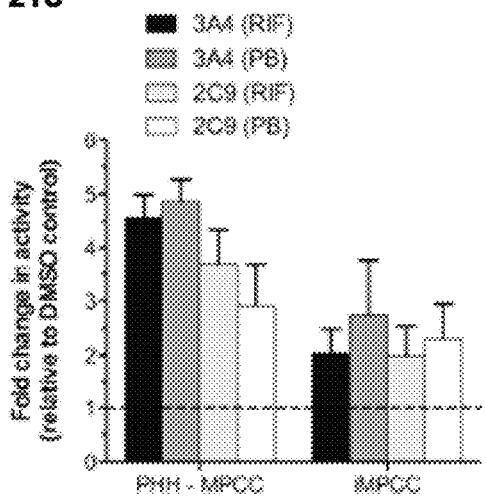
Figure 38:
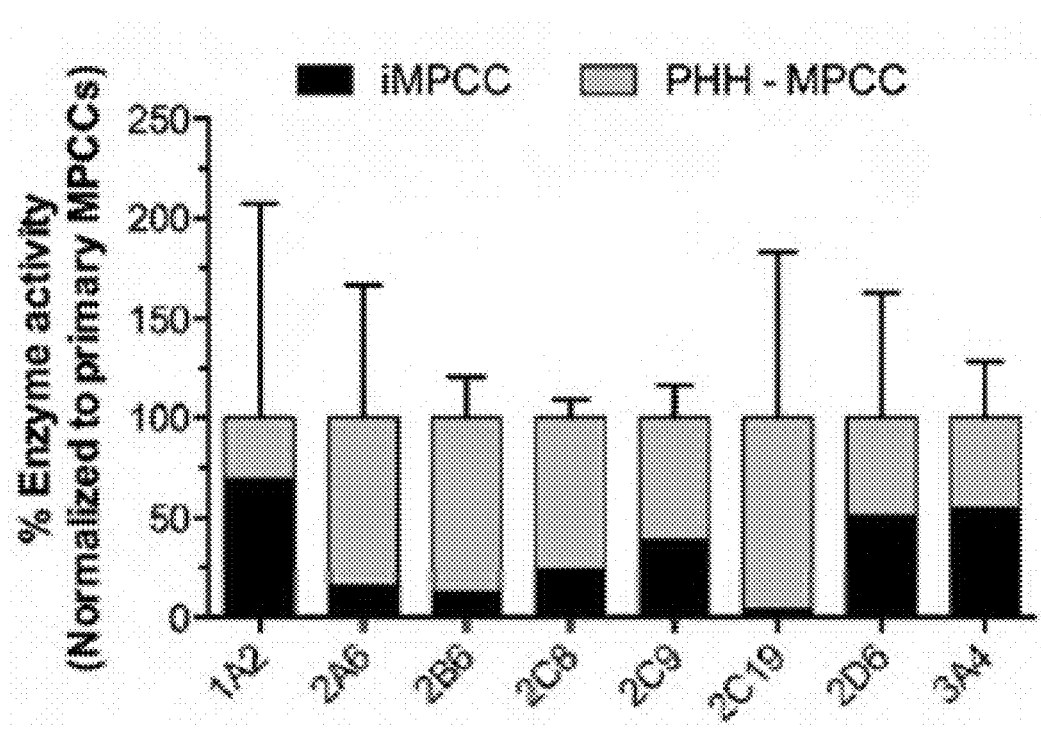
FIG. 38 CYP450 characterization of PHH-MPCCs and iMPCCs using FDA-approved substrates requiring LC-MS/MS analyses. CYP450 activities in PHH-MPCCs are averaged from 3-5 donors between 1 and 2 weeks of culturing when enzyme activities are known to be stable. For iHeps in iMPCCs, data from day 15 of culture is shown but trends were seen over multiple time-points. Enzyme, substrate, metabolite measured: 1A2, phenacetin, acetaminophen; 2A6, coumarin, 7-hydroxy-coumarin; 2B6, bupropion HCl, hydroxylbupropion; 2C8, paclitaxel, 6-alpha-hydroxy-paclitaxel; 2C9, tolbutamide, 4-hydroxy-tolbutamide; 2C19, s-mephenytoin, 4-hydroxy-s-mephenytoin; 2D6, dextromethorphan, dextrorphan; and 3A4, testosterone, 6-beta-hydroxy-testosterone. All error bars represent standard deviation (n=3-5).

In addition to using luminescence-based substrates, the activities of major CYP450s in iMPCCs and PHH-MPCCs were measured using FDA-approved enzyme-specific substrates (FIG. 38). Activities of CYP450 enzymes in iMPCCs ranged from ~5% (CYP2C19) to ~70% (CYP1A2) of PHH-MPCC levels, averaged across several donors. Dosing with phenobarbital and rifampicin resulted in induction of CYP450 (3A4, 2C9) transcripts and functions in both iMPCCs and PHH-MPCCs (FIG. 21B-C). While the drug-mediated fold induction of CYP450 transcripts in iMPCCs was similar (60-130%) to that observed in PHH-MPCCs, the induction in CYP450 functions was typically lower (44-79%). Induction of iMPCC CYP1A2 activity in a dose-dependent manner was observed using β-naphthoflavone and omeprazole, with fold induction in iMPCCs reaching ~70% of values in PHH-MPCCs (FIGS. 39A-39D).

Example 11

Figure 22A:
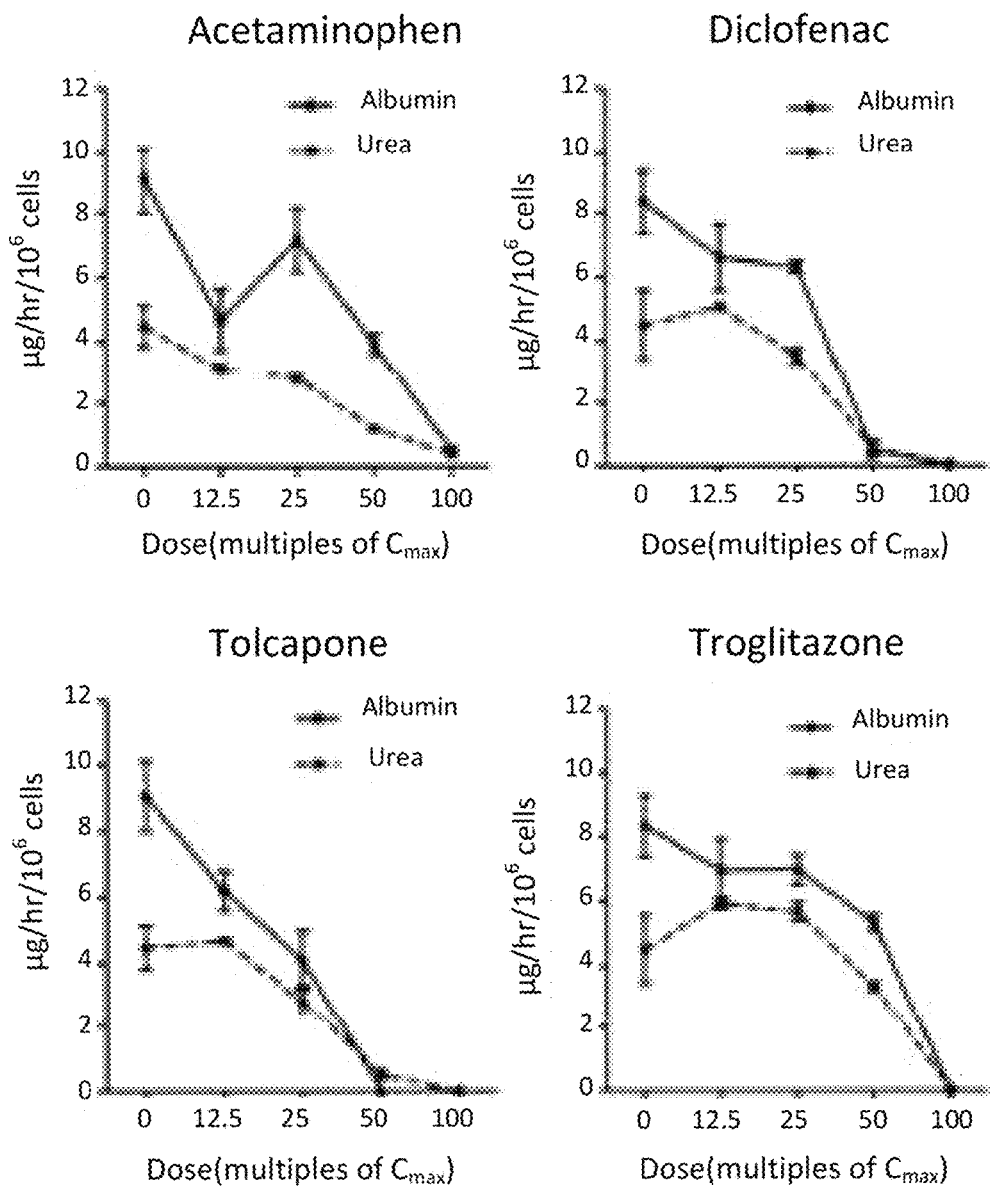
FIGS. 22A and 22B Assessment of drug toxicity in iMPCCs.
Figure 22B:
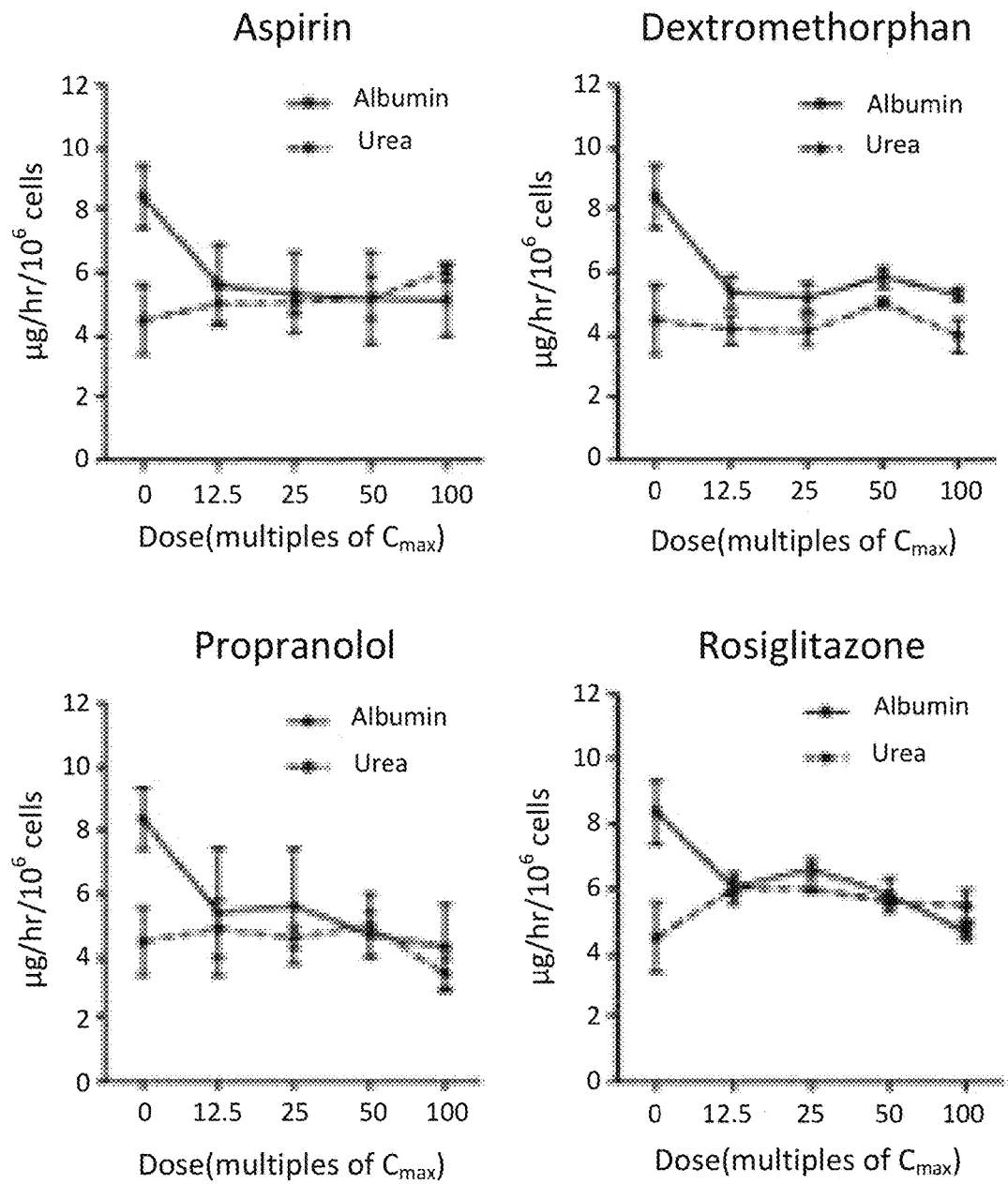

Drug Toxicity Studies iMPCCs were treated for 8 days with multiple doses of known hepatotoxins (acetaminophen, amiodarone, tolcapone, troglitazone) and non-liver-toxins (aspirin, dextromethorphan, diclofenac, propranolol). Albumin and urea production, previously shown to be sensitive markers for detecting drug-induced hepatotoxicity in vitro, declined significantly in iMPCCs following exposure to increasing doses of the toxins (FIG. 22A), while the non-toxins minimally affected these functions (FIG. 22B).

All patents and publications mentioned in the specification are indicative of the levels of those skilled in the art to which the present disclosure pertains. All such patents and publications are herein incorporated by reference to the same extent as if each individual publication was specifically and individually indicated to be incorporated by reference.

What is claimed is:

1. A composition comprising:
a population of human hepatocytes derived from induced human pluripotent stem cells and a population of 3T3-J2 fibroblasts in co-culture (population of hepatocytes in co-culture) in vitro;
a culture substrate, wherein the cell populations are disposed in a micropattern on the culture substrate and the micropattern comprises a predetermined two-dimensional pattern of multiple microdots, the micropattern defined by a microdot diameter and a center-to-center spacing between each of any two neighboring microdots, wherein each microdot has a diameter of about 500 µm and the center-to-center spacing between each of any two neighboring microdots is about 1200 µm, and the microdots comprise the human hepatocytes derived from induced human pluripotent stem cells and the space between the microdots comprises the 3T3-J2 fibroblast population; and
a layer of material comprising gelatinous protein mixture secreted by Engelbreth-Holm-Swarm (EHS) mouse sarcoma cells disposed on the co-culture,
wherein the population of hepatocytes in co-culture exhibits a higher level of cytochrome P450 3A4 (CYP3A4) enzyme activity by at least day 22 of culture as compared to a population of human hepatocytes derived from induced pluripotent stem cells and not co-cultured with a population of 3T3-J2 fibroblasts (population of hepatocytes not in co-culture).

2. The composition of claim 1, wherein the culture substrate comprises a glass surface, a polystyrene surface, or a silicon surface.

3. The composition of claim 1, wherein the population of hepatocytes in co-culture further exhibits a higher level of differentiation toward an adult human hepatocyte phenotype as determined by measuring at least one of liver-specific gene expression, albumin secretion, urea synthesis, Phase I enzyme activity, Phase II enzyme activity, low density lipoprotein (LDL) uptake, and number of active bile canaliculi in the co-cultured hepatocytes and comparing the measurement to that obtained in the population of hepatocytes not in co-culture.

4. The composition of claim 1, wherein the population of human hepatocytes derived from induced human pluripotent stem cells is derived from a population of previously cryopreserved induced pluripotent stem cell derived hepatocytes.

5. A method of culturing a population of hepatocytes derived from induced pluripotent human stem cells in vitro comprising: co-culturing the population of hepatocytes derived from induced pluripotent stem cells with a population of 3T3-J2 fibroblasts and maintaining the co-culture for at least about 8 days, wherein the cell populations are disposed in a micropattern on a culture substrate and the micropattern comprises a predetermined two-dimensional pattern of multiple microdots, the micropattern defined by a microdot diameter and a center-to-center spacing between each of any two neighboring microdots, wherein each microdot has a diameter of about 500 µm and the center-to-center spacing between each of any two neighboring microdots is about 1200 µm and the microdots comprise the human hepatocytes derived from induced human pluripotent stem cells and the space between the microdots comprises the 3T3-J2 fibroblast cell population, wherein a layer of material comprising gelatinous protein mixture secreted by Engelbreth-Holm-Swarm (EHS) mouse sarcoma cells is disposed on the co-culture, and wherein the population of hepatocytes in co-culture exhibits a higher level of cytochrome P450 3A4 (CYP3A4) enzyme activity by at least day 22 of culture as compared to a population of human hepatocytes derived from induced pluripotent stem cells and not co-cultured with a population of 3T3-J2 fibroblasts.

6. The method of claim 5, wherein the culture substrate comprises a glass surface, a polystyrene surface, or a silicon surface.

7. The composition of claim 4, wherein the wherein the population of hepatocytes in co-culture exhibits a higher level of cytochrome P450 3A4 (CYP3A4) enzyme activity by at least day 15 of culture as compared to the population of hepatocytes not in co-culture.

8. The composition of claim 1, wherein the wherein the population of hepatocytes in co-culture exhibits a higher level of cytochrome P450 3A4 (CYP3A4) enzyme activity by at least day 15 of co-culture as compared to the population of hepatocytes not in co-culture.

9. The composition of claim 1, wherein the population of hepatocytes not in co-culture is not disposed in a micropattern on the culture substrate.

10. The composition of claim 3, wherein the higher level of differentiation toward an adult human hepatocyte phenotype is determined by measuring albumin secretion, wherein the population of hepatocytes in co-culture exhibits a higher level of albumin secretion as compared to the population of hepatocytes not in co-culture.

11. The composition of claim 3, wherein the higher level of differentiation toward an adult human hepatocyte phenotype is determined by measuring Phase II enzyme activity and wherein the population of hepatocytes in co-culture exhibits a higher level of Phase II enzyme activity by at least day 15 of culture as compared to the population of hepatocytes not in co-culture.

12. The composition of claim 3, wherein the higher level of differentiation toward an adult human hepatocyte phenotype is determined by measuring Phase I enzyme activity, wherein the Phase I enzyme is at least one of cytochrome P1A2 (CYP1A2), cytochrome P2B6 (CYP2B6), and cytochrome 2D6 (CYP2D6), and wherein the Phase I enzyme activity in the population of hepatocytes in co-culture is higher than the Phase I enzyme activity in the population of hepatocytes not in co-culture.

13. The composition of claim 1, wherein the population of hepatocytes in co-culture exhibits a higher level of gene expression of at least one of pregnane X receptor (PXR) and constitutive androstane receptor (CAR) as compared to the population of hepatocytes not in co-culture, wherein the higher level of gene expression is determined by measuring the mRNA transcripts for at least one of PXR and CAR in the population of hepatocytes in co-culture and comparing the measurement to that obtained in the population of hepatocytes not in co-culture.

14. The composition of claim 1, wherein the population of hepatocytes in co-culture exhibits a higher ratio of cytochrome 3A4 (CYP3A4) mRNA transcripts to cytochrome 3A7 (CPY3A7) mRNA transcripts by at least day 16 of culture as compared to the population of hepatocytes not in co-culture.

15. The composition of claim 1, wherein the population of hepatocytes in co-culture exhibits higher cytochrome P450 (CYP450) induction as compared to the population of hepatocytes not in co-culture, when exposed to a drug.

16. The composition of claim 15, wherein the cytochrome P450 (CYP450) induction is determined by an increase in cytochrome P2C9 (CYP2C9) activity in the population of hepatocytes in co-culture as compared to the population of hepatocytes not in co-culture.

17. The composition of claim 16, wherein the drug is selected from rifampicin and phenobarbital.

18. The composition of claim 1, wherein the cytochrome P450 3A4 (CYP3A4) enzyme activity is determined by using a luminescence-based assay.

19. The composition of claim 18, wherein the wherein the population of hepatocytes in co-culture exhibits a higher level of cytochrome P450 3A4 (CYP3A4) enzyme activity by at least day 15 of co-culture as compared to the population of hepatocytes not in co-culture.

20. The composition of claim 18, wherein the population of human hepatocytes derived from induced human pluripotent stem cells is derived from a population of previously cryopreserved induced pluripotent stem cell derived hepatocytes.

21. The composition of claim 20, wherein the wherein the population of hepatocytes in co-culture exhibits a higher level of cytochrome P450 3A4 (CYP3A4) enzyme activity by at least day 15 of culture as compared to the population of hepatocytes not in co-culture.

22. The composition of claim 18, wherein the population of hepatocytes in co-cultured further exhibits a higher level of differentiation toward an adult human hepatocyte phenotype as determined by measuring at least one of liver-specific gene expression, albumin secretion, urea synthesis, Phase I enzyme activity, Phase II enzyme activity, LDL uptake, and number of active bile canaliculi in the co-cultured hepatocytes and comparing the measurement to that obtained in the population of hepatocytes not in co-culture.

23. The composition of claim 22, wherein the higher level of differentiation toward an adult human hepatocyte phenotype is determined by measuring albumin secretion, wherein the population of hepatocytes in co-culture exhibits a higher level of albumin secretion as compared to the population of hepatocytes not in co-culture.

24. The composition of claim 22, wherein the higher level of differentiation toward an adult human hepatocyte phenotype is determined by measuring Phase II enzyme activity and wherein the population of hepatocytes in co-culture exhibits a higher level of Phase II enzyme activity by at least day 15 of culture as compared to the population of hepatocytes not in co-culture.

25. The composition of claim 22, wherein the higher level of differentiation toward an adult human hepatocyte phenotype is determined by measuring Phase I enzyme activity, wherein the Phase I enzyme is at least one of cytochrome P1A2 (CYP1A2), cytochrome P2B6 (CYP2B6), and cytochrome 2D6 (CYP2D6), and wherein the Phase I enzyme activity in the population of hepatocytes in co-culture is higher than the Phase I enzyme activity in the population of hepatocytes not in co-culture.

26. The composition of claim 22, wherein the population of hepatocytes in co-culture exhibits a higher level of gene expression of at least one of pregnane X receptor (PXR) and constitutive androstane receptor (CAR) as compared to the population of hepatocytes not in co-culture, wherein the higher level of gene expression is determined by measuring the mRNA transcripts for at least one of PXR and CAR in the population of hepatocytes in co-culture and comparing the measurement to that obtained in the population of hepatocytes not in co-culture.

27. The composition of claim 18, wherein the population of hepatocytes in co-culture exhibits a higher ratio of cytochrome 3A4 (CYP3A4) mRNA transcripts to cytochrome 3A7 (CPY3A7) mRNA transcripts by at least day 16 of culture as compared to the population of hepatocytes not in co-culture.

28. The composition of claim 18, wherein the population of hepatocytes in co-culture exhibits higher cytochrome P450 (CYP450) induction as compared to the population of hepatocytes not in co-culture, when exposed to a drug.

29. The composition of claim 28, wherein the cytochrome P450 (CYP450) induction is determined by an increase in cytochrome P2C9 (CYP2C9) activity in the population of hepatocytes in co-culture as compared to the population of hepatocytes not in co-culture.

30. The composition of claim 29, wherein the drug is selected from rifampicin and phenobarbital.

* * * * *